(12) United States Patent
Steinecker et al.

(10) Patent No.: US 8,512,457 B2
(45) Date of Patent: Aug. 20, 2013

(54) DIFFERENTIAL ACCELERATION CHROMATOGRAPHY

(75) Inventors: William H. Steinecker, Farmersville, OH (US); Jagdish Shah, Southington, CT (US); Oleg Zhdaneev, Bergen (NO); Gordon R. Lambertus, Indianapolis, IN (US); Hua Chen, Cambridge, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 13/290,482

(22) Filed: Nov. 7, 2011

(65) Prior Publication Data
US 2012/0048108 A1   Mar. 1, 2012

Related U.S. Application Data

(62) Division of application No. 11/949,362, filed on Dec. 3, 2007.

(51) Int. Cl.
*B01D 53/02* (2006.01)
*G01N 30/02* (2006.01)
*G01N 30/56* (2006.01)

(52) U.S. Cl.
USPC ............. 96/101; 95/83; 73/23.39; 73/23.42

(58) Field of Classification Search
CPC .............................................. G01N 2030/567
USPC .................... 73/23.35, 23.39, 23.42; 95/82, 95/83; 96/101
See application file for complete search history.

(56) References Cited

U.S. PATENT DOCUMENTS

| | | | |
|---|---|---|---|
| 3,820,660 A | 6/1974 | Halasz et al. | |
| 3,836,449 A | 9/1974 | Lovelock | |
| 4,719,011 A | 1/1988 | Shalon et al. | |
| 5,135,549 A * | 8/1992 | Phillips et al. | 95/8 |
| 6,190,559 B1 * | 2/2001 | Valaskovic | 210/656 |
| 6,301,952 B1 * | 10/2001 | De Zeeuw et al. | 73/23.35 |
| 6,838,288 B2 * | 1/2005 | Beens | 436/161 |
| 8,132,443 B2 * | 3/2012 | McGill et al. | 73/23.39 |
| 8,323,504 B2 * | 12/2012 | Steinecker | 210/656 |
| 8,329,038 B2 * | 12/2012 | Steinecker | 210/656 |

(Continued)

FOREIGN PATENT DOCUMENTS

| | | |
|---|---|---|
| EP | 1589337 A1 | 10/2005 |
| WO | 8807886 A1 | 10/1988 |
| WO | 2008145457 A1 | 12/2008 |

OTHER PUBLICATIONS

Grushka, "Chromatic Peak Shapes. Their Origin and Dependence on the Experimental Parameters," The Journal of Physical Chemistry, 1972, vol. 76(18): pp. 2586-2593.

(Continued)

*Primary Examiner* — Robert Clemente
(74) *Attorney, Agent, or Firm* — Jakub Michna; Rachel E. Greene; Bridget Laffey

(57) ABSTRACT

Methods and related systems are described for improving component separations in chromatography through novel techniques. The improvements in separation is due primarily to the provision of differential acceleration of the components being separated. Various systems and methods for providing differential acceleration are described including: increasing the cross section of the column towards the column outlet, changing the thickness or other composition of stationary phase within the column, and providing a temperature and/or mobile phase velocity gradient along the column.

19 Claims, 52 Drawing Sheets

(56) References Cited

U.S. PATENT DOCUMENTS

| | | | |
|---|---|---|---|
| 8,377,309 B2* | 2/2013 | Steinecker | 210/656 |
| 2003/0027354 A1 | 2/2003 | Geli | |
| 2004/0020855 A1* | 2/2004 | Allington et al. | 210/656 |
| 2006/0144237 A1 | 7/2006 | Liang et al. | |
| 2006/0243651 A1 | 11/2006 | Ricker | |
| 2007/0204749 A1 | 9/2007 | Adkins | |
| 2009/0139934 A1 | 6/2009 | Steinecker et al. | |
| 2009/0150087 A1 | 6/2009 | Steinecker | |
| 2012/0118156 A1* | 5/2012 | Steinecker | 96/101 |
| 2012/0118805 A1* | 5/2012 | Steinecker | 210/198.2 |
| 2012/0118806 A1* | 5/2012 | Steinecker | 210/198.2 |

OTHER PUBLICATIONS

Lambertus et al., "Design, Fabrication, and Evaluation of Microfabricated Columns for Gas Chromatography," Anal. Chem., 2004, vol. 76: pp. 2629-2637.

Lapidus et al., "Mathematics of Adsorption in Beds. VI the Effect of Longitudinal Diffusion in Ion Exchange and Chromatographic Columns," J. Phys. Chem., 1952, vol. 56: pp. 984-988.

Podmaniczky et al., "Determination of thermodynamic Characteristics from Retention Data in GC," Chromatographia, 1985, vol. 20(10): pp. 591-595.

Reidy et al., "High-Performance, Static-Coated Silicon Microfabricated Columns for Gas Chromatography," Anal. Chem., 2006, vol. 78: pp. 2623-2630.

Snijders et al., "Optimization of temperature-programmed gas chromatographic separations I. Prediction of retention times and peak widths from retention indices," Journal of Chromatography A, 1995, vol. 718: pp. 339-355.

Prudkovskii, "Theory of Chromatography for Columns with a Variable Configuration," Journal of Analytical Chemistry, 2000, vol. 55(5): pp. 443-444.

Michrom BioResources, Inc., exerpts from "HPLC & LC/MS Catalog," 2000-2001: pp. 1-10.

Pirogova et al., "Chrom. 5215: A Study of Variable Diameter Columns in Preparative Gas Chromatography," Journal of Chromatography, 1971, vol. 58: pp. 107-116.

International Search Report of PCT Application No. PCT/US2008/078218 dated Dec. 30, 2008: pp. 1-3.

* cited by examiner

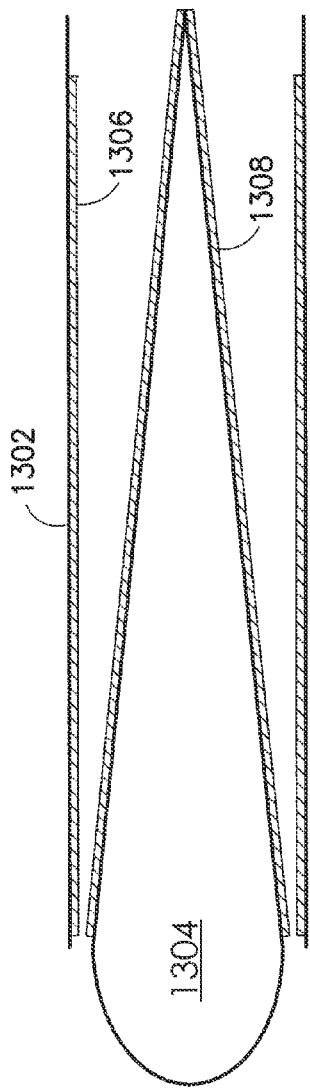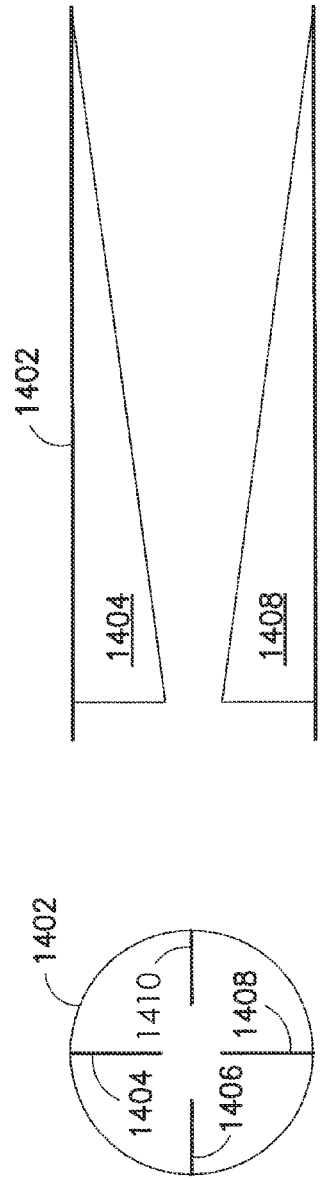

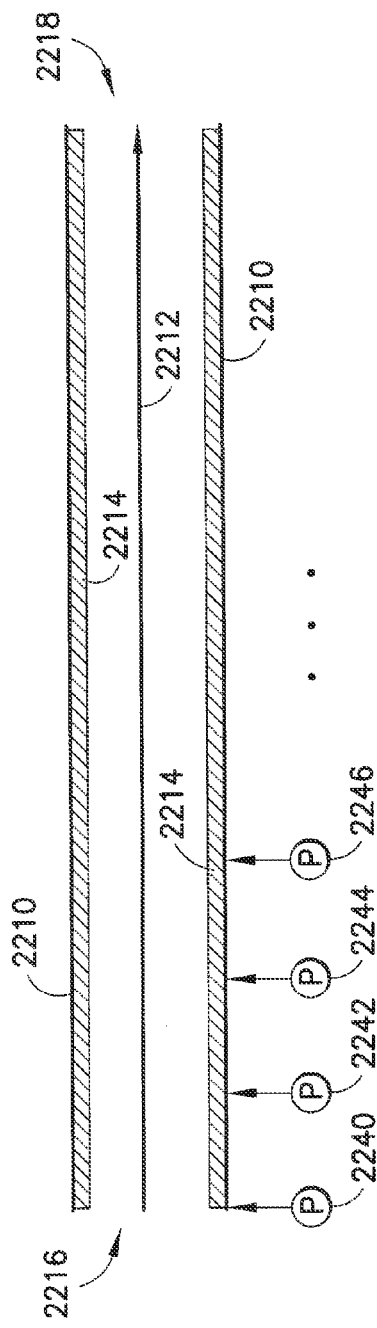
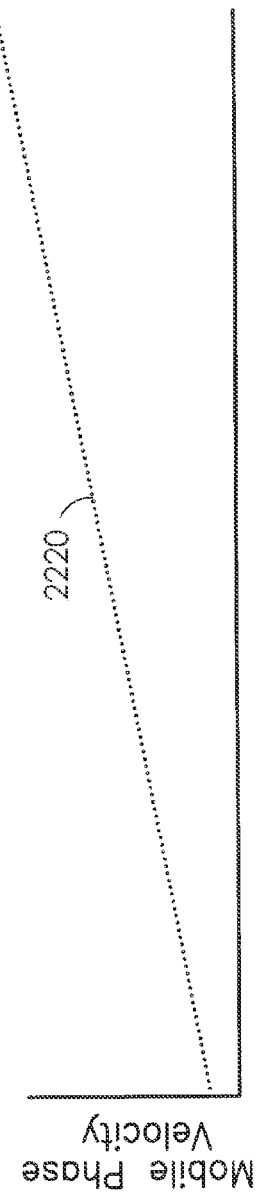
Fig. 22a
Fig. 22b

DIFFERENTIAL ACCELERATION CHROMATOGRAPHY

The present application is a divisional of U.S. application Ser. No. 11/949,362, filed on Dec. 3, 2007, and is hereby incorporated by reference in its entirety.

BACKGROUND OF THE INVENTION

1. Field of the Invention

This patent specification relates to chromatography. More particularly, this patent specification relates to systems and methods for separations of compounds during chromatographic analysis.

2. Background of the Invention

Chromatography is an area of analytical chemistry focused on the separation of complex mixtures of gases, liquids, and/or solids in an attempt to analyze the sample by identifying and/or quantifying various components of the mixture. Chromatography is classically performed with columns of fixed geometry, either in an open tubular or packed design. A stationary phase is deposited on the inner surfaces of the column, either on the inside walls in the case of the open tubular design, or on the packed particles for a packed design. In some cases the packed particles and stationary phase are one and the same. Such configurations are usually packaged as tubes that can be connected in various ways to chromatographic equipment.

Traditional chromatographic separations are accomplished through differential migration. The partitioning of analyte species between a mobile phase and a stationary phase results in each analyte band migrating along the separation column at a unique velocity that is less than that of the mobile phase. This velocity is determined by the magnitude of the partition coefficient, the phase ratio (ratio of volumes of stationary and mobile phases), and the velocity of the mobile phase (unretained species). The time spent in the mobile phase determines the degree to which analytes are retained. Although these factors can change slightly down the length of the column due to a variety of factors, band velocity is conventionally considered to be relatively constant throughout a separation under isothermal conditions with a constant flow rate and composition of mobile phase. As a result of differential migration, bands of analytes can be physically separated as long as the rates of differential migration vary by a large-enough factor.

However, there remains a general problem with conventional chromatography approaches due to a phenomenon known as band broadening. Band broadening is the tendency for bands on a chromatographic column to continuously grow longer due to a variety of sources which are primarily related to diffusion. In general, longitudinal diffusion is a dominating factor, and is proportional to the square-root of time spent on the column. Since differential migration results in a linear increase in band-to-band distances (measured center to center) as a function of time, and band broadening decreases the band-to-band distance (measured edge to edge) with the square-root of time, the chromatographic resolution is usually generalized to be proportional to the square-root of time spent on the column. FIGS. 1a-1d illustrate the effects of differential migration and broadening on chromatographic resolution, according to conventional chromatography techniques. FIG. 1a shows two components, "A" and "B," in FIGS. 1a-c for simulated uniformly wall-coated tubular column having infinite length. FIG. 1a is a band trajectory plot where the differential migration is apparent. FIG. 1b shows band broadening as a function of time. FIG. 1c shows velocity as a function of time. FIG. 1d shows the calculated resolution between bands A and B as a function of time. In FIG. 1d, chromatographic resolution is calculated for each "vertical slice" of the plots in figure A, that is the difference in band position divided by the average band width. Note that this measure of resolution is not the same as that typically observed on a chromatographic system with a column of finite-length and a detector that is after the column. The type of separation illustrated in FIGS. 1a-d is essentially a situation of "diminishing returns" where the chromatographer can not improve the chromatographic resolution in a time-effective manner by using a longer column. In an effort to improve band separations in a more time-effective manner, conventional chromatographic techniques have focused on optimizing column diameters, mobile phase flow rates, stationary phase functionality and thickness, and other factors.

SUMMARY OF THE INVENTION

According to an embodiment of the invention, the invention can improve component or compound separations in chromatography through novel techniques. According to embodiments, a system is provided for chromatographic analysis of a sample containing at least a first compound or component and a second compound of component. As used herein the terms analyte(s), compound(s) and component(s) refer to any separable components of a mixture. The system includes a column containing a stationary phase. The first and second components enter the column simultaneously at an inlet, flow through the column, and exit the column at an outlet. A source of a mobile phase is in fluid communication with the column such that the mobile phase can flow through the column thereby carrying the first and second components through the column from the inlet to the outlet. The first and second components when flowing through the column from the inlet to the outlet have first and second accelerations respectively, and the first acceleration being substantially different from the second acceleration.

A method is also provided, according to embodiments, for separating a first component and a second component. The first and second components simultaneously introduced into a stationary phase containing column at an inlet. A mobile phase is introduced into the column such that the first and second components are carried by the mobile phase through the column towards an outlet of the column. The first and second components when flowing through the column from the inlet to the outlet have first and second accelerations respectively, and the first acceleration being substantially different from the second acceleration.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 13 shows an example of a column having an insert, according to embodiments;

FIGS. 14a-14b shows an example of insert in a chromatographic column, according to embodiments;

FIGS. 22a-22b show a column of a chromatographic system having a pressure gradient, according to embodiments.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

According to an embodiment of the invention, the invention can be a system including a column containing a stationary phase. Further, first and second components enter the column simultaneously at an inlet, flow through the column, and exit the column at an outlet. A source of a mobile phase is in fluid communication with the column such that the mobile phase can flow through the column thereby carrying the first and second components through the column from the inlet to the outlet. The first and second components when flowing through the column from the inlet to the outlet have first and second accelerations respectively, and the first acceleration being substantially different from the second acceleration.

Figure 1A:
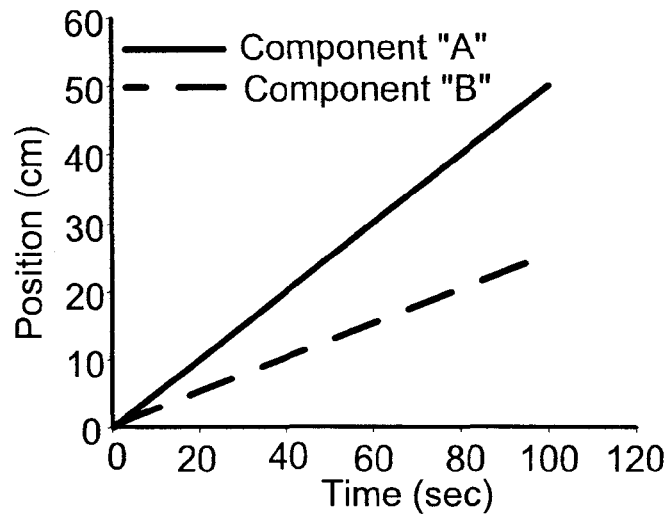
FIGS. 1a-1d illustrate the effect of band broadening on chromatographic resolution, according to conventional chromatography techniques.
Figure 1B:
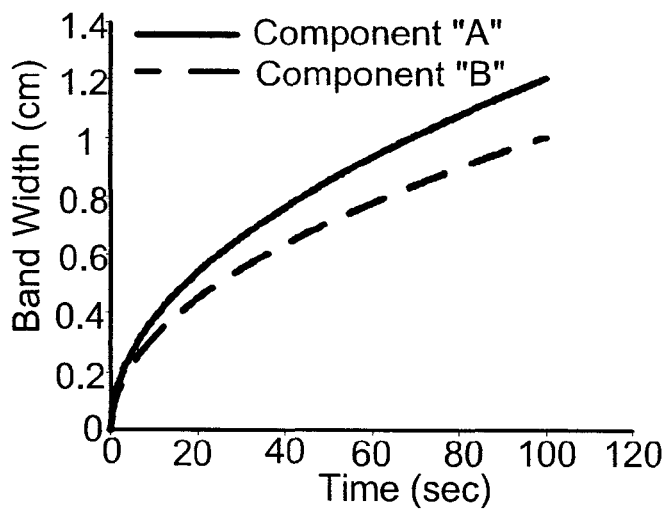
Figure 1C:
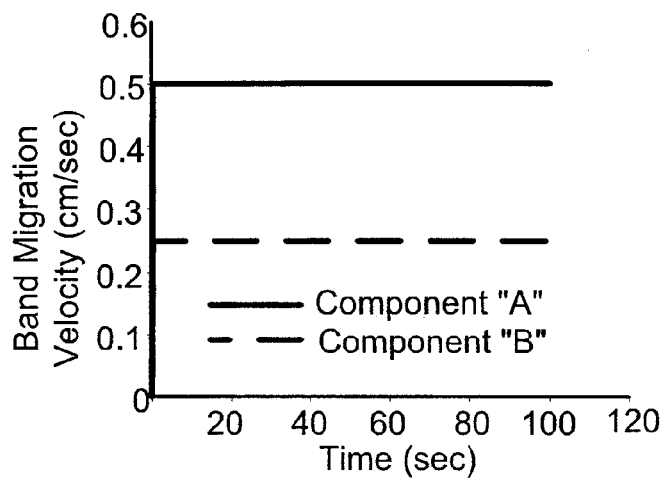
Figure 1D:
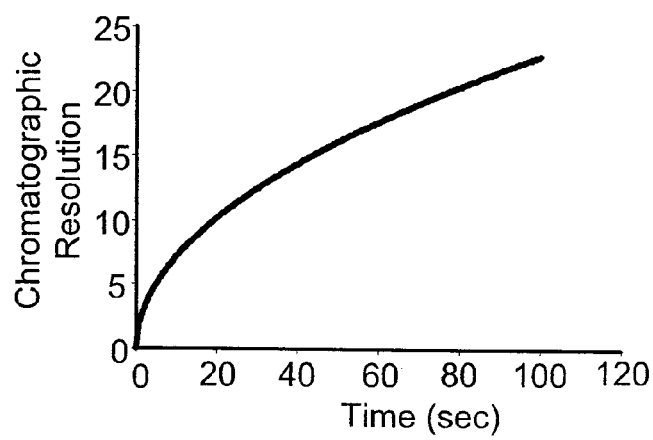
Figure 2A:
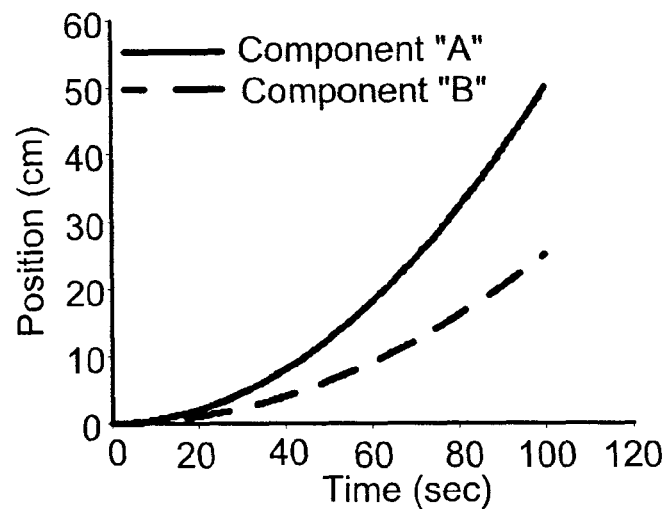
FIGS. 2a-d illustrate the effect of differential acceleration according to embodiments.
Figure 2B:
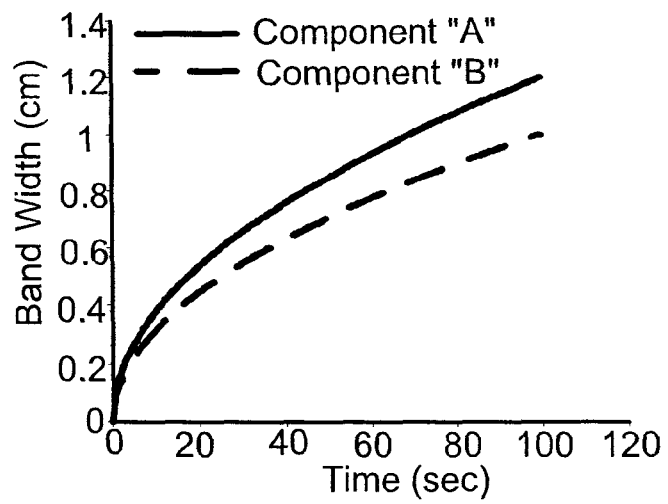
Figure 2C:
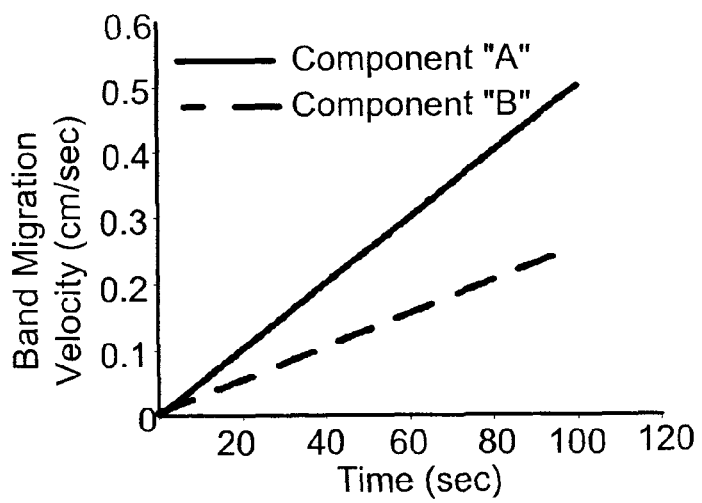
Figure 2D:
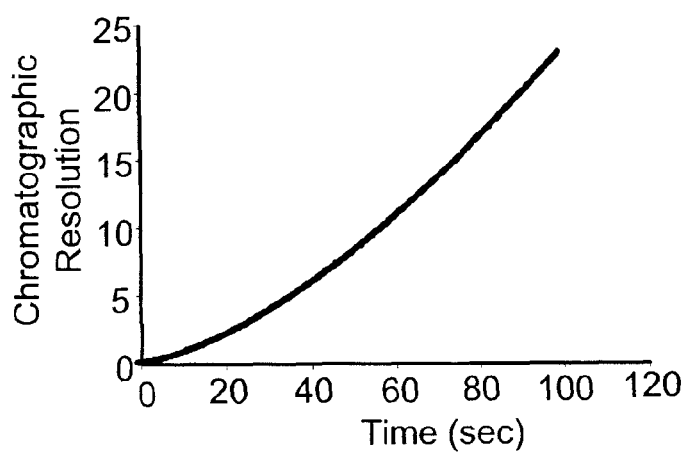

According to various embodiments, methods and systems are provided for improving chromatographic separation based on differential acceleration. As a consequence, band migration will be accelerated as a function of length on the column to more-effectively increase band-to-band distances. FIGS. 2a-d illustrate the effect of differential acceleration according to embodiments. FIG. 2a-d show a scenario in a similar fashion to that of FIGS. 1a-d, although in FIGS. 2a-d the band velocity increases linearly with time (i.e. length of the column), as shown by FIGS. 2a and 2c. As in FIG. 1b, the band-broadening shown in FIG. 2b still increases with the square-root of time. Since the band-to-band distance increases with the square of time, while band-broadening occurs with the square-root of time, the chromatographic resolution increases with $(time)^{1.5}$, as is shown in FIG. 2d. This is a significant difference as a longer separation column is a benefit under the scenario of FIGS. 2a-d. Importantly, the calculated separations shown in FIGS. 1d and 2d were designed specifically such that in both cases, components A and B would be in the same position at 100 seconds, and therefore have identical resolutions at that point.

Figure 3A:
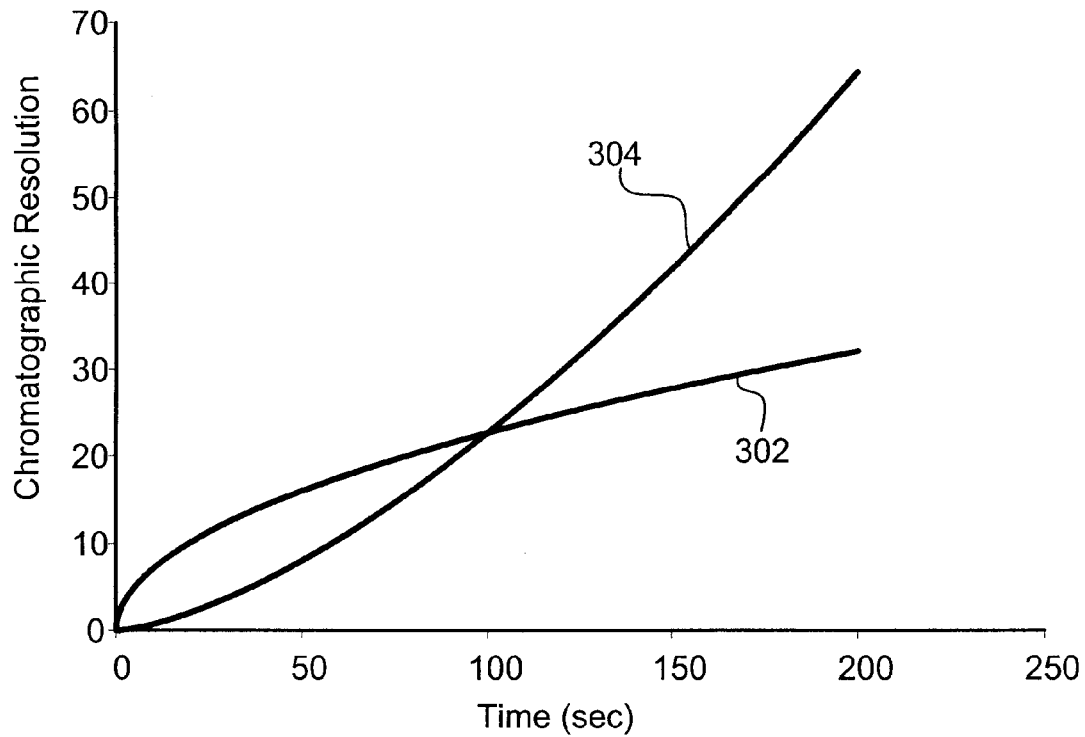
FIGS. 3a-3b illustrate the benefits of separations by differential acceleration according to embodiments.
Figure 3B:
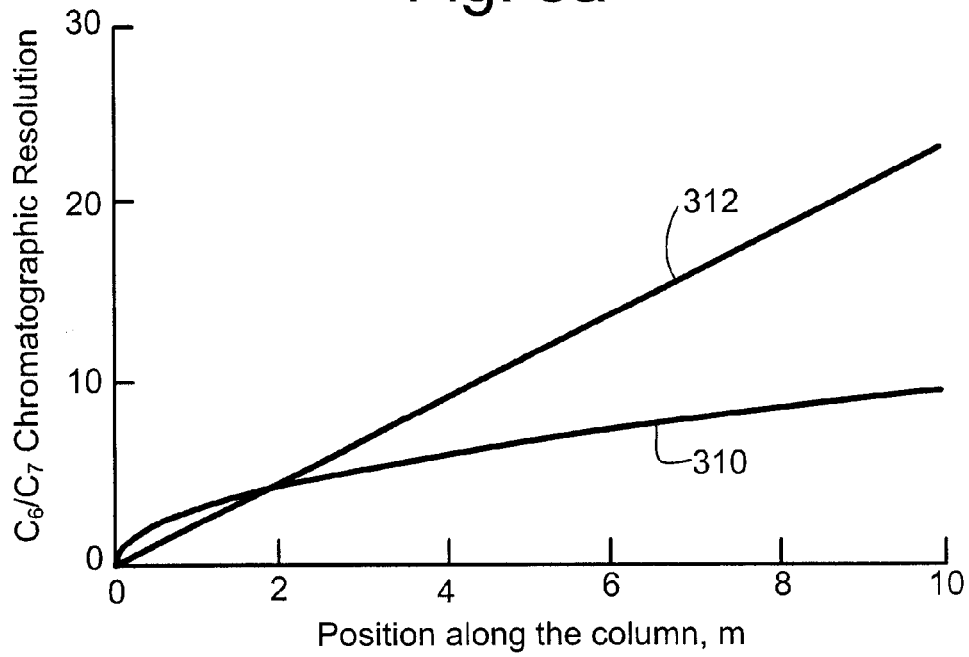

FIGS. 3a-3b illustrate the benefits of separations by differential acceleration according to embodiments. FIG. 3a shows the plots of chromatographic resolution versus time for the scenarios in FIGS. 1a-1d and FIGS. 2a-2d where the time axis is extended to 200 seconds. The curve 302 shows the chromatographic resolution under in the conventional differential migration scenario of FIGS. 1a-1d, and curve 304 shows the chromatographic resolution under the differential-acceleration based separation of FIGS. 2a-2d. From FIG. 3a is it clear that the true benefit from differential acceleration is seen in the final 100 seconds of the plot. FIG. 3b shows modelled resolution of a $C_6/C_7$ pair as a function of the column length. Curve 310 is a case where the column radius is kept constant throughout the length as in conventional chromatography. Curve 312 is a case where the column radius is linearly increased along the length of the column from inlet to outlet, according to embodiments that are discussed in further detail herein. As can be seen from FIG. 3b, the resolution curve 312 is not proportional to the square root of the column length. The interception of curves 310 and 312 occurs at about 1.8 m. With the modeled column profiles shown in FIG. 3b, a decrease in the length of the column is provided by the linearly increasing column radius while maintaining the resolution value when compared to a conventional constant radius column.

Several techniques are proposed herein to achieve differential acceleration of two or more analytes. Variable geometry columns (VGC) are provided for chromatography (for example, gas chromatography (GC)). A VGC column features a variable cross-section and may also feature a variable distribution of stationary phase along the length of the column. This applicable to both open tubular columns (OTCs) and packed columns (PCs). The variations in cross-section include changes in cross-sectional shape, aspect ratio, and/or average internal radius. The variations in stationary phase distribution include variation in thickness and/or uniformity for the case of OTCs and variation of particle size and/or film thickness for PCs. Additionally, the variable stationary phase composition (VSPC) is also provided. With VSPC, a change in chemical composition, functionality, and/or physical properties such as density, porosity, viscosity, and diffusivity, as a function of column length is provided.

In order to make a single column more applicable to a wide range of compounds, and to minimize experiment times, temperature programming, flow programming, and gradient elution are often employed. These parameters affect the degree of interaction between analyte molecules and the stationary phase (retention) and the tendency of the analyte band to broaden (band broadening). The combined extent of these two factors determines the efficiency of the separation. It has been found that modifying column geometry and/or stationary phase composition, as defined above, as a function of length can achieve effects that are similar to temperature programming, flow programming, and gradient elution, as well as create a number of new effects that have not been previously possible.

Several advantages are potentially afforded by the embodiments described herein. For example, a gradual change in column cross-section and film thickness along the length of the column may allow for smaller temperature programming ranges for a given range of analyte volatilities. Similarly, it is possible to reduce analysis times while still achieving similar chromatographic resolution of limiting compounds (compounds that, by virtue of their partition coefficient with a given stationary phase, limit the temperature range and/or analysis time that is required to achieve a given level of separation or chromatographic resolution). An alternative use of this design would be to enhance the separation quality for specific volatility ranges while allowing minimal long-term contamination by other volatility ranges and perhaps possible interference (i.e. co-elution) from specific compounds.

Other advantages may be realized in the form of the pressure restriction created by the column. Since most GC is performed in a regime where gases are compressible, average linear velocities (and velocity distributions) along the length of a GC column may vary considerably. As the average linear velocity varies, the efficiency of the column will vary, because the rate of analyte interaction with the stationary phase will vary (e.g. perpendicular diffusion will vary). By varying the cross-section of the column as a function of length, it is possible to control the pressure restriction as a function of length, and thus control the carrier gas compression. Several possibilities arise from this notion: firstly, the ability to achieve improved chromatographic resolution without a significant increase in pressure restriction is possible; alternatively, intentionally causing excess carrier gas compression or decompression at specific sections of the column may allow for great improvements in the quality of separation by according to the average carrier gas pressure (e.g. diffusion coefficient, viscosity, partition coefficient, etc).

The variation of film composition, functionality, or physical properties presents additional potential advantages. By gradually transitioning between two types of stationary phases, rather than having different types of columns in series, more advanced separation strategies may be possible. By gradually changing stationary phase density as a function of length, it may be possible to control subtle features of the separation by changing the rate of diffusion or the partition coefficient of eluting compounds.

An additional enhancement to chromatographic separations is the generation of turbulence within the flow path due to the shape of the fluidic channel, a material packed or deposited within the channel, or the texture of the surface within the channel. A variety of controlled textures are possible within a microfabricated fluidic channel. Such efforts may provide increased chromatographic resolution by increasing the rate of perpendicular diffusion Various embodiments are provided herein than create differential acceleration. They are generally or directly related to decreasing band retention as a function of length down the column. Some examples include decreasing stationary phase thickness, increasing column diameter (for wall-coated open-tubular columns), increasing particle size (for packed columns), decreasing partition coefficients by a change in stationary and/or mobile phase composition, increasing column temperature, or varying mobile phase pressure as a function of column length.

Additional facets of chromatographic improvement are also possible when configuring a system for a differential acceleration-based separation. For example, by expanding the cross section of the column to reduce band retention, a focusing of bands is possible—a band of a given volume will occupy less length in a larger diameter tube than in a smaller one. This focusing can yield additional chromatographic resolution in addition to the differential acceleration. An alternative use of this type of focusing would be in a column design that yields high resolution in a short amount of time, yet does not require as sharp an injection as other High-Speed Chromatography scenarios. Enhancing temperature programming for Gas Chromatography is also possible; since the acceleration effect works similarly to temperature programming in some ways, it can potentially reduce the range of temperatures required for temperature programming of a given sample mixture, or conversely, extend the range of sample volatility than can be analyzed for a given temperature range. Similarly, the gradient elution in High Performance Liquid Chromatography can be enhanced.

According to certain embodiments, MEMS manufacturing technology is used for chromatography columns having a modulated column profile. There are several ways to achieve column profile modulation by employing different MEMS technologies. A simple implementation is a 2D layout modification of the column width on a silicon on insulator (SOI) wafer. In case of rectangular column section, the column depth remains the same along the length. A modulation in column width is analogous to a modulation in the effective column radius. This approach has an advantage of not require additional masking steps.

According to another embodiment, the column radius could also be modified by adjusting the column depth in function of the length. This can be accomplished, for example by isotropically etching the column in a glass or silicon wafer, where the wet etching is controlled to yield 3D modulation of the column cross-section. Depending on the desired nonlinearity of the cross-section changes, the mask layout and etching parameters should to be fine-tuned in order to fabricate smooth column profiles.

A model used to evaluate various embodiments will now be described. The functions used to describe profiles of the column radius and the stationary phase thickness along the column length are presented in the following form:

$$R_{column} = f(x)$$

$$d_f = f(x)$$

where x is a distance from column beginning, $R_{column}$ is the effective column radius, $d_f$ is the stationary phase thickness that were investigated are vary from linear to significantly non-linear. The following profiles of the column radius modulation were evaluated:

1. $R_{column}(x) = R_{column0} + x^{0.01} \cdot \left( \frac{R_{column_{final}} - R_{column_{initial}}}{L_{column}^{0.01}} \right);$ 2. $R_{column}(x) = R_{column0} + x^{0.5} \cdot \left( \frac{R_{column_{final}} - R_{column_{initial}}}{L_{column}^{0.5}} \right);$ 3. $R_{column}(x) = R_{column0} + x \cdot \left( \frac{R_{column_{final}} - R_{column_{initial}}}{L_{column}} \right);$ 4. $R_{column}(x) = R_{column0} + \exp\left\{ \frac{x}{L_{column}} \cdot \ln\left( \frac{R_{column_{final}}}{R_{column_{initial}}} \right) \right\};$ 5. $R_{column}(x) = R_{column0} + x^2 \cdot \left( \frac{R_{column_{final}} - R_{column_{initial}}}{L_{column}^2} \right);$ 6. $R_{column}(x) = R_{column0} + x^3 \cdot \left( \frac{R_{column_{final}} - R_{column_{initial}}}{L_{column}^3} \right);$ 7. $R_{column}(x) = R_{column0} + x^4 \cdot \left( \frac{R_{column_{final}} - R_{column_{initial}}}{L_{column}^4} \right);$ 8. $R_{column}(x) = R_{column0} + x^{100} \cdot \left( \frac{R_{column_{final}} - R_{column_{initial}}}{L_{column}^{100}} \right).$ Profiles of the stationary phase thickness along the column that were evaluated are described by following equations:

1. $d_f(x) = d_{f_0} + x^{0.01} \cdot \left( \frac{d_{f_{final}} - d_{f_{initial}}}{L_{column}^{0.01}} \right);$ 2. $d_f(x) = d_{f_0} + x^{0.5} \cdot \left( \frac{d_{f_{final}} - d_{f_{initial}}}{L_{column}^{0.5}} \right);$ 3. $d_f(x) = d_{f_0} + \exp \cdot \left\{ \frac{x}{L_{column}} \cdot \ln\left( \frac{d_{f_{final}}}{d_{f_{initial}}} \right) \right\};$ 4. $d_f(x) = d_{f_0} + x \cdot \left( \frac{d_{f_{final}} - d_{f_{initial}}}{L_{column}} \right);$ 5. $d_f(x) = d_{f_0} + x^2 \cdot \left( \frac{d_{f_{final}} - d_{f_{initial}}}{L_{column}^2} \right);$ -continued 6. $d_f(x) = d_{f_0} + x^3 \cdot \left(\dfrac{d_{f_{final}} - d_{f_{initial}}}{L^3_{column}}\right);$ 7. $d_f(x) = d_{f_0} + x^{10} \cdot \left(\dfrac{d_{f_{final}} - d_{f_{initial}}}{L^{10}_{column}}\right);$ 8. $d_f(x) = d_{f_0} + x^{100} \cdot \left(\dfrac{d_{f_{final}} - d_{f_{initial}}}{L^{100}_{column}}\right).$ The principles of the computational algorithm used for evaluation was taken from H. Snijder, H. Janssen, C. Cramers, *Optimization of temperature-programmed gas chromatographic separation*, Journal of Chromatography A, 718 (1995), 339-355, incorporated herein by reference. It is possible to compute the distance which an analyte band flows during finite and very small time interval $\Delta t$, knowing the band velocity and partition coefficient value:

$$\Delta L_i = \frac{\Delta t \cdot v_i}{1 + k_i},$$

where $k_i$ is the distribution coefficient that is determined from the partition coefficient:

$$k_i = \frac{\exp\left\{\dfrac{A}{T_i} - B\right\}}{\dfrac{(R_{column_i} - d_{f_i})^2}{d_{f_i} \cdot (2 \cdot R_{column_f} - d_{f_i})}},$$

where A and B are the effective thermodynamic constants, specific for the specific component.

The band velocity, the partition coefficient, the gas viscosity, and the band broadening gradient along the column will be nonlinear and these parameters are computed for the every finite column element. The set of equations that is used to estimate column performance is presented below.

$$v_i = \frac{v_0}{p_i} \cdot \frac{\eta_{He_0}}{\eta_{He_i}} \cdot \frac{R^2_{column_i}}{R^2_{column_0}},$$

$$v_0 = \frac{R^2_{column} \cdot p_{out}}{16 \cdot \eta_{He}(T, p) \cdot L_{column}} \cdot (\gamma^2 - 1),$$

To compute pressure correction factor $p_i$ it is necessary to compute pressure the profile along the column. The pressure profile along the column can be computed from D'Arcy's law:

$$v = -\frac{Kp}{\eta} \cdot \frac{dp}{dx},$$

where Kp is the permeability, $\eta$ is the viscosity; and knowing invariant $p(x) \cdot S(x) \cdot v(x)$, where $S(x)$ is the column area.

$$p_i = \sqrt{\gamma^2 - \frac{F_x}{F_L} \cdot (\gamma^2 - 1)},$$

where $$F_x = \int_0^x \frac{dx}{S(x)}$$

$$F_L = \int_0^{L_{column}} \frac{dx}{S(x)}.$$

In the case of a linear variation of the column radius, this leads to the following equation:

$$p_i = \sqrt{\gamma^2 - \frac{R_f \cdot x_i}{L_{column} \cdot \left(R_0 + \dfrac{R_f - R_0}{L_{column}} \cdot x_i\right)} \cdot (\gamma^2 - 1)},$$

$$\eta_{He_i} \cong 20 \cdot \left(\frac{T}{300}\right)^{0.67742} + (3.148 - 3.075 \cdot 10^{-3} \cdot T) \cdot 10^{-3} \cdot p \; [\mu Pa \cdot sec],$$

where $\gamma$ is the inlet/outlet pressure ratio, and $\eta_{He}$, is the helium viscosity, $p_{out}$ is the outlet pressure, T—is the column temperature, and index 0 means that the parameter is computed for the column beginning conditions, index i means that parameter is computed for the i-finite column element.

Figure 4:
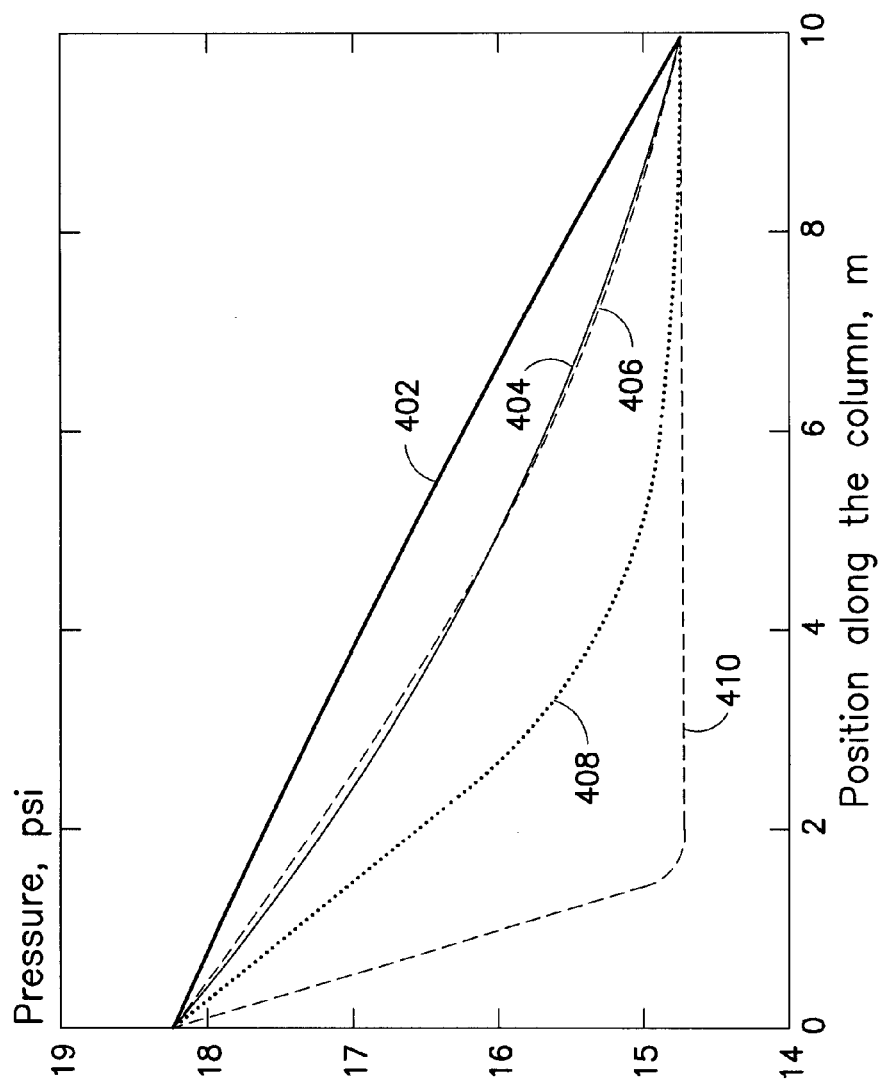
FIG. 4 illustrates various estimated pressure profiles different column geometries, according to embodiments.

FIG. 4 illustrates various estimated pressure profiles different column geometries, according to embodiments. Curve 402 is the profile for a constant radius, curve 404 for a linear profile, curve 406 for a quadratic profile, curve 408 for cubic profile, and curve 410 for the case of $R(x) \sim x^{10}$. From FIG. 4 it is evident that pressure profiles change significantly going from column with constant column radius to the columns with variable geometry.

Figure 5:
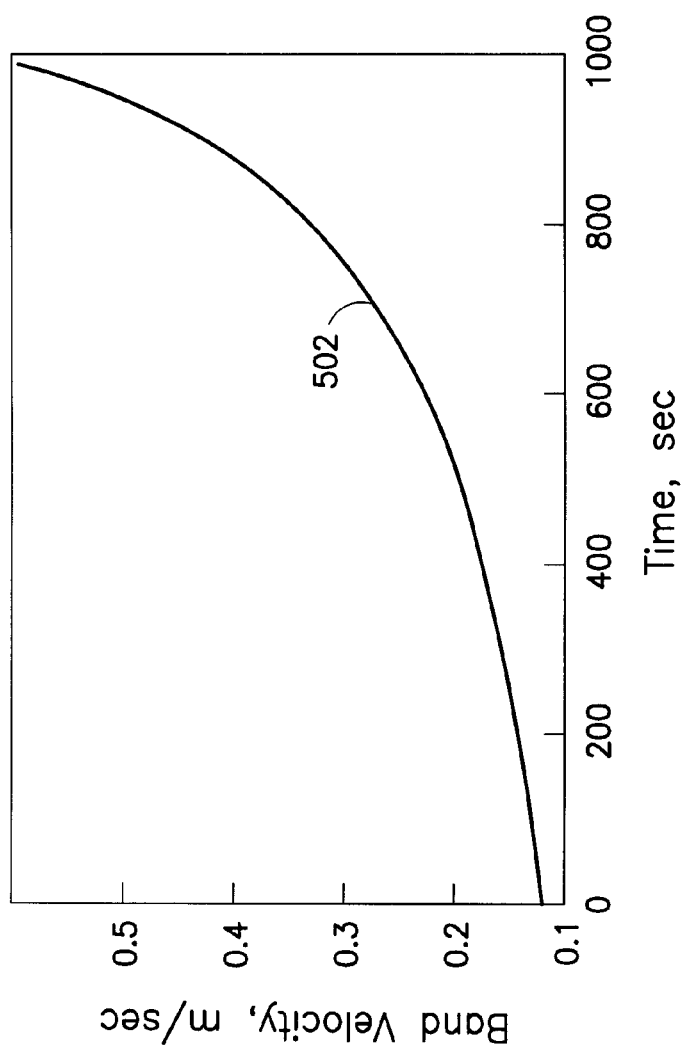
FIG. 5 illustrates and example of band velocity for an analyte according to embodiments.

FIG. 5 illustrates and example of band velocity for an analyte according to embodiments. Curve 502 is the band velocity along a column for an example analyte, n-$C_7$, at an initial temperature of 273 K. In calculating curve 502, there was no temperature programming, an initial column radius is 90 µm and final column radius of 180 µm, and stationary phase thickness of 2 µm was assumed to be constant along the length of the column.

When the band reaches the end of the column, the sum of finite time intervals will determine the retention time of the component. The peak width can be evaluated from mass-transfer equations:

$$\begin{cases} \dfrac{\partial N_m}{\partial t} + v_g \cdot \dfrac{\partial N_m}{\partial x} - D_m \cdot \dfrac{\partial^2 N_m}{\partial x^2} + k_f \cdot (K \cdot N_m - N_{st} |_{z = d_f}) = 0 \\ \dfrac{\partial N_{st}}{\partial t} - D_{st} \cdot \dfrac{\partial^2 N_{st}}{\partial z^2} = 0, \end{cases}$$

where $N_{m,st}$ are the concentrations of the mobile and stationary phases, $D_{m,st}$ are the diffusion coefficients for the mobile and stationary phases, K is the partition coefficient, $v_g$ is the average carrier gas velocity, and $k_f$ is the mass-transfer coefficient across the boundary of stationary phase.

Knowing the first and the second moments of the concentration profile it is possible to evaluate the peak variance and derive the equation that describes the incremental change in variance per unit column length:

$$H_i = \frac{L_{column} \cdot m_2}{m_1^2}$$

-continued $$= \frac{2 \cdot D_{m_i} \cdot j_1}{v_i} + \frac{1 + 6 \cdot k_i + 11 \cdot k_i^2}{24 \cdot (1 + k_i)^2} \cdot \frac{R_{column_i}^2}{D_{m_i}} \cdot$$

$$v_i \cdot j_1 + \frac{2}{3} \cdot \frac{k_i}{(1 + k_i)^2} \cdot \frac{d_{f_i}^2}{D_{st_i}} \cdot v_i \cdot j_2,$$

where $j_1$ and $j_2$ are compressibility factors $$j_1 = \frac{9}{8} \cdot \frac{(\gamma^2 - 1) \cdot (\gamma^4 - 1)}{(\gamma^3 - 1)^2};$$

-continued $$j_2 = \frac{3}{2} \cdot \frac{(\gamma^2 - 1)}{(\gamma^3 - 1)},$$

and $m_{2,1}$ are the first and second moment of the concentration peak, correspondingly.

When the plate height $H_i$ is computed it is possible to estimate the peak width based on next equation:

$$\sigma_{peak\text{-}Time} = \frac{\sqrt{\sum_i H_i \cdot \Delta L_i}}{v_{i_{last}}} \cdot (1 + k_{i_{last}}).$$

From computation performed for n-$C_6$/$C_7$ and n-$C_{12}$/$C_{14}$, it has been found that to improve peak resolution, stationary phase thickness should decrease towards the end of the column. The effect of column radius modulation and the effect of stationary phase thickness modulation are not necessarily additive and thus it is useful to evaluate their influences at the same time.

The quantitative data for some scenarios are presented in Table 1 below. For the data shown in Table 1, the computation was performed for a column with a polydimethyl siloxane (PDMS) stationary phase, 10 m length, column radius beginning with 90 μm in and ending with 180 μm, a stationary phase thickness in the column beginning at 2 μm, and ending at 1 μm, the temperature gradient was 1 deg/sec, the three initial temperatures were—273 K, 373 K, 473 K; the first case is an experiment when all parameters are fixed, the second—temperature programmed gas chromatography (TPGC), the third—the column radius changes, the fourth—the column radius changes and at the same time the stationary phase thickness changes; the fifth—the column radius changes and at the same time the stationary phase thickness change for TPGC.

It has been found that it is not necessary to combine temperature programming and column profile modulation; column profile modulation can improve chromatographic analysis performance alone. It has also been found that the column profile modulation indeed can significantly decrease the time of experiments and do this while improving the peaks resolution compared to TPGC approach.

TABLE 1

| Condition | $t_{ret}$, n-$C_6$, sec | $t_{ret}$, n-$C_7$, sec | $w_{hh}$, n-$C_6$, sec | $w_{hh}$, n-$C_7$, sec | R |
|---|---|---|---|---|---|
| $T_{initial}$ = 273 K | | | | | |
| const | 917.0 | 2535 | 12.27 | 33.719 | 41.402 |
| TPGC | 185.6 | 219 | 2.496 | 2.924 | 7.266 |
| R | 363.0 | 986 | 1.772 | 4.170 | 123.385 |
| R + $d_f$ | 310.0 | 833 | 0.911 | 2.125 | 203.941 |
| R + $d_f$ + TPGC | 108.4 | 137.6 | 0.37 | 0.423 | 43.325 |
| $T_{initial}$ = 373 K | | | | | |
| const | 158.0 | 218 | 3.018 | 4.323 | 9.663 |
| TPGC | 131.5 | 146.8 | 2.841 | 3.165 | 2.994 |
| R | 72.8 | 96.0 | 0.507 | 0.663 | 23.378 |
| R + $d_f$ | 68.8 | 88.3 | 0.395 | 0.474 | 26.382 |
| R + $d_f$ + TPGC | 64.5 | 74 | 0.416 | 0.459 | 12.815 |
| $T_{initial}$ = 473 K | | | | | |
| const | 125.3 | 133.3 | 3.034 | 3.372 | 1.468 |
| TPGC | 128.6 | 132.3 | 3.795 | 4.029 | 0.554 |
| R | 62.2 | 65.3 | 0.523 | 0.568 | 3.319 |
| R + $d_f$ | 61.3 | 63.9 | 0.496 | 0.528 | 2.966 |
| R + $d_f$ + TPGC | 62.7 | 64.5 | 0.571 | 0.602 | 1.835 |

In selecting a suitable column profile the evaluation parameter should first be established. Examples of different evaluation parameters that can be optimized are: maximize the peak resolutions, minimize the experimental time (retention time), and maximize the peak resolutions over time parameter (PRoT).

The results of the numerical experiments that were performed to evaluate how resolution and retention time depends on the geometry modulation are summarized in Table 2.

TABLE 2

| | $T_{initial}$ = 273 K | | | | | |
|---|---|---|---|---|---|---|
| Profiles ($R_{column}$/$d_f$) | $t_{ret}$, n-$C_6$, sec | $t_{ret}$, n-$C_7$, sec | $w_{hh}$, n-$C_6$, sec | $w_{hh}$, n-$C_7$, sec | R | R/$t_{retC7}$ |
| (3/const) | 363 | 986 | 1.772 | 4.17 | 123.385 | 0.1254 |
| (3/4) | 310 | 833 | 0.9 | 2.1 | 204.2 | 0.2451 |
| (5/const) | 521.37 | 1428 | 1.726 | 4.092 | 183.407 | 0.1284 |
| (5/4) | 441.83 | 1195 | 0.915 | 2.074 | 296.657 | 0.2482 |
| (6/const) | 612.68 | 1683 | 1.711 | 4.085 | 217.361 | 0.1292 |
| (6/4) | 512.46 | 1390 | 0.919 | 2.084 | 343.99 | 0.2475 |
| (7/const) | 670.6 | 1845 | 1.705 | 4.087 | 238.645 | 0.1293 |
| (7/4) | 554.95 | 1507 | 0.924 | 2.093 | 371.35 | 0.2464 |
| (8/const) | 904.74 | 2500 | 1.702 | 4.138 | 321.52 | 0.1286 |
| (8/4) | 703.18 | 1911 | 0.954 | 2.167 | 455.4 | 0.2383 |
| (4/cost) | 405.92 | 1106 | 1.747 | 4.107 | 140.695 | 0.1272 |
| (4/4) | 346.1 | 930.66 | 0.914 | 2.068 | 230.8 | 0.248 |

TABLE 2-continued

| | $T_{initial}$ = 273 K | | | | | |
|---|---|---|---|---|---|---|
| Profiles ($R_{column}/d_f$) | $t_{ret}$, n-C$_6$, sec | $t_{ret}$, n-C$_7$, sec | $w_{hh}$, n-C$_6$, sec | $w_{hh}$, n-C$_7$, sec | R | R/$t_{retC7}$ |
| (8/8) | 903.34 | 2496 | 0.976 | 2.198 | 590.717 | 0.2367 |
| (1/1) | 71.81 | 173.02 | 0.975 | 2.376 | 35.56 | 0.2055 |
| (3/5) | 335.44 | 905.65 | 0.946 | 2.113 | 219.431 | 0.2423 |
| (3/6) | 344.98 | 933.53 | 0.961 | 2.127 | 224.398 | 0.2404 |
| (3/7) | 358.17 | 972.08 | 0.995 | 2.162 | 228.934 | 0.2355 |
| (3/3) | 302.07 | 808.11 | 0.914 | 2.08 | 189.916 | 0.2461 |
| (3/2) | 279.09 | 740.95 | 0.903 | 2.069 | 182.949 | 0.2469 |
| (3/1) | 201.51 | 514.22 | 0.871 | 2.037 | 126.58 | 0.2462 |

Based on these experimental results it has been found that to maximize the peaks resolution column radius profile should follow the function:

$$R_{column}(x) = R_{column0} + x^N \cdot \left(\frac{R_{column\,final} - R_{column\,initial}}{L_{column}^{100}}\right).$$

and stationary phase profile should follow the function:

$$d_f(x) = d_{f_0} + x^N \cdot \left(\frac{d_{f\,final} - d_{f\,initial}}{L_{column}^{100}}\right),$$

where N should be maximized.

At the same time to maximally reduce the time of the experiments another set of profiles should be used: the column radius profile should follow the function:

$$R_{column}(x) = R_{column0} + x^{1/N} \cdot \left(\frac{R_{column\,final} - R_{column\,initial}}{L_{column}^{0.01}}\right);$$

and stationary phase profile should follow the function:

$$d_f(x) = d_{f_0} + x^{1/N} \cdot \left(\frac{d_{f\,final} - d_{f\,initial}}{L_{column}^{100}}\right),$$

where N should be maximized.

Finally, in case of maximizing the PRoT parameter two profiles will have close to the optimum performance: the first one will have quadratic column radius profile and linear change in stationary phase thickness:

$$R_{column}(x) = R_{column0} + x^2 \cdot \left(\frac{R_{column\,final} - R_{column\,initial}}{L_{column}^2}\right);$$

$$d_f(x) = d_{f_0} + x \cdot \left(\frac{d_{f\,final} - d_{f\,initial}}{L_{column}}\right),$$

and the second one will have the exponential column radius profile and linear change in stationary phase thickness:

$$R_{column}(x) = R_{column0} + \exp\left\{\frac{x}{L_{column}} \cdot \ln\left(\frac{R_{column\,final}}{R_{column\,initial}}\right)\right\};$$

$$d_f(x) = d_{f_0} + x \cdot \left(\frac{d_{f\,final} - d_{f\,initial}}{L_{column}}\right).$$

The significance of modulated geometry in improving the performance of chromatographic analysis in case of heavier components has been evaluated. To the estimate modulated column performance in case of heavier components, an n-C$_{12}$/n-C$_{14}$ pair was selected.

From Table 3, it has been found that modulated geometry method improve performance of gas chromatography system more significantly for heavy components than for light ones.

TABLE 3

| Condition | $t_{ret}$, n-C$_{12}$, sec | $t_{ret}$, n-C$_{14}$, sec | $w_{hh}$, n-C$_{12}$, sec | $w_{hh}$, n-C$_{14}$, sec | R |
|---|---|---|---|---|---|
| | $T_{initial}$ = 373 K | | | | |
| const | 3135 | 15270 | 49.066 | 229.212 | 21.317 |
| R | 1220 | 5896 | 5.311 | 23.769 | 189.288 |
| R + d$_f$ | 1031 | 4951 | 2.714 | 11.855 | 316.766 |

The inlet/outlet pressure ratio optimization for C$_6$/C$_7$ and C$_{12}$/C$_{14}$ pairs is evaluated in the following discussion. The linearly modulated column was investigated and inlet/outlet pressure ratio influence trends were identified. It has been found that there is an optimum inlet/outlet pressure ratio from the resolution point of view but at the same time the parameters like PRoT will always increase with increasing inlet/outlet pressure ratio going to some saturation level. For the pairs C$_6$/C$_7$ and C$_{12}$/C$_{14}$ the optimum inlet/outlet pressure ratio is about 10-15 and the optimum inlet/outlet pressure ratio should be selected based on the results for the heaviest anticipated components because in a wide range of inlet/outlet pressures ratio resolution for the lighter components does not change significantly.

Figure 6A:
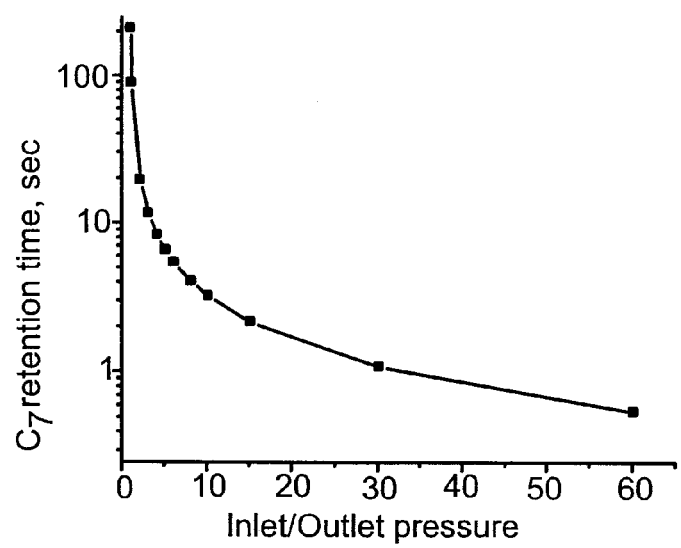
FIGS. 6a-6b illustrate the retention time for $C_7$ and outlet velocity as a function of inlet/outlet pressure ratio.
Figure 6B:
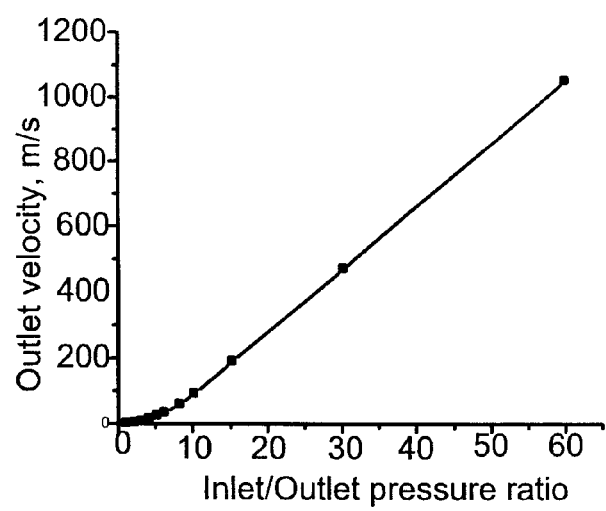
Figure 6C:
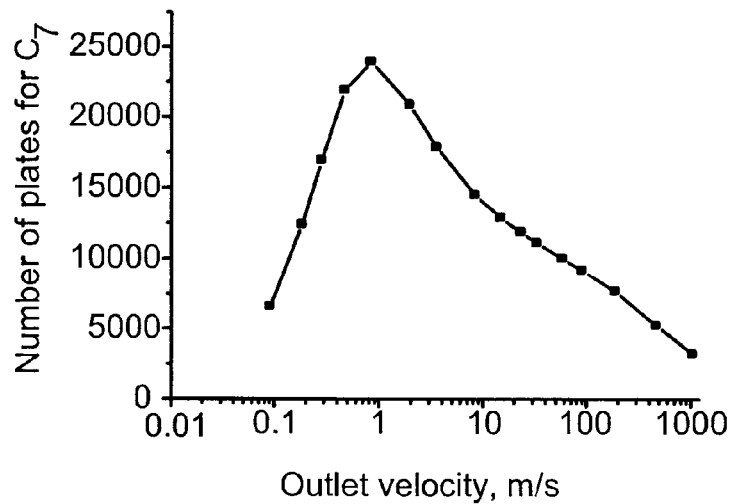
FIGS. 6c-6d illustrate the number of plates for $C_7$ and resolution of $C_6/C_7$ pair as a function of outlet velocity and inlet/outlet pressure ratio.
Figure 6D:
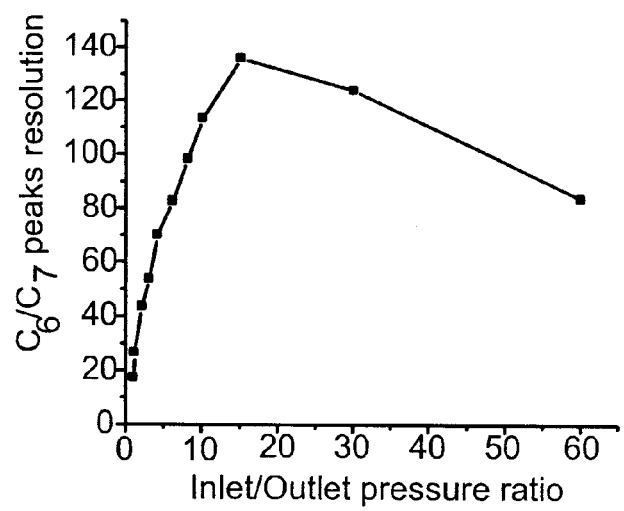
Figure 6E:
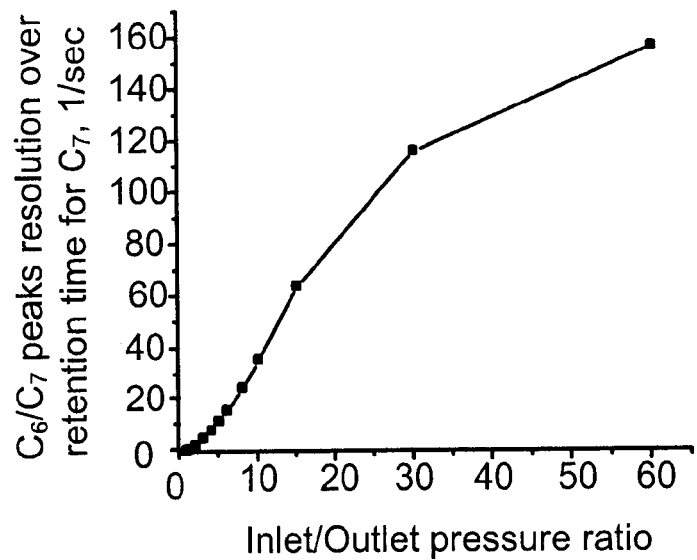
FIGS. 6e-6f illustrate the resolution of a $C_6/C_7$ pair over retention time for $C_7$ and peak width for $C_7$ as a function of inlet/outlet pressure ratio.
Figure 6F:
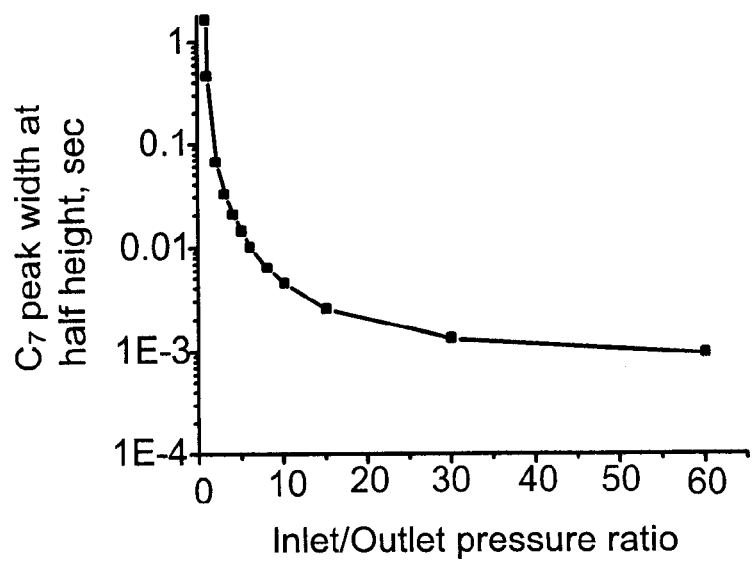

FIGS. 6a-6b illustrate the retention time for C$_7$ and outlet velocity as a function of inlet/outlet pressure ratio. FIGS. 6c-6d illustrate the number of plates for C$_7$ and resolution of C$_6$/C$_7$ pair as a function of outlet velocity and inlet/outlet pressure ratio. FIGS. 6e-6f illustrate the resolution of a C$_6$/C$_7$ pair over retention time for C$_7$ and peak width for C$_7$ as a function of inlet/outlet pressure ratio.

Figure 7A:
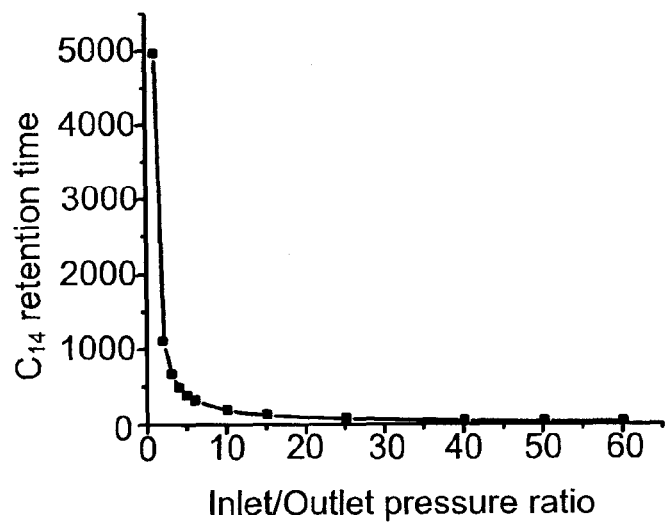
FIGS. 7a-7b illustrate the retention time for $C_{14}$ and resolution of $C_{12}/C_{14}$ pair as a function of inlet/outlet pressure ratio.
Figure 7B:
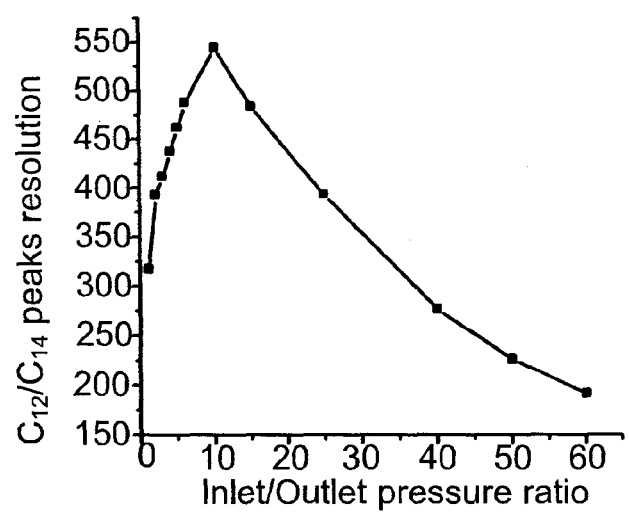
Figure 7C:
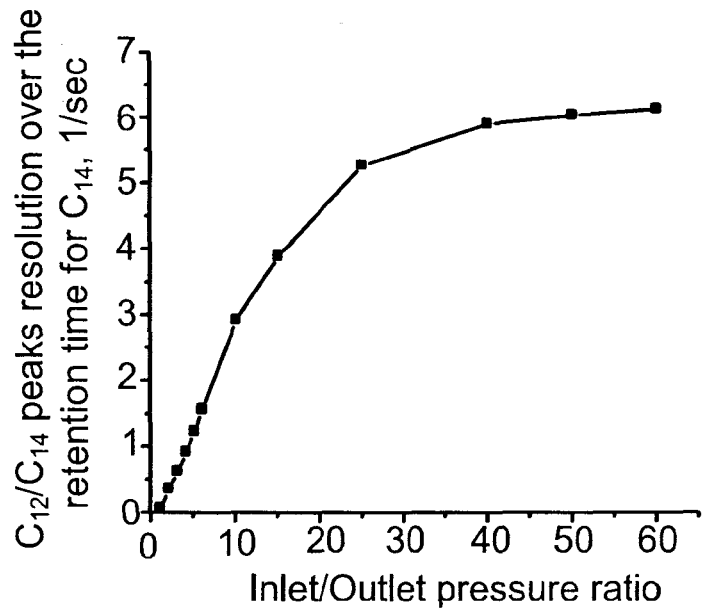
FIGS. 7c-7d illustrate the resolution of a $C_{12}/C_{14}$ pair over retention time for $C_{14}$ and peak width for $C_{14}$ as a function of inlet/outlet pressure ratio.
Figure 7D:
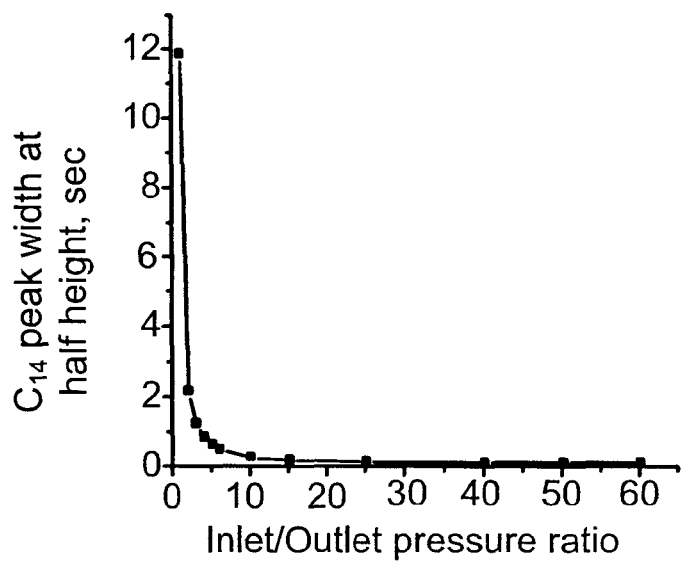

FIGS. 7a-7b illustrate the retention time for C$_{14}$ and resolution of C$_{12}$/C$_{14}$ pair as a function of inlet/outlet pressure ratio. FIGS. 7c-7d illustrate the resolution of a C$_{12}$/C$_{14}$ pair over retention time for C$_{14}$ and peak width for C$_{14}$ as a function of inlet/outlet pressure ratio.

In general, higher inlet/outlet pressure ratios will lead to a decrease in the component retention time. It has been found that this trend is true for the various situations: variations of the column inlet/outlet radius, the inlet/outlet stationary phase thickness. Because the components will stay in the column for the shorter period of time when the inlet/outlet pressure ratio increases, the peak width is also decreasing but the peak width decrease is more significant and this explains the peaks resolution increase at higher inlet/outlet pressure ratios. Note that as used herein, the terms "peaks resolution" and "chromatographic resolution" are used interchangeably an have the same meaning. Optimum values of the column inlet and outlet radius is shifting to the smaller range and in the case of infinitely high inlet/outlet pressure ratio will tend to be zero. At higher inlet/outlet pressure ratios the slope of the PRoT parameter is increasing and it is almost linear. In general, it has been found that at higher inlet/outlet pressure ratios there are no changes in the functional behavior and the findings for low inlet/outlet pressure ratios will remain the same. These trends have been found for the both $C_6/C_7$ and $C_{12}/C_{14}$ pairs.

Figure 8A:
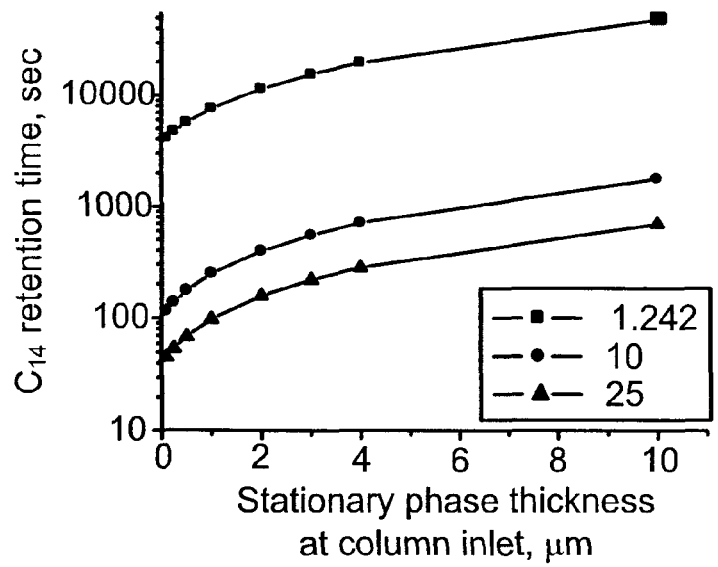
FIGS. 8a-8b illustrate $C_{14}$ retention time and resolution of $C_{12}/C_{14}$ as a function of the stationary phase thickness at the column inlet at different inlet/outlet pressure ratio.
Figure 8B:
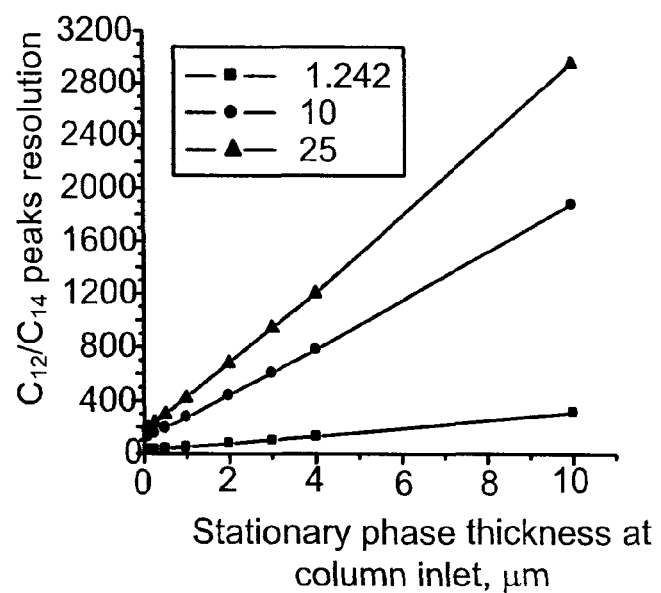
Figure 8C:
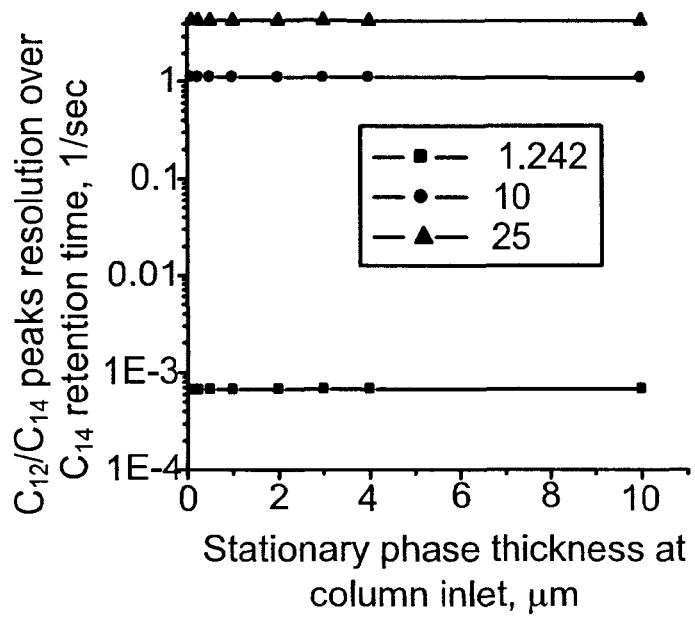
FIGS. 8c-8d illustrate $C_{14}$ peak width at half height and resolution of $C_{12}/C_{14}$ pair over retention time for $C_{14}$ as a function of the stationary phase thickness at the column inlet at the column inlet at different inlet/outlet pressure ratio.
Figure 8D:
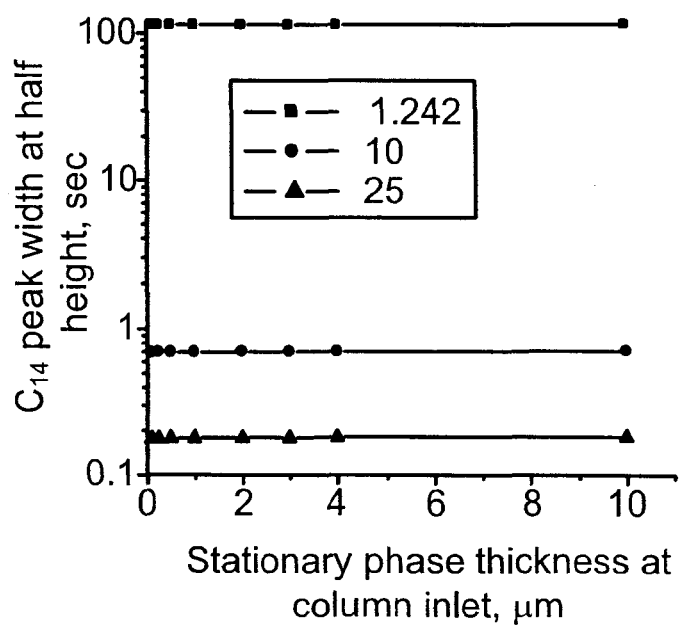
Figure 8E:
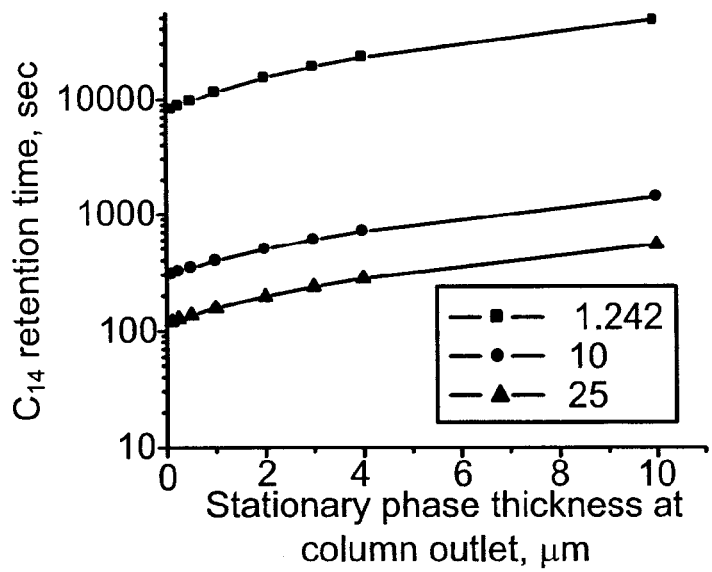
FIGS. 8e-8f illustrate $C_{14}$ retention time and resolution of $C_{12}/C_{14}$ as a function of the stationary phase thickness at the column outlet at different inlet/outlet pressure ratio.
Figure 8F:
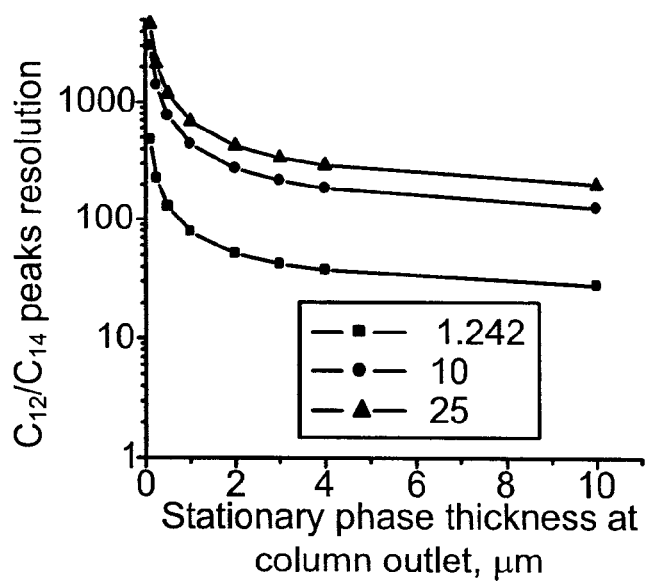
Figure 8G:
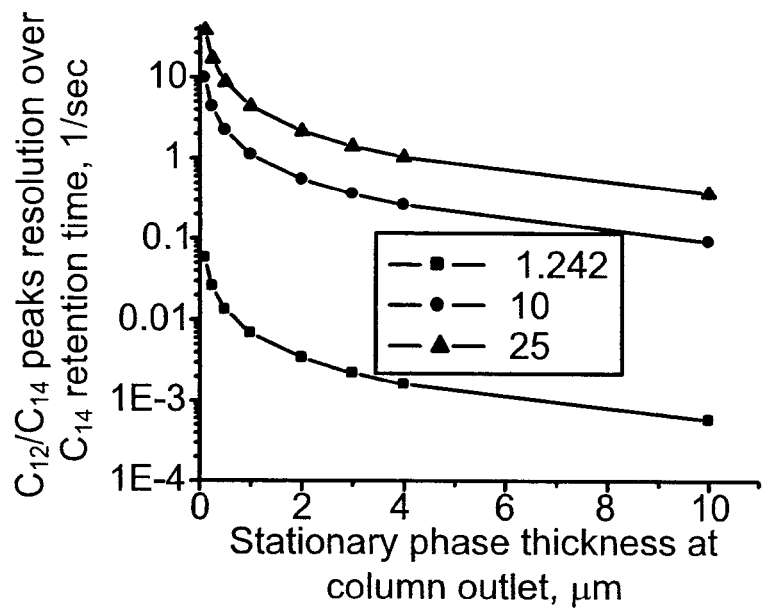
FIGS. 8g-8h illustrate $C_{14}$ peak width at half height and resolution of $C_{12}/C_{14}$ pair over retention time for $C_{14}$ as a function of the stationary phase thickness at the column outlet at different inlet/outlet pressure ratio.
Figure 8H:
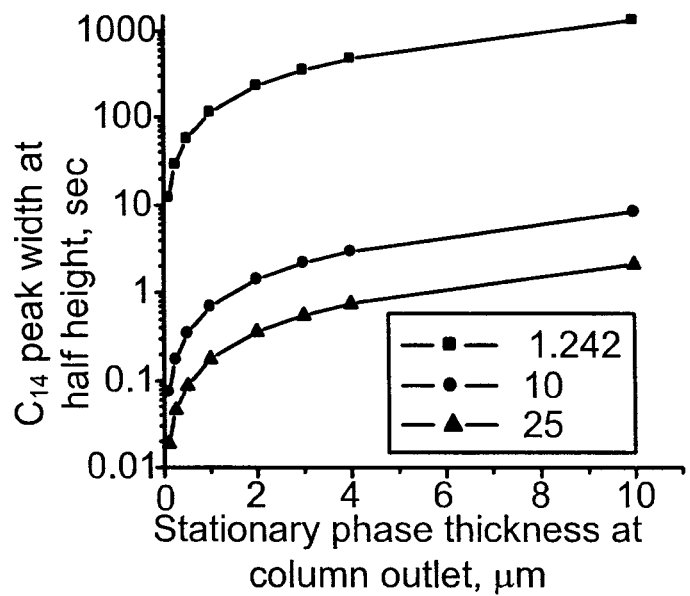
Figure 8I:
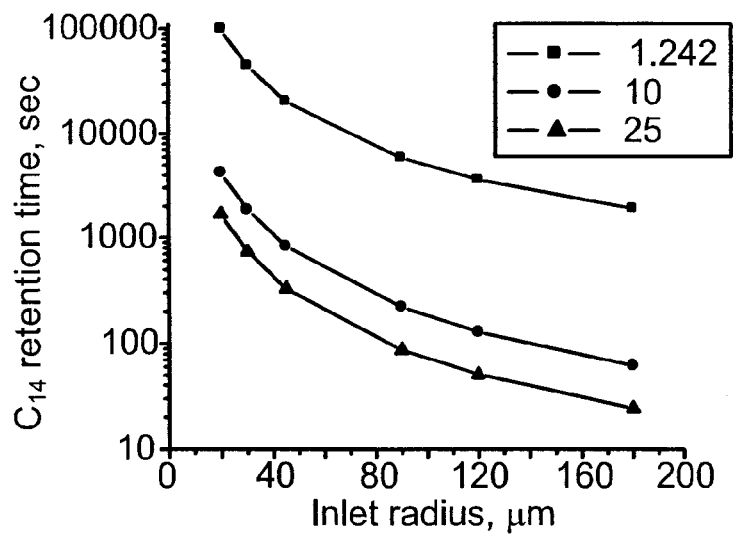
FIGS. 8i-8j illustrate $C_{14}$ retention time and resolution of $C_{12}/C_{14}$ as a function of the inlet column radius at the column inlet at different inlet/outlet pressure ratio.
Figure 8J:
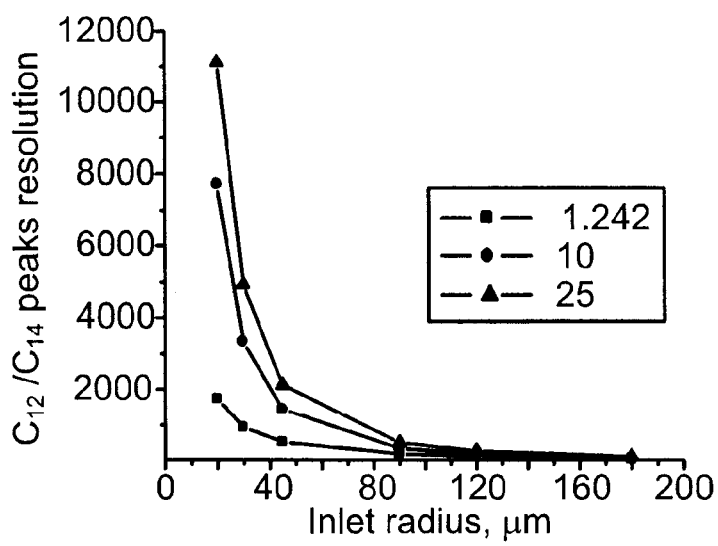
Figure 8K:
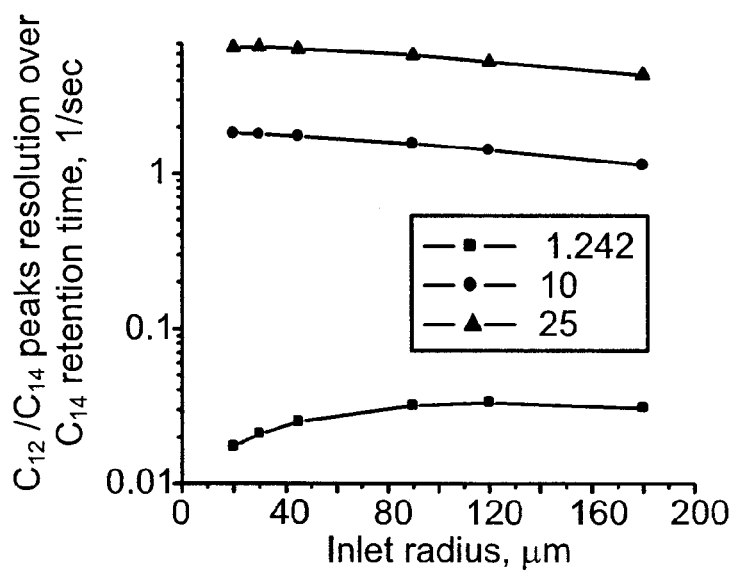
FIGS. 8k-8l illustrate Fig. $C_{14}$ peak width at half height and resolution of $C_{12}/C_{14}$ pair over retention time for $C_{14}$ as a function of the inlet column radius at the column inlet at different inlet/outlet pressure ratio.
Figure 8L:
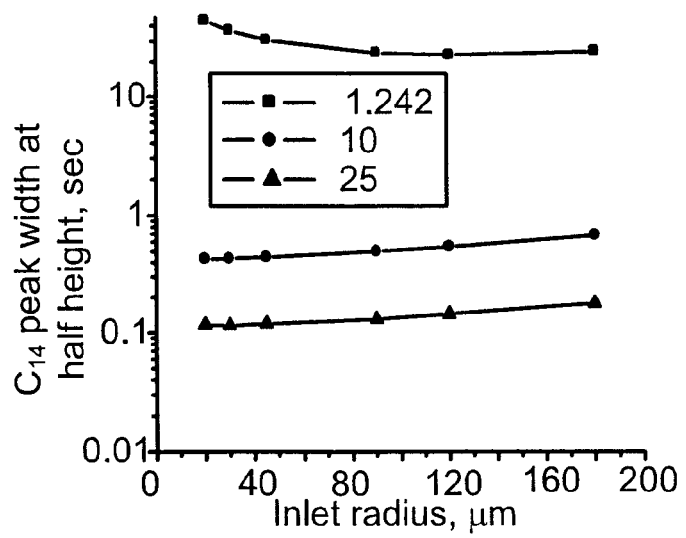
Figure 8M:
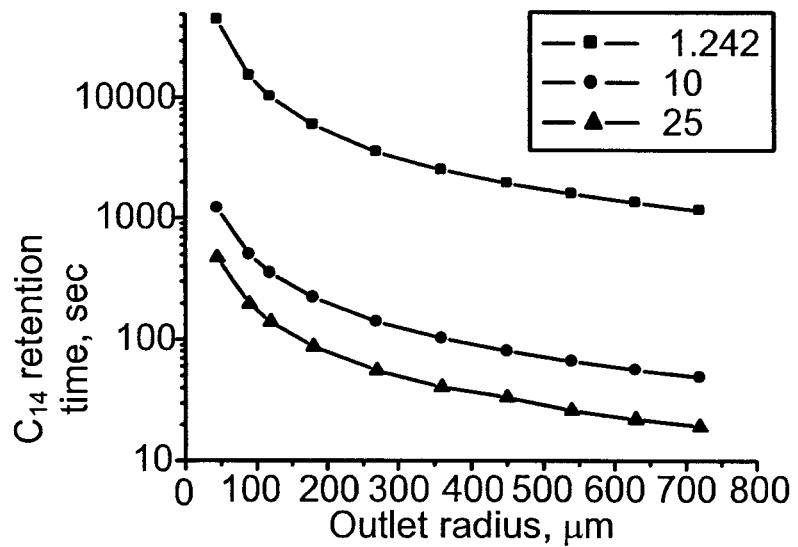
FIGS. 8m-8n illustrate $C_{14}$ retention time and resolution of $C_{12}/C_{14}$ as a function of the outlet column radius at the column inlet at different inlet/outlet pressure ratio.
Figure 8N:
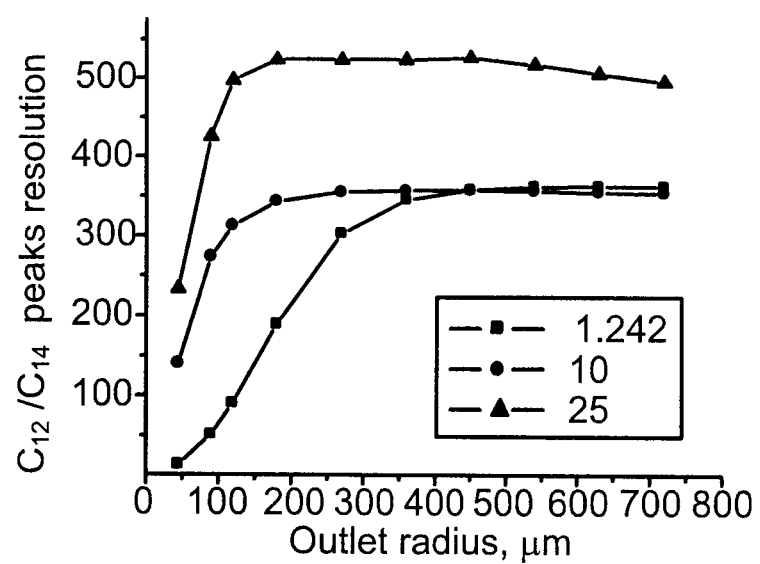
Figure 8O:
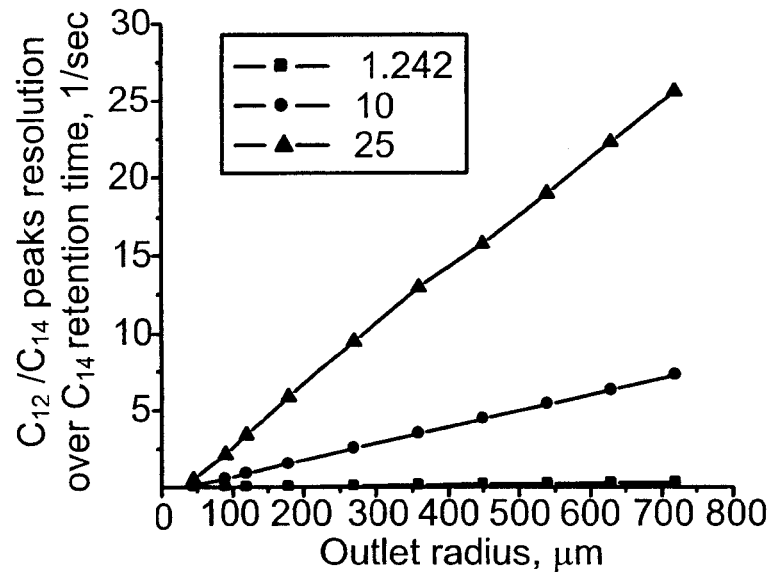
FIGS. 8o-8p illustrate $C_{14}$ peak width at half height and resolution of $C_{12}/C_{14}$ pair over retention time for $C_{14}$ as a function of the outlet column radius at the column inlet at different inlet/outlet pressure ratio.
Figure 8P:
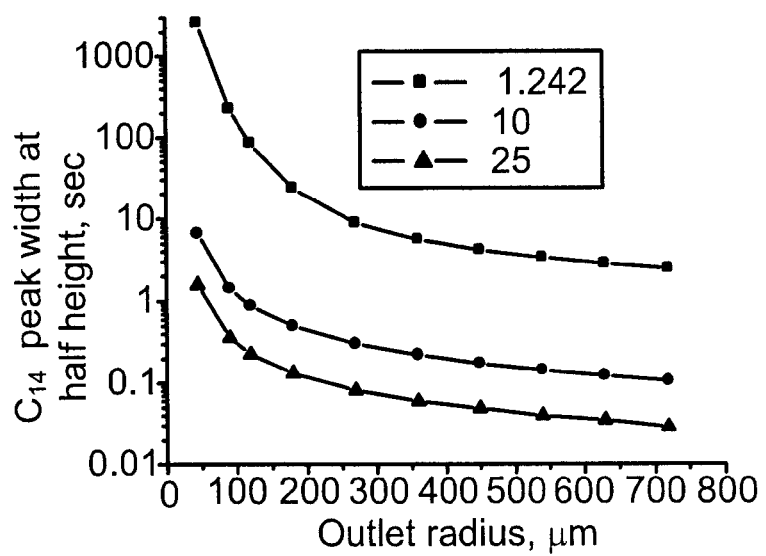

FIGS. 8a-8b illustrate $C_{14}$ retention time and resolution of $C_{12}/C_{14}$ as a function of the stationary phase thickness at the column inlet at different inlet/outlet pressure ratio. FIGS. 8c-8d illustrate $C_{14}$ peak width at half height and resolution of $C_{12}/C_{14}$ pair over retention time for $C_{14}$ as a function of the stationary phase thickness at the column inlet at different inlet/outlet pressure ratio. FIGS. 8e-8f illustrate $C_{14}$ retention time and resolution of $C_{12}/C_{14}$ as a function of the stationary phase thickness at the column outlet at different inlet/outlet pressure ratio. FIGS. 8g-8h illustrate $C_{14}$ peak width at half height and resolution of $C_{12}/C_{14}$ pair over retention time for $C_{14}$ as a function of the stationary phase thickness at the column outlet at different inlet/outlet pressure ratio. FIGS. 8i-8j illustrate $C_{14}$ retention time and resolution of $C_{12}/C_{14}$ as a function of the inlet column radius at the column inlet at different inlet/outlet pressure ratio. FIGS. 8k-8l illustrate Fig. $C_{14}$ peak width at half height and resolution of $C_{12}/C_{14}$ pair over retention time for $C_{14}$ as a function of the inlet column radius at the column inlet at different inlet/outlet pressure ratio. FIGS. 8m-8n illustrate $C_{14}$ retention time and resolution of $C_{12}/C_{14}$ as a function of the outlet column radius at the column inlet at different inlet/outlet pressure ratio. FIGS. 8o-8p illustrate $C_{14}$ peak width at half height and resolution of $C_{12}/C_{14}$ pair over retention time for $C_{14}$ as a function of the outlet column radius at the column inlet at different inlet/outlet pressure ratio.

The influence of the stationary phase thickness at the column beginning and at the column end was also numerically evaluated for $C_6/C_7$ and $C_{12}/C_{14}$ components. It has been found that increasing the stationary phase thickness at the column outlet negatively affects all chromatography system parameters: increasing the time of experiments, increasing the peak width, decreasing the peaks resolution. At the same increasing the stationary phase thickness at the column inlet leads to improvements in the peaks resolution although if the PRoT is considered than it can be seen from the evaluations that this parameter is saturating when the stationary phase thickness at the column inlet is increasing and this increment is much more significant for light components than for heavy ends. As shown in figures, FIGS. 9a-9h it is generally not useful to increase the stationary phase thickness at the column inlet more than 2-4 µm. At the same time it is important to note that increasing the stationary phase thickness at the column inlet significantly increases retention time. This is another reason to avoid an overly thick stationary phase at the column inlet.

Figure 9A:
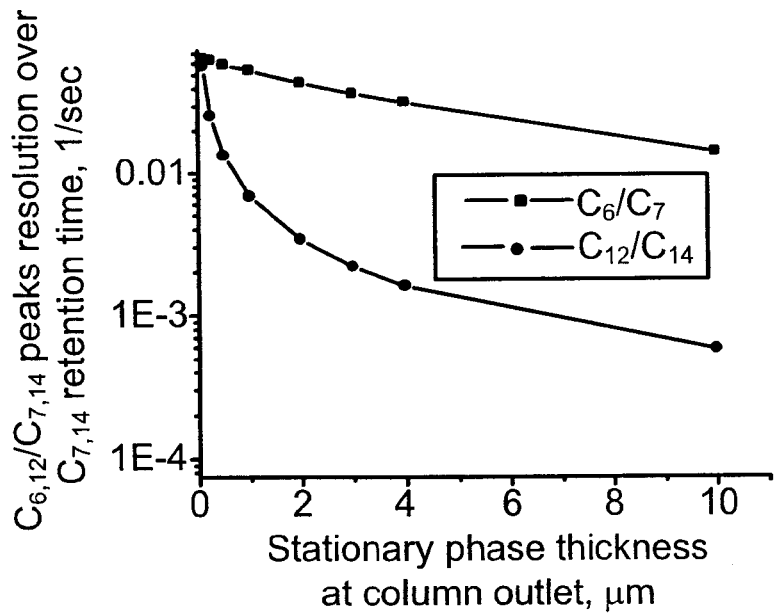
FIGS. 9a-9b illustrate resolution of $C_{6,12}/C_{7,14}$ pair over retention time for $C_{7,14}$ and resolution of $C_{6,12}/C_{7,14}$ pair as a function of the stationary phase thickness at the column outlet.
Figure 9B:
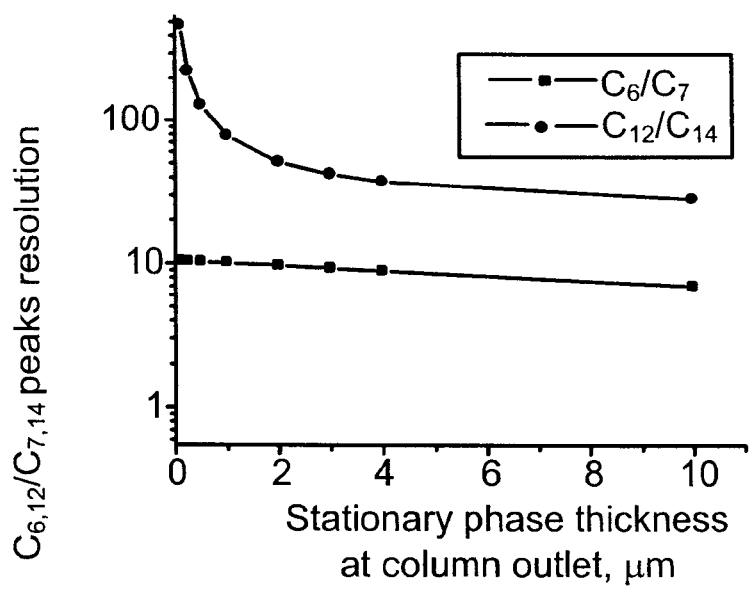
Figure 9C:
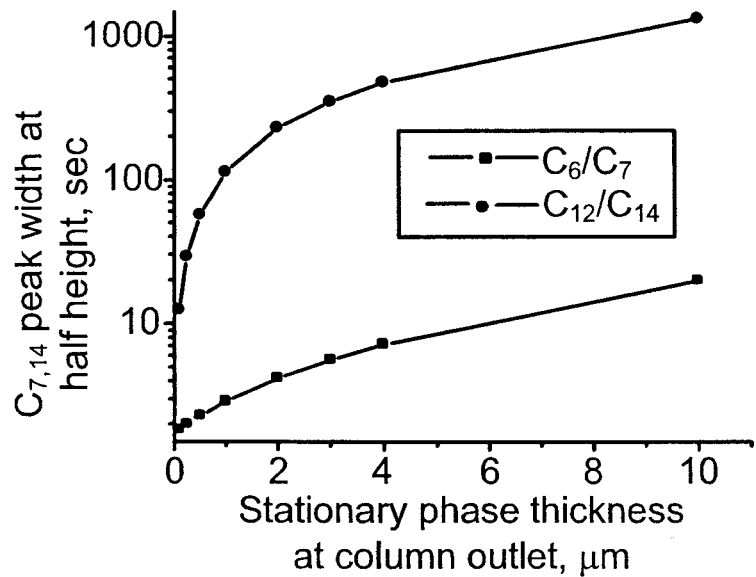
FIGS. 9c-9d illustrate peak width at half height and $C_{7,14}$ retention time as a function of the stationary phase thickness at the column outlet.
Figure 9D:
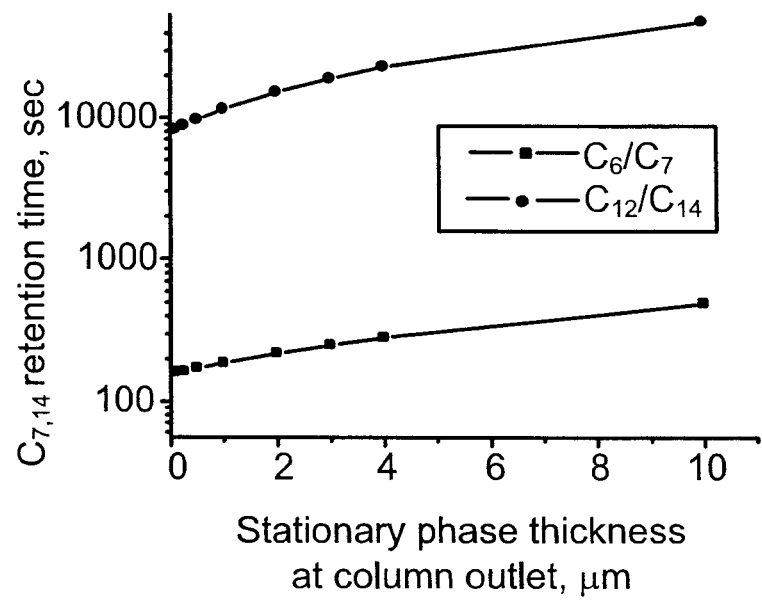
Figure 9E:
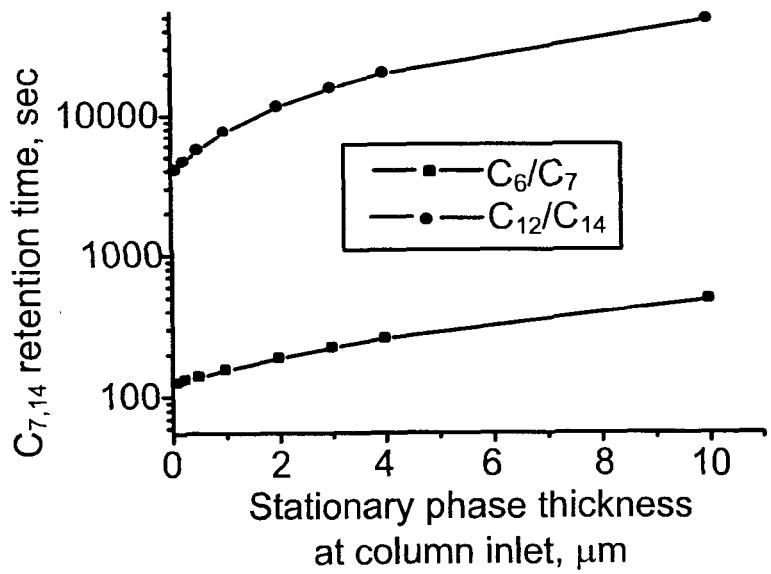
FIGS. 9e-9f illustrate $C_{7,14}$ retention time and resolution of $C_{6,12}/C_{7,14}$ pair over retention time for $C_{7,14}$ as a function of the stationary phase thickness at the column inlet.
Figure 9F:
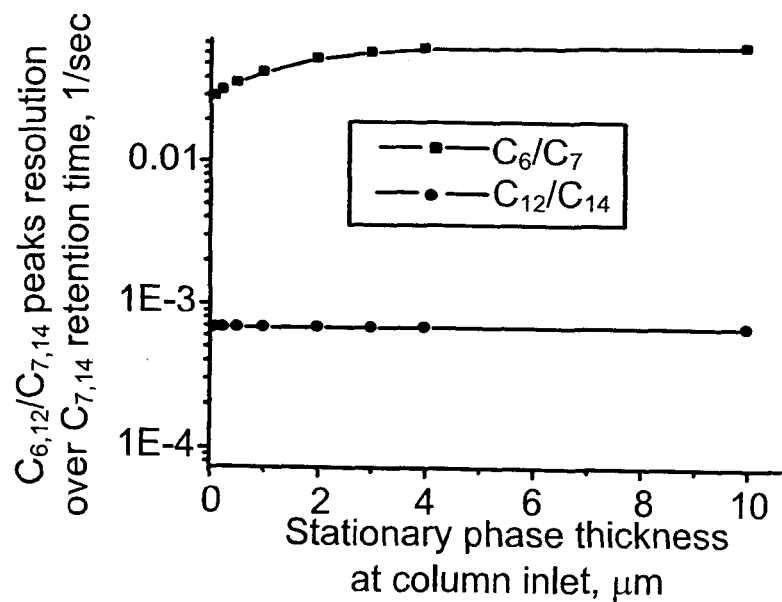
Figure 9G:
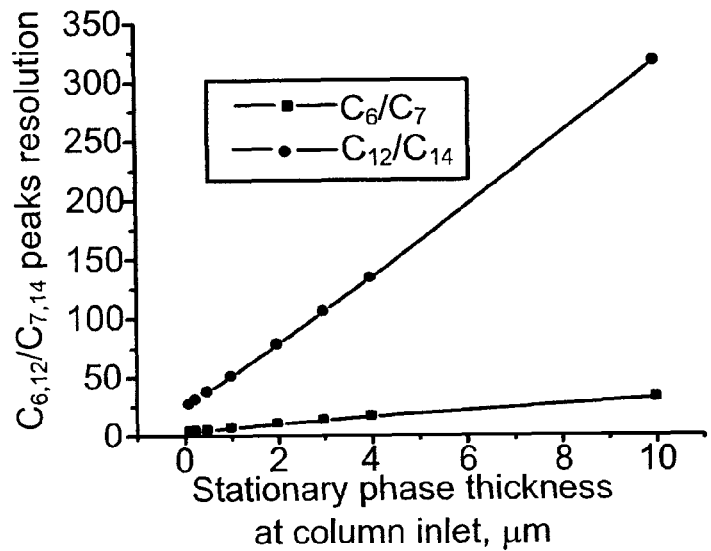
FIGS. 9g-9h illustrate resolution of $C_{6,12}/C_{7,14}$ pair and $C_{7,14}$ peak width at half height as a function of the stationary phase thickness at the column outlet.
Figure 9H:
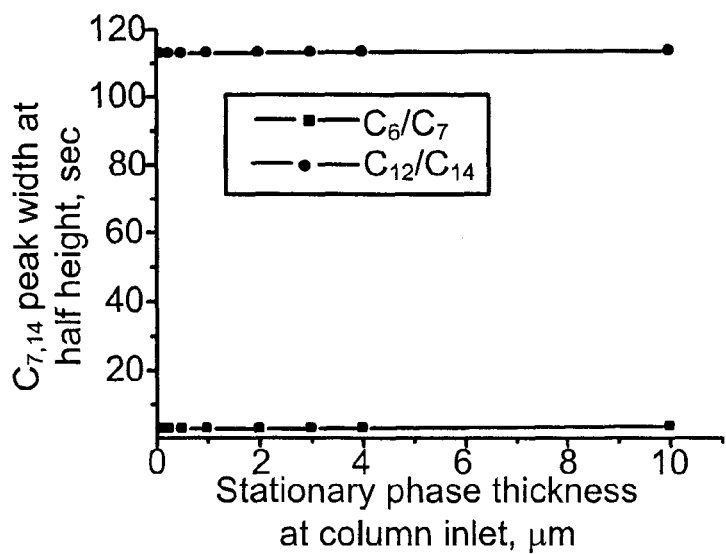

FIGS. 9a-9b illustrate resolution of $C_{6,12}/C_{7,14}$ pair over retention time for $C_{7,14}$ and resolution of $C_{6,12}/C_{7,14}$ pair as a function of the stationary phase thickness at the column outlet. FIGS. 9c-9d illustrate peak width at half height and $C_{7,14}$ retention time as a function of the stationary phase thickness at the column outlet. FIGS. 9e-9f illustrate $C_{7,14}$ retention time and resolution of $C_{6,12}/C_{7,14}$ pair over retention time for $C_{7,14}$ as a function of the stationary phase thickness at the column inlet. FIGS. 9g-9h illustrate resolution of $C_{6,12}/C_{7,14}$ pair and $C_{7,14}$ peak width at half height as a function of the stationary phase thickness at the column outlet.

In general, the influence of the column radius modulation is more significant for the system performance, as can be seen from FIGS. 10a-10h. Peaks resolution has a maximum as a function of the column outlet radius and a very steep slope in the beginning that allows improving the peaks resolution and the peaks resolution over time parameters keeping the outlet column radius in the reasonable range (~350 µm). Increasing outlet radius also reduces time of experiments and the peak width. As for the inlet column radius there are several optimum values and therefore the value chosen depends on what parameter is optimized, increased or decreased for a particular application. Increasing the inlet column radius leads to decrement in the time of experiments but at the same time to significant drop in the peaks resolution. In case when the key parameter is the peak width or the peaks resolution over time the optimum value depends on the analyzable component.

Figure 10A:
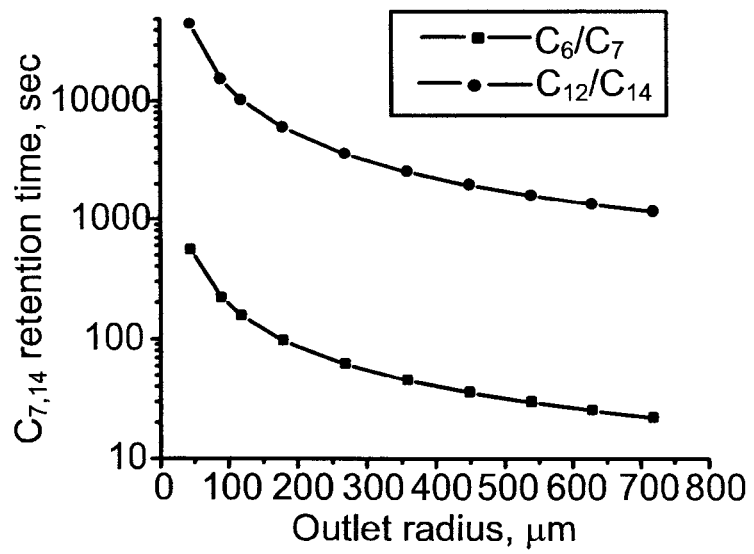
FIGS. 10a-10b illustrate $C_{7,14}$ retention time and resolution of $C_{6,12}/C_{7,14}$ pair over retention time for $C_{7,14}$ as a function of the outlet column radius.
Figure 10B:
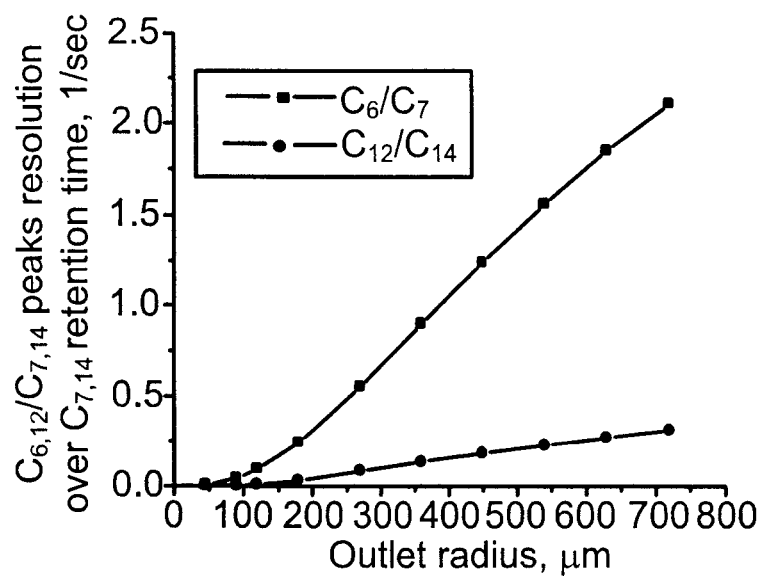
Figure 10C:
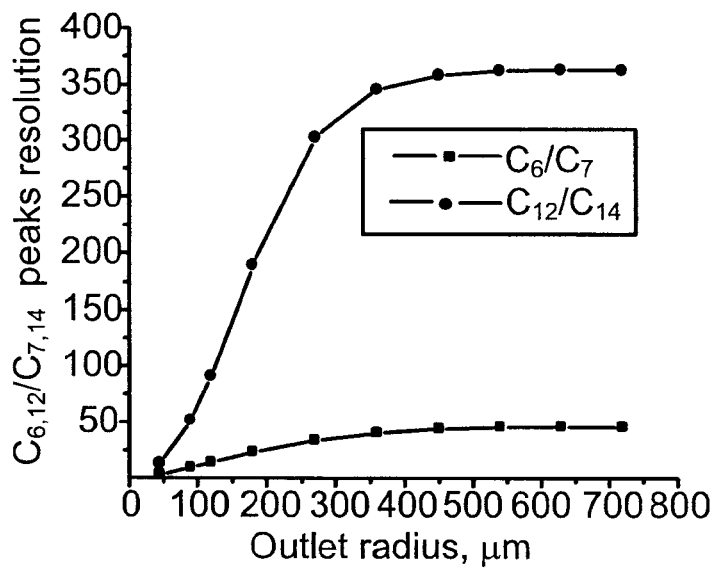
FIGS. 10c-10d illustrate resolution of $C_{6,12}/C_{7,14}$ pair and $C_{7,14}$ peak width at half height as a function of the outlet column radius.
Figure 10D:
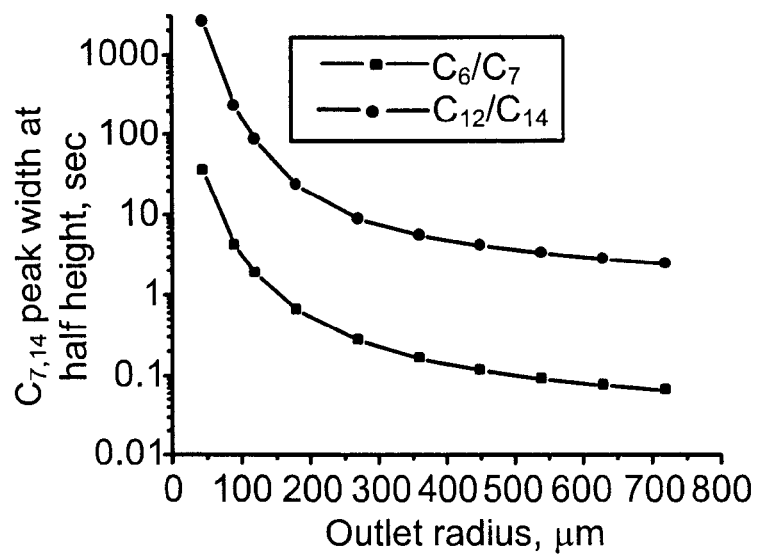
Figure 10E:
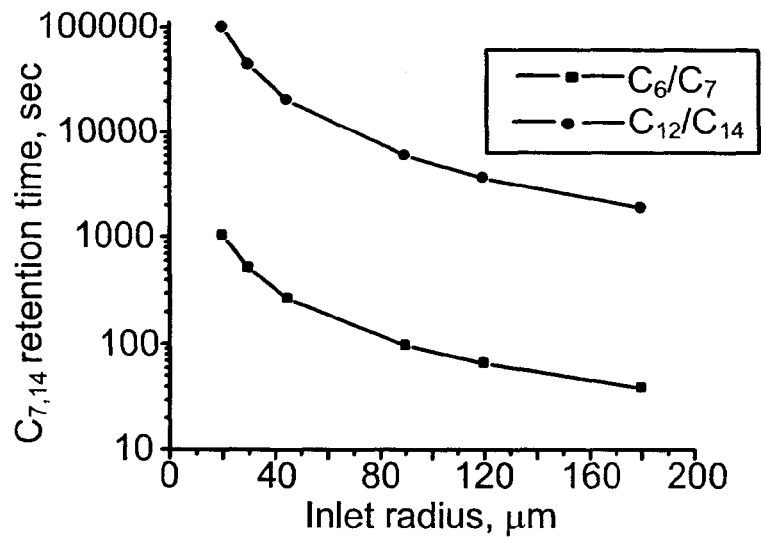
FIGS. 10e-10f illustrate $C_{7,14}$ retention time and resolution of $C_{6,12}/C_{7,14}$ pair over retention time for $C_{7,14}$ as a function of the inlet column radius.
Figure 10F:
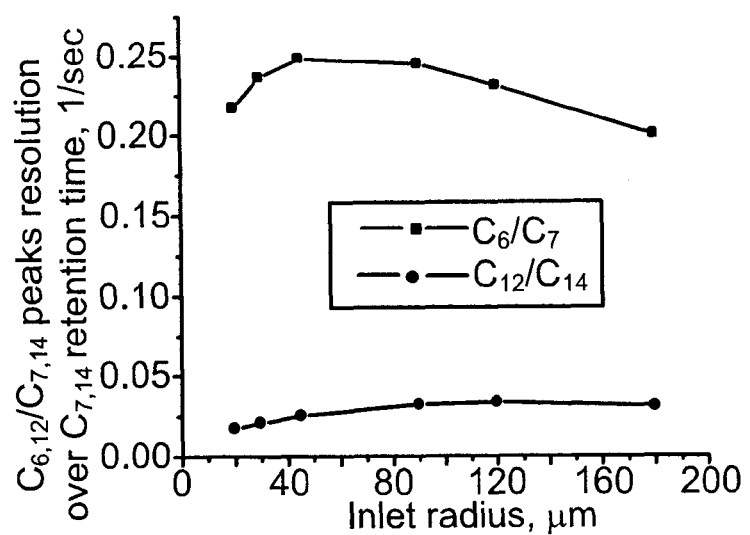
Figure 10G:
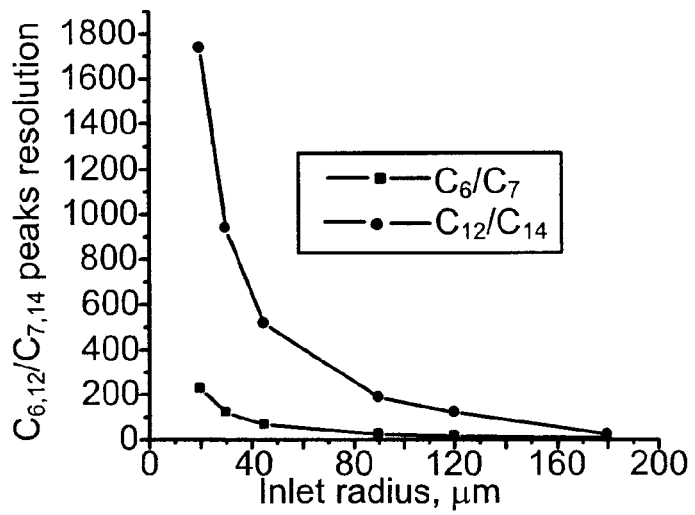
FIGS. 10g-10h illustrate $C_{6,12}/C_{7,14}$ pair peak resolution and $C_{7,14}$ peak width at half height as a function of the inlet column radius.
Figure 10H:
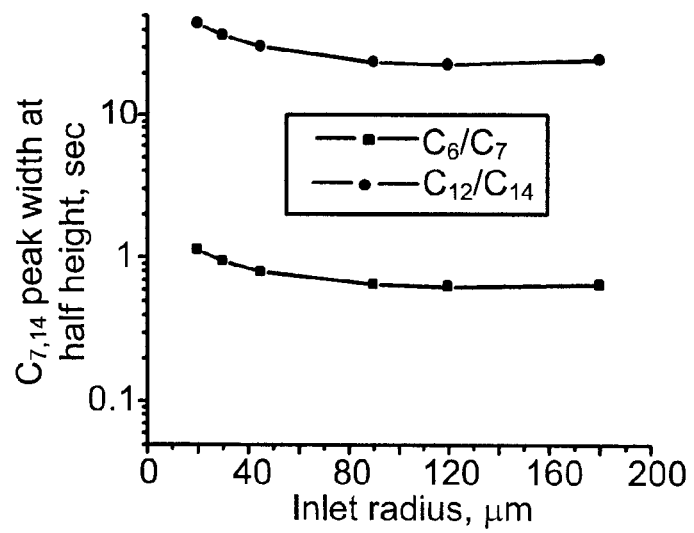

FIGS. 10a-10b illustrate $C_{7,14}$ retention time and resolution of $C_{6,12}/C_{7,14}$ pair over retention time for $C_{7,14}$ as a function of the outlet column radius. FIGS. 10c-10d illustrate resolution of $C_{6,12}/C_{7,14}$ pair and $C_{7,14}$ peak width at half height as a function of the outlet column radius. FIGS. 10e-10f illustrate $C_{7,14}$ retention time and resolution of $C_{6,12}/C_{7,14}$ pair over retention time for $C_{7,14}$ as a function of the inlet column radius. FIGS. 10g-10h illustrate $C_{6,12}/C_{7,14}$ pair peak resolution and $C_{7,14}$ peak width at half height as a function of the inlet column radius.

As for the influence of column length on the performance of the modeled chromatography system it has been found that increasing in the column length will increase the retention time and the peak width as well as the resolution. The resolution for the different column lengths no longer follows the ratio $R_1/R_2 \sim \sqrt{L_1/L_2}$, where $R_i$ is the peaks resolution and $L_i$ is the column length. However, the PRoT will decrease in case of the column length increment. The optimum column inlet radius for the PRoT and the peak width becomes smaller in the cases of shorter columns. The same scenario will be followed for the optimum stationary phase thickness at the column inlet that is getting smaller for shorter column. These trends are correct as for $C_6/C_7$ and for $C_{12}/C_{14}$.

Figure 11A:
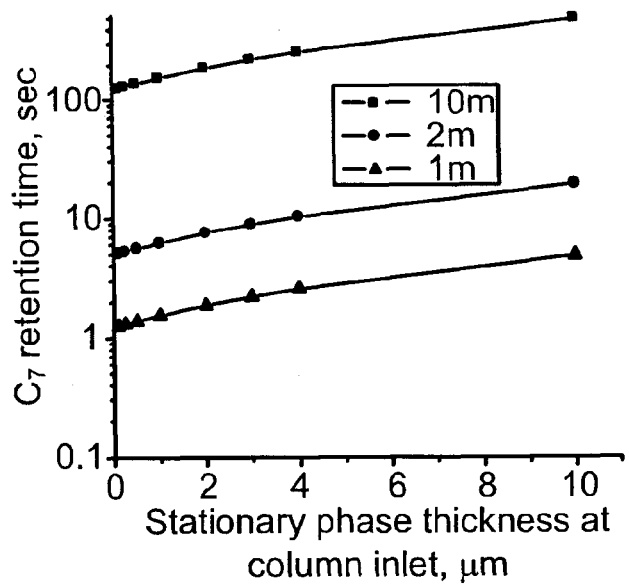
FIGS. 11a-11b illustrates $C_7$ retention time and resolution of $C_6/C_7$ pair as a function of the stationary phase thickness at the column inlet at different column lengths.
Figure 11B:
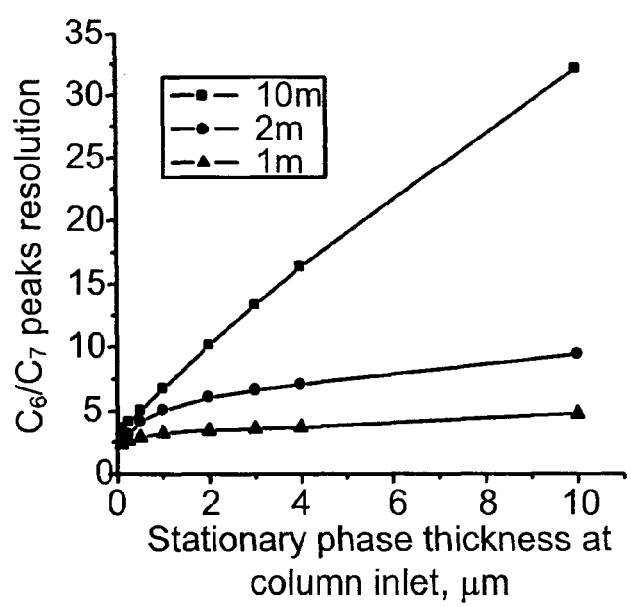
Figure 11C:
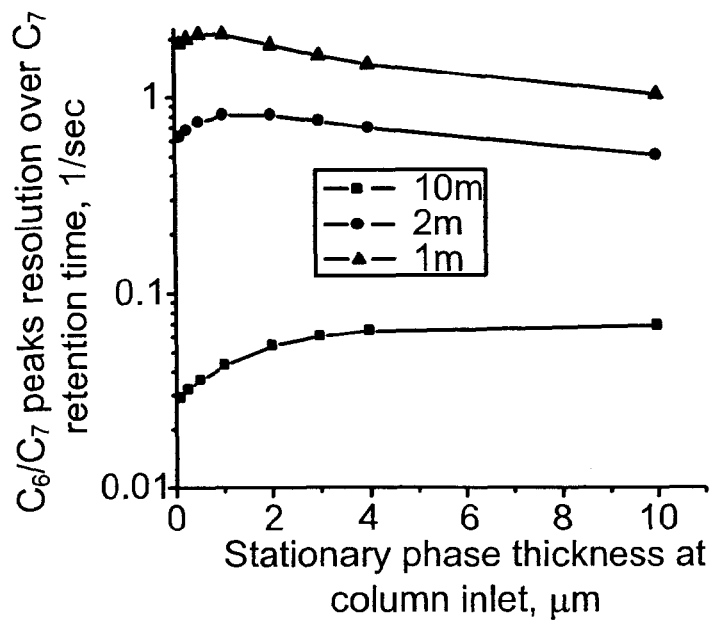
FIGS. 11c-11d illustrates $C_7$ peak width at half height and resolution of $C_6/C_7$ pair over retention time for $C_7$ as a function of the stationary phase thickness at the column inlet at different column lengths.
Figure 11D:
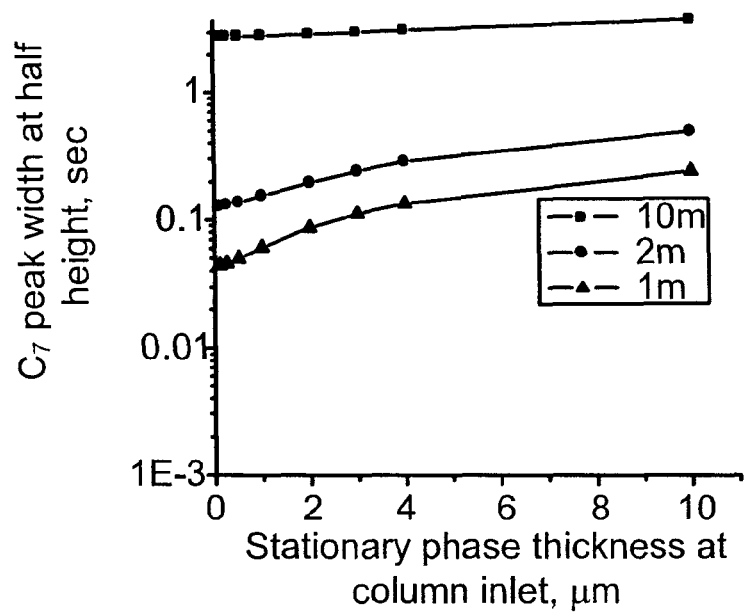
Figure 11E:
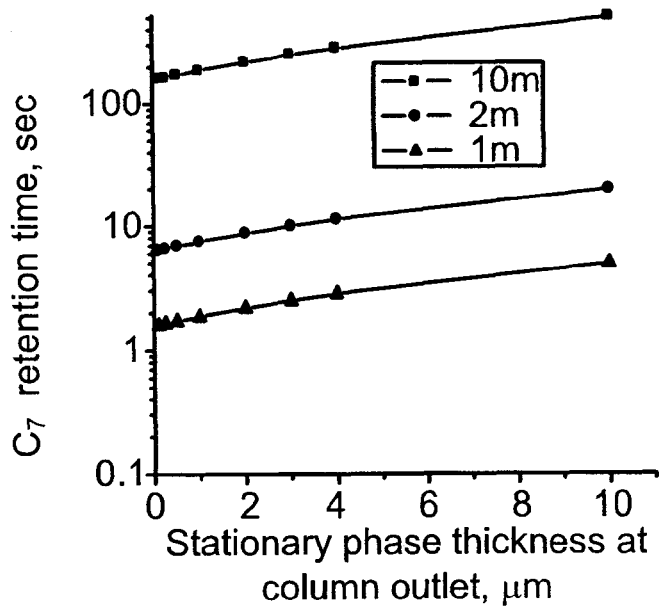
FIGS. 11e-11f illustrates $C_7$ retention time and resolution of $C_6/C_7$ pair as a function of the stationary phase thickness at the column outlet at different column lengths.
Figure 11F:
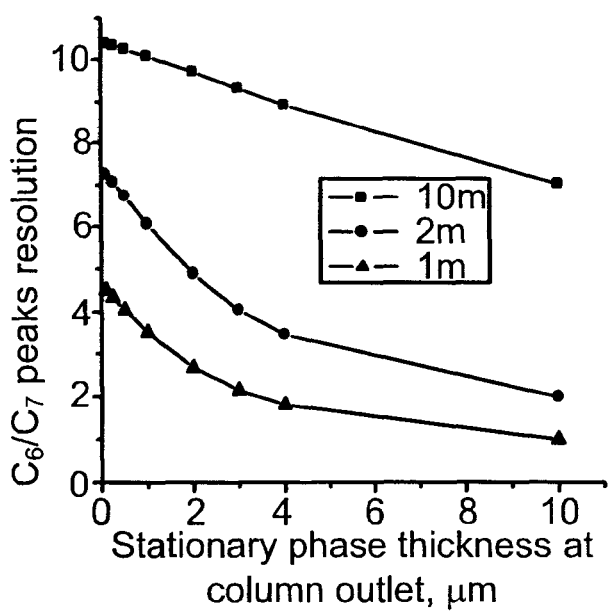
Figure 11G:
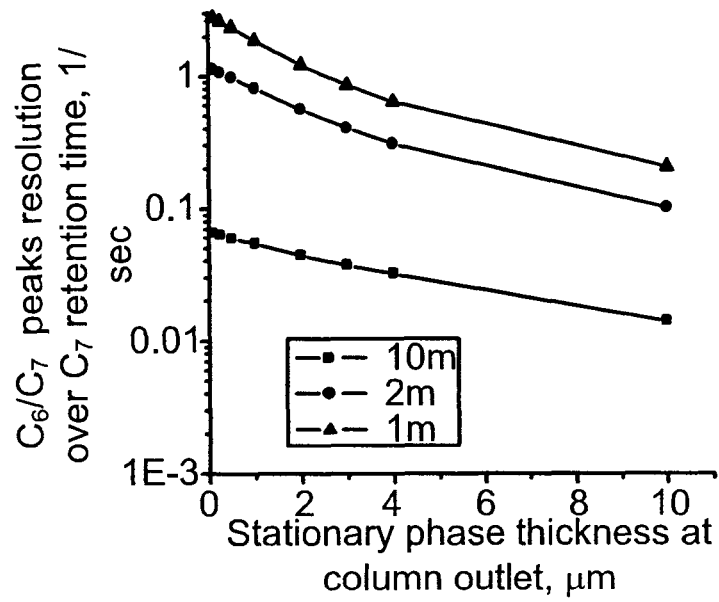
FIGS. 11g-11h illustrates $C_7$ peak width at half height and resolution of $C_6/C_7$ pair over retention time for $C_7$ as a function of the stationary phase thickness at the column outlet at different column lengths.
Figure 11H:
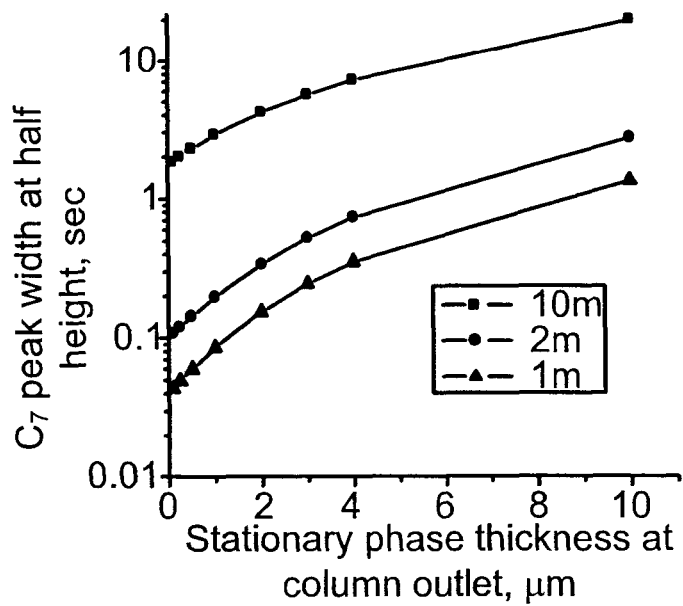
Figure 11I:
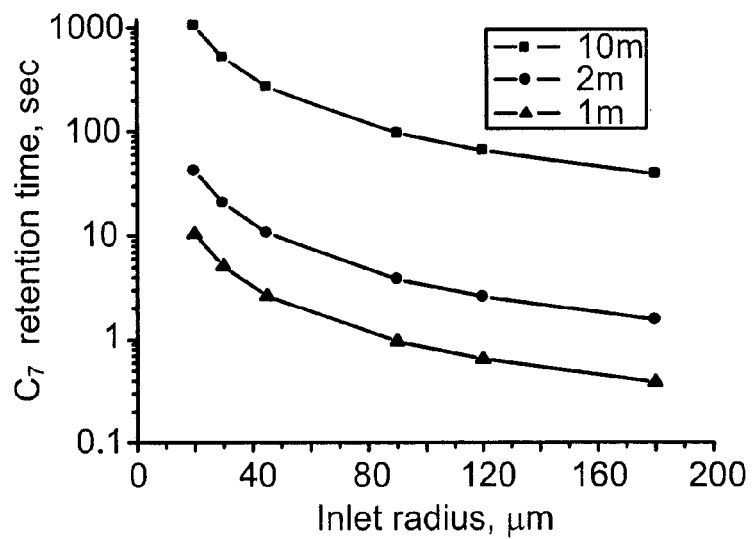
FIGS. 11i-11j illustrates $C_7$ retention time and resolution of $C_6/C_7$ pair as a function of the inlet column radius at different column lengths.
Figure 11J:
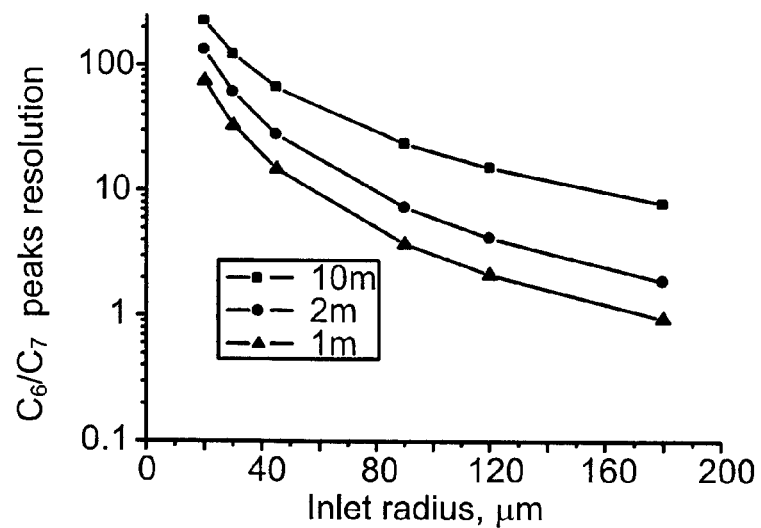
Figure 11K:
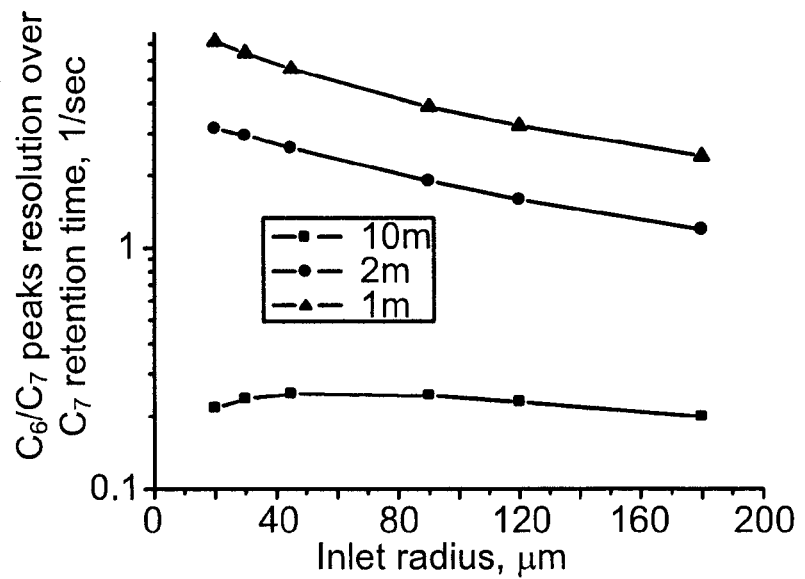
FIGS. 11k-11l illustrates $C_7$ peak width at half height and resolution of $C_6/C_7$ pair over retention time for $C_7$ as a function of the inlet column radius at different column lengths.
Figure 11L:
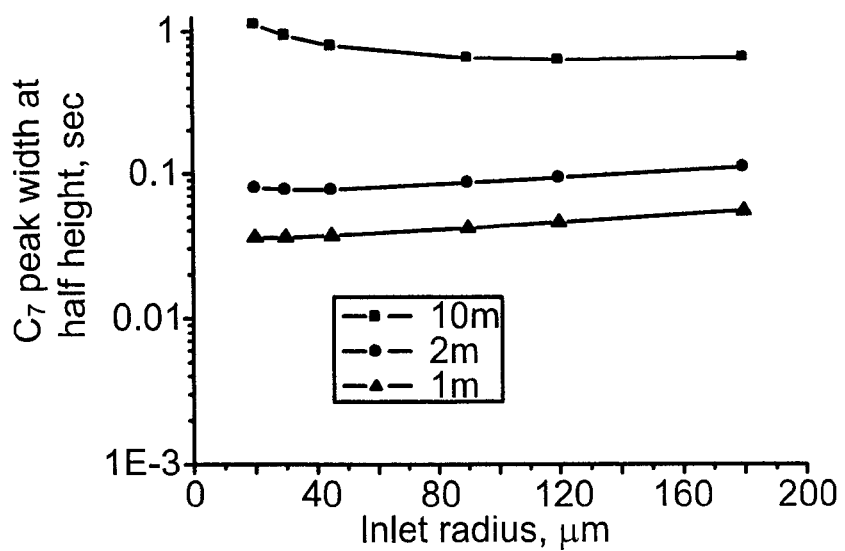

FIGS. 11a-11b illustrates $C_7$ retention time and resolution of $C_6/C_7$ pair as a function of the stationary phase thickness at the column inlet at different column lengths. FIGS. 11c-11d illustrates $C_7$ peak width at half height and resolution of $C_6/C_7$ pair over retention time for $C_7$ as a function of the stationary phase thickness at the column inlet at different column lengths. FIGS. 11e-11f illustrates $C_7$ retention time and resolution of $C_6/C_7$ pair as a function of the stationary phase thickness at the column outlet at different column lengths. FIGS. 11g-11h illustrates $C_7$ peak width at half height and resolution of $C_6/C_7$ pair over retention time for $C_7$ as a function of the stationary phase thickness at the column outlet at different column lengths. FIGS. 11i-11j illustrates $C_7$ retention time and resolution of $C_6/C_7$ pair as a function of the inlet column radius at different column lengths. FIGS. 11k-11l illustrates $C_7$ peak width at half height and resolution of $C_6/C_7$ pair over retention time for $C_7$ as a function of the inlet column radius at different column lengths.

Manufacturing a column with a continuously modulated geometry is more challenging when standard, non-MEMS, column manufacturing technology is to be used. Therefore, the following evaluations have been undertaken to understand the impact of composite designs as opposed to continuously modulated designs. To evaluate the composite column performance the column was broken on several parts and the performance of each column was evaluated and the total resolution of composite column was compared to the resolution of the column having continuously modulated geometry.

Figure 12A:
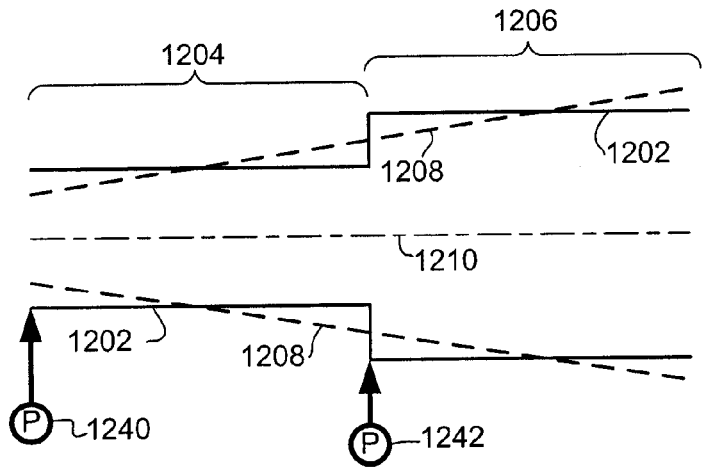
FIGS. 12a-12c illustrate examples of composite columns according to embodiments.
Figure 12B:
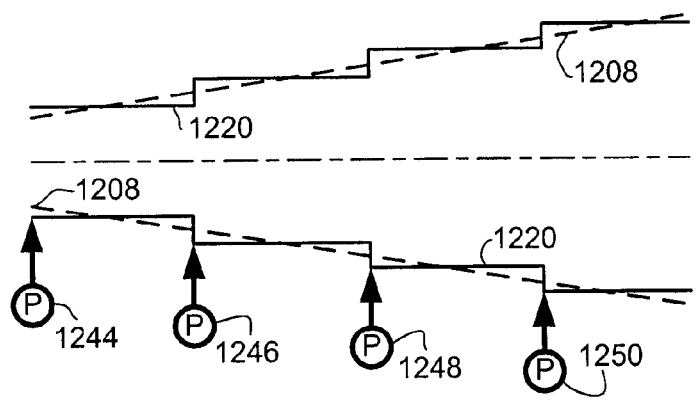
Figure 12C:
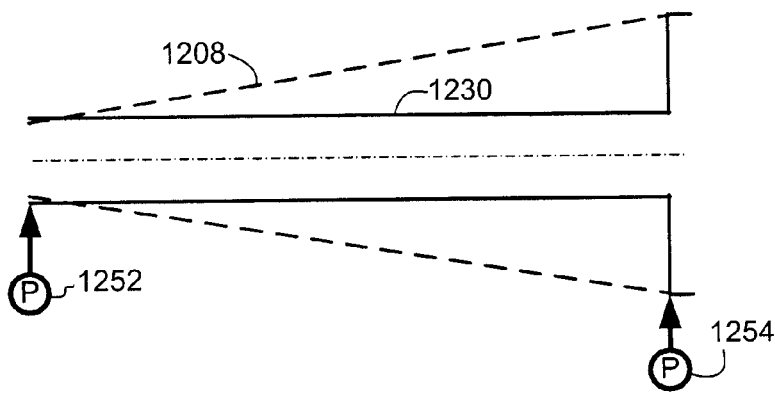

A column with linearly increasing column radius was taken as an example and compared with composite columns having a constant radius for each column segment equal to average radius of the variable column segment. FIGS. 12a-12c illustrate examples of composite columns according to embodiments. FIG. 12a shows a column 1202 which is a composite of two equal length sections 1204 and 1206. Also shown for comparison purposes is comparison column 1208 having a linearly increasing radius and axis 1210. The radius of section 1204 is equal to the average radius of column 1208 over the length of section 1204. Similarly, the radius of section 1206 equal to the average radius of column 1208 over the length of section 1206.

FIG. 12b shows a composite column 1220 which is made up of four equal length sections. Again, each of the four sections of column 1220 have a radius equal to the average radius of the comparison column 1208 over the length of that section. the column was broken on four equal parts and radius of each column was constant and equals to the average value of the column radius along the same interval of the variable column. FIG. 12c shows a column 1230 that is a composite of two sections. The first section has a length equal to 98% of the length of comparison column 1208, and the second section has a length equal to 2% of that of column 1208. For the composite columns shown in FIGS. 12a-12c, the evaluation computations were done for $C_6$ and $C_7$, and a stationary phase thickness of 2 µm. The comparison column radius 1206 has an inlet radius of 90 µm and an outlet radius of 180 µm.

For the two section composite column 1202 shown in FIG. 12a, the discrepancy between the computational results for comparison column 1208 and for composite column 1202 was about a 30% increase for the retention time, peak width, peaks resolution and resolution over time. For the four section composite column 1220 shown in FIG. 12b, the improvement over the results for composite column 1202 shown in FIG. 12a was about 15% for those parameters. For the two section composite column 1230 shown in FIG. 12c, The third case was compared with the comparison column 1208, the discrepancy was around 30% as is was for in the case of column 1202 shown in FIG. 12a. It is important to have independent pressure sources of the mobile phase at every column connection to provide identical to initial pressure profile. In FIG. 12a, pressure sources 1240 and 1242 are shown. The pressure profile of the equivalent continuously varying radius column should be matched as closely as practical. In other words, for linearly increasing radius comparison column 1208, a pressure profile analogous to that shown in curve 404 of FIG. 4 should be simulated in column 1202 with pressure sources 1240 and 1242. Likewise, in FIGS. 12b and 12c, the pressure profile should be matched using pressure sources 1244, 1246, 1248, and 1250, and pressure sources 1252 and 1254 respectively. Since the case of column 1230 shown in FIG. 12c showed almost no decrement in the time of experiments or peak width when compared with column 1202 in FIG. 12a, this is a practical alternative for some applications. Although, the peaks resolution increased dramatically with column 1230, it is in general simpler to manufacture that column combination. Thus it has been found that a significant improvement in chromatographic performance is possible with the composite columns shown in FIG. 12a-12c over conventional chromatographic column designs.

FIG. 13 shows an example of a column having an insert, according to embodiments. The arrangement in FIG. 13 can provide substantial improvements in chromatography just as can be gained from increasing column radius along the column as well as decreasing the stationary phase thickness. As shown in FIG. 13, instead of increasing column radius it is possible keep the radius of cylindrical column 1302 fixed and instead introduce a cylindrical insert 1304 within column 1302. In designing a column and insert arrangement, the dimensions of insert 1304 should be selected with respect to the radius of column 1302 according to the same design considerations as discussed herein with respect to variable radius columns and variable thickness stationary phase layers (e.g. decrease in time of experiment, improvement in the chromatographic resolution, and improvement of the peaks resolution over time). For example, the shape of insert 1304 shown will work in the same way as linearly increasing column radius. Furthermore, having insert 1304 in column 1302 allows for the deposit of stationary phase 1308 on the surface of insert 1304, as well as stationary phase 1306 on the surface of column 1302. This increased surface area increases the area of interaction between the analyzable molecules and stationary phase.

FIGS. 14a-14b shows an example of insert in a chromatographic column, according to embodiments. FIG. 14a is a cross sectional view wherein column 1402 has four inserts 1404, 1406, 1408 and 1410 onto which stationary phase is deposited. FIG. 14b shows column 1402 and two of the inserts 1404 and 1408. As shown in FIG. 14b, the size of the inserts can be tapered along the length of the column such that the surface area onto which the stationary phase is deposited decreases down the length of the column.

From the MEMS manufacturing point of view a circular cross section geometry for columns is generally more complicated than a rectangular geometry. Accordingly, evaluations have been carried out to understand the performance of rectangular geometries. A model is based on the same transport equation describing the motion of solute through the column:

$$\frac{\partial N_m}{\partial t} + v_g \cdot \frac{\partial N_m}{\partial x} = D_m \cdot \frac{\partial^2 N_m}{\partial x^2} - N_m \cdot \frac{\partial v_g}{\partial x},$$

where $N_m$ is the concentration of the solute in the mobile phase, $D_m$ is the diffusion coefficient of the solute molecules in the mobile phase, $v_g$ is the average velocity of the carrier gas. The last term on the right side responsible for the convection is usually omitted due to insignificant correction of the results. The moment analysis will lead to the equation for the concentration peak variance:

$$\sigma_i^2 = \frac{L_{column}^2 \cdot m_2}{m_1^2} =$$

$$L_{column} \cdot \left( \frac{2 \cdot D_{m_i} \cdot j_1}{v_i} + \frac{0.9 + 2 \cdot k_i + 35 \cdot k_i^2}{96 \cdot (1 + k_i)^2} \cdot \frac{W_{column_i}^2}{D_{m_i}} \cdot v_i \cdot j_1 + \frac{2}{3} \cdot \frac{k_i}{(1 + k_i)^2} \cdot \frac{d_{f_i}^2}{D_{st_i}} \cdot Y \cdot v_i \cdot j_2 \right),$$

where in case of Spangler and Giddings-Gushka approach $Y_{S-G} = 1$ and for Golay approach $$Y_G = \frac{(W+H)^2}{H^2}.$$

For further details relating to these approaches, see: Leon Lapidus and Neal R. Amundson, *Mathematics of adsorption in beds. VI The effect of longitudinal diffusion in ion exchange and chromatographic columns*, J. Phys. Chem., Vol. 56, November 1952, P. 984-988; L Podmanisczky, L. Szepesy, K. Lakszner, *Determination of thermodynamic characteristics from retention data in GC*, Chromatographia, VOl. 20, #10, October 1985, P. 591-628; and Eli Grushka *Chromatographic peak shapes. Their origin and dependence on the experimental parameters*, J. Phys. Chem., Vol. 76, No. 18, 1972, P. 2586-2593, all of which are incorporated by reference herein.

Following the same method that has been used to evaluate the performance of circular column with column radius variation and variation of stationary phase thickness it is possible to evaluate how the variation in the column width, column height will affect the performance of GC system.

The band velocity along the column could be computed using the same approach that has been described in the section about circular column:

$$v_i = \frac{v_0}{p_i} \cdot \frac{\eta_{He_0}}{\eta_{He_i}} \cdot \frac{W_i^2 \cdot H_i^2}{W_0^2 \cdot H_0^2} \cdot \frac{W_0^2 + H_0^2}{W_i^2 + H_i^2},$$

In the model the pressure gradient was used in the form:

$$P(x) = P_{out} \cdot \sqrt{\gamma^2 - \frac{F_x}{F_L} \cdot (\gamma^2 - 1)},$$

where $P_{out}$ are the inlet and outlet pressures and $L_{column}$ is the column length, and in case of linear variation of the column width the coefficient $F_x$ and $F_L$ will be:

$$F_x = \frac{\ln(W_{in} \cdot H_{in}) \cdot \left( \ln\left( H_{in} \cdot \frac{W_f - W_{in}}{L_{column}} \cdot x \right) - 1 \right)}{H_{in} \cdot \frac{W_f - W_{in}}{L_{column}}}$$

$$F_L = \frac{\ln\left( \frac{W_f}{W_{in}} \right)}{H_{in} \cdot \frac{W_f - W_{in}}{L_{column}}}$$

As a basis for the computation the partition coefficients and diffusion coefficients for the mobile phase, data from experiments gathered on an commercial gas chromatography system from Agilent was used. As shown in FIGS. 15a-15f, the $C_6/C_7$ peaks resolution was calculated in the case of variation of column width, column height, and column stationary phase thickness (and all together). From the evaluations it has been found that the optimum profile for the resolution over time parameter is the same as for the peaks resolution—the most rapidly changing profile in the end of the column. Otherwise two geometries behave very similarly.

Figure 15A:
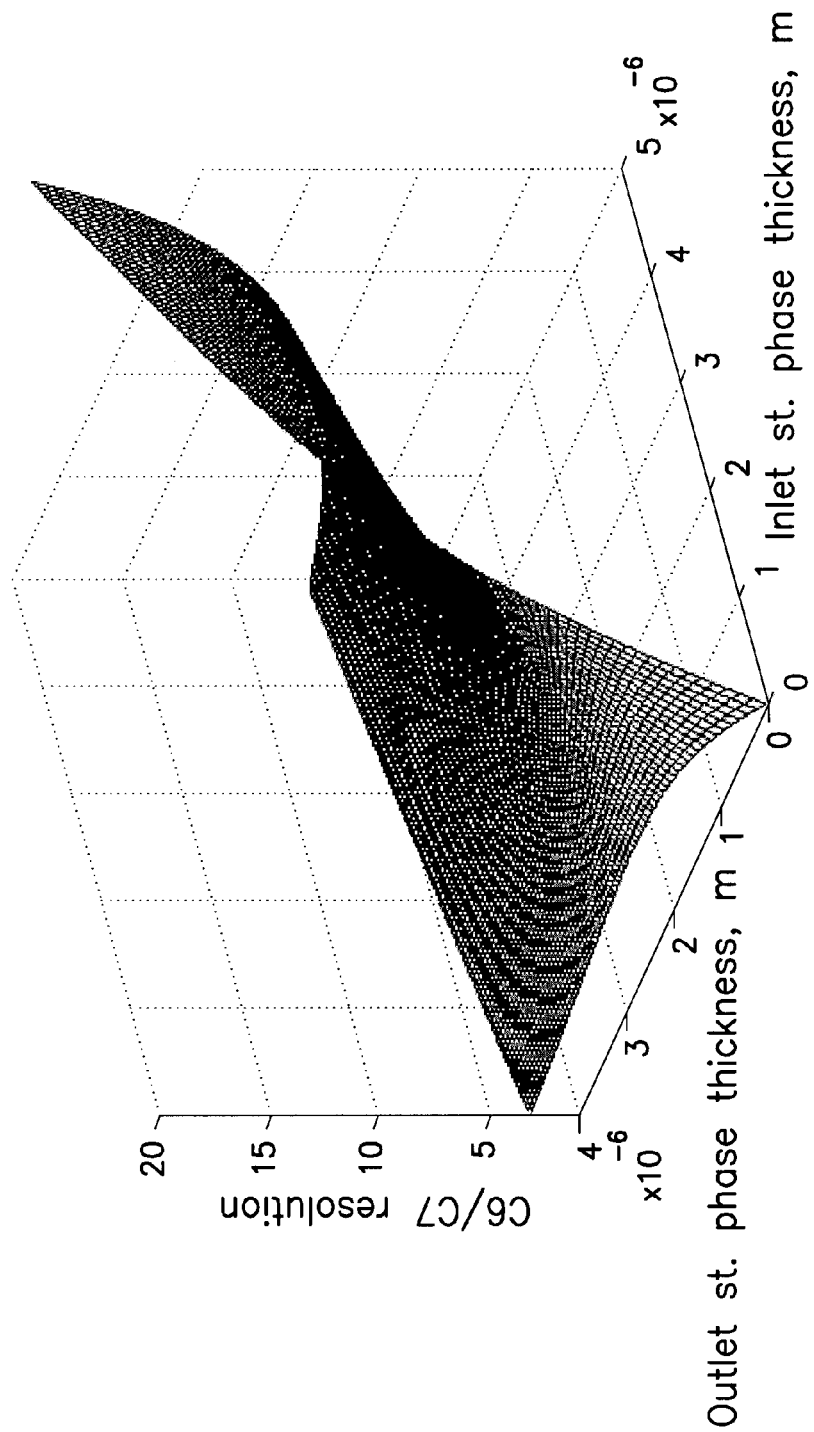
FIGS. 15a-15b illustrate the effect of inlet-outlet stationary phase thickness modulation on the $C_6/C_7$ peaks resolution and $C_6/C_7$ peaks resolution over $C_7$ retention time.
Figure 15B:
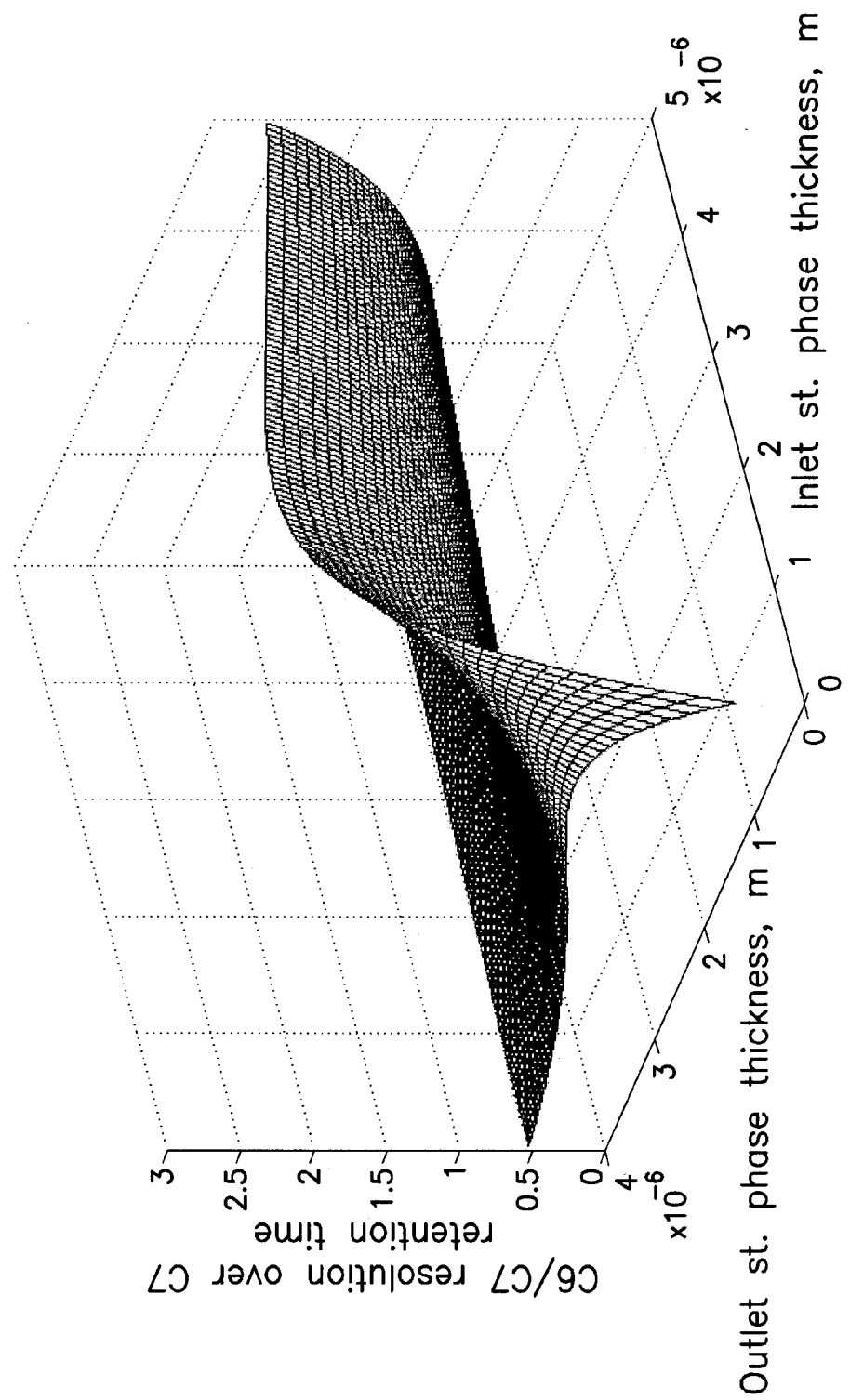
Figure 15C:
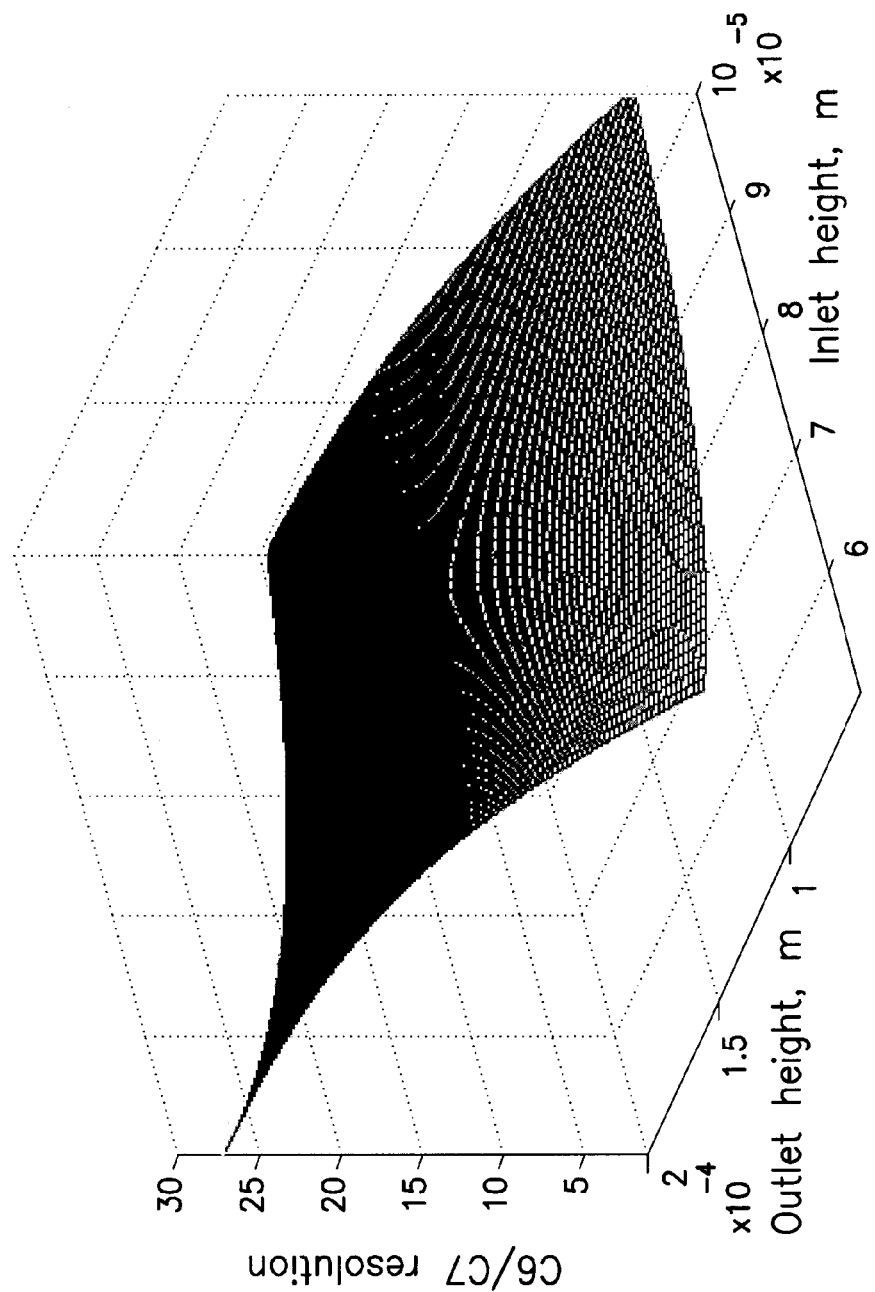
FIGS. 15c-15d illustrate the effect of inlet-outlet column height modulation on the $C_6/C_7$ peaks resolution and $C_6/C_7$ peaks resolution over $C_7$ retention time.
Figure 15D:
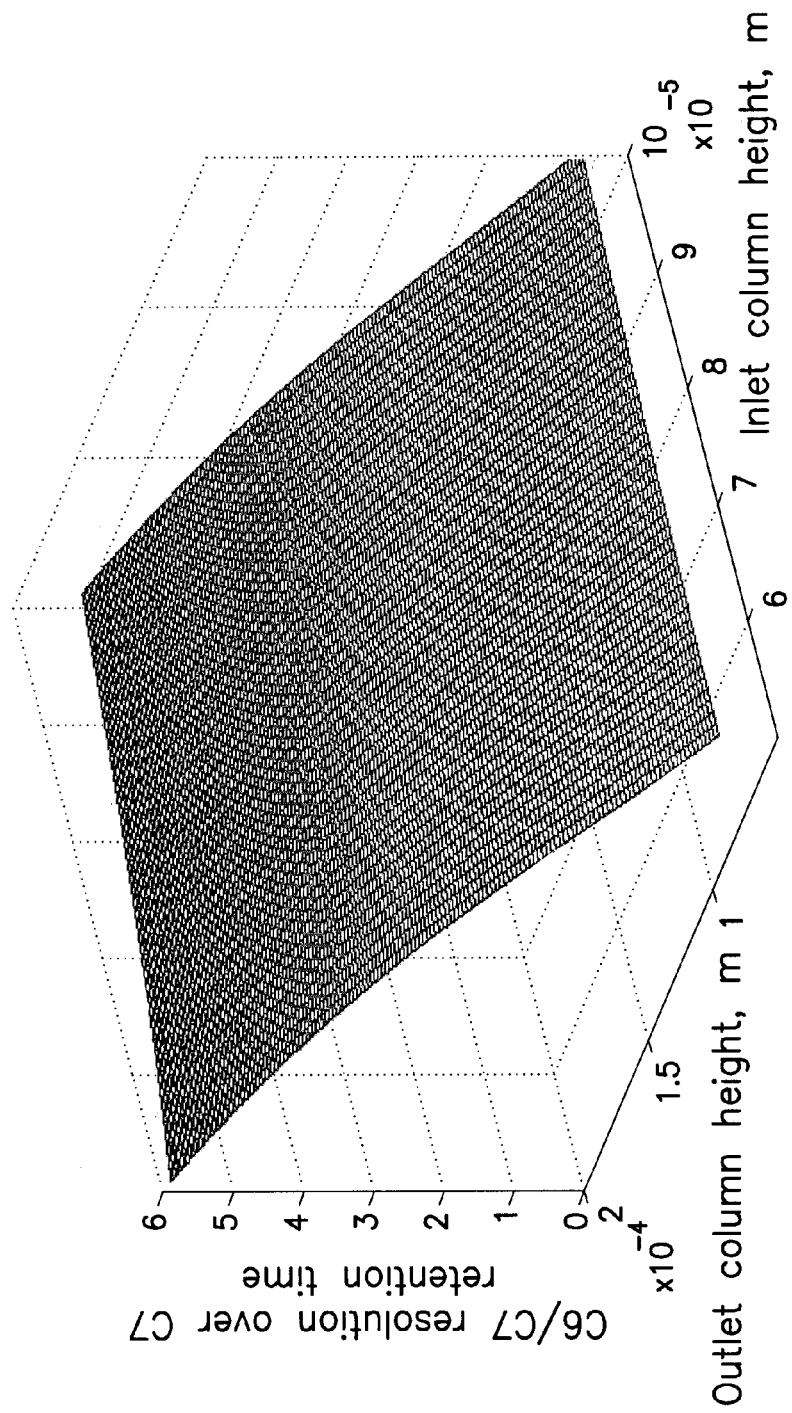
Figure 15E:
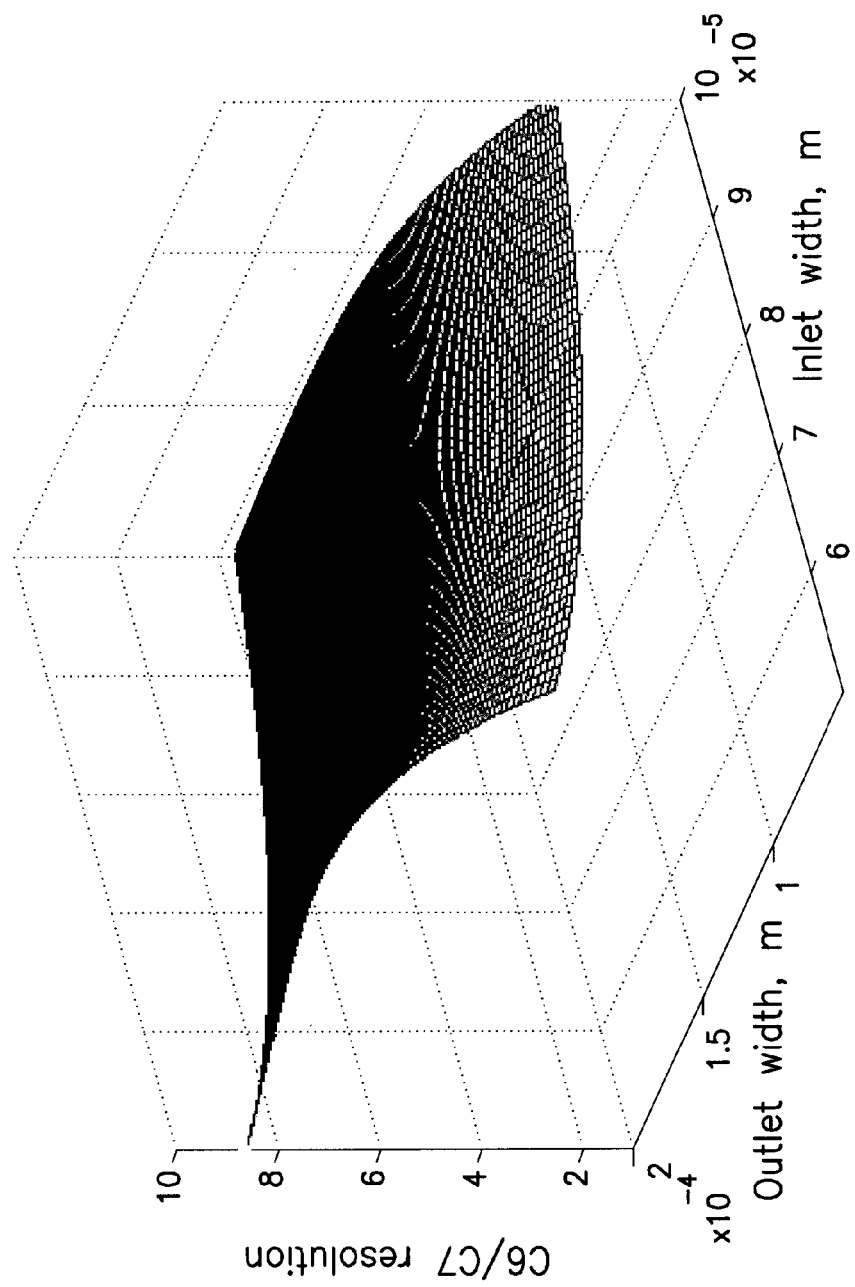
FIGS. 15e-15f illustrate the effect of inlet-outlet column width modulation on the $C_6/C_7$ peaks resolution and $C_6/C_7$ peaks resolution over $C_7$ retention time.
Figure 15F:
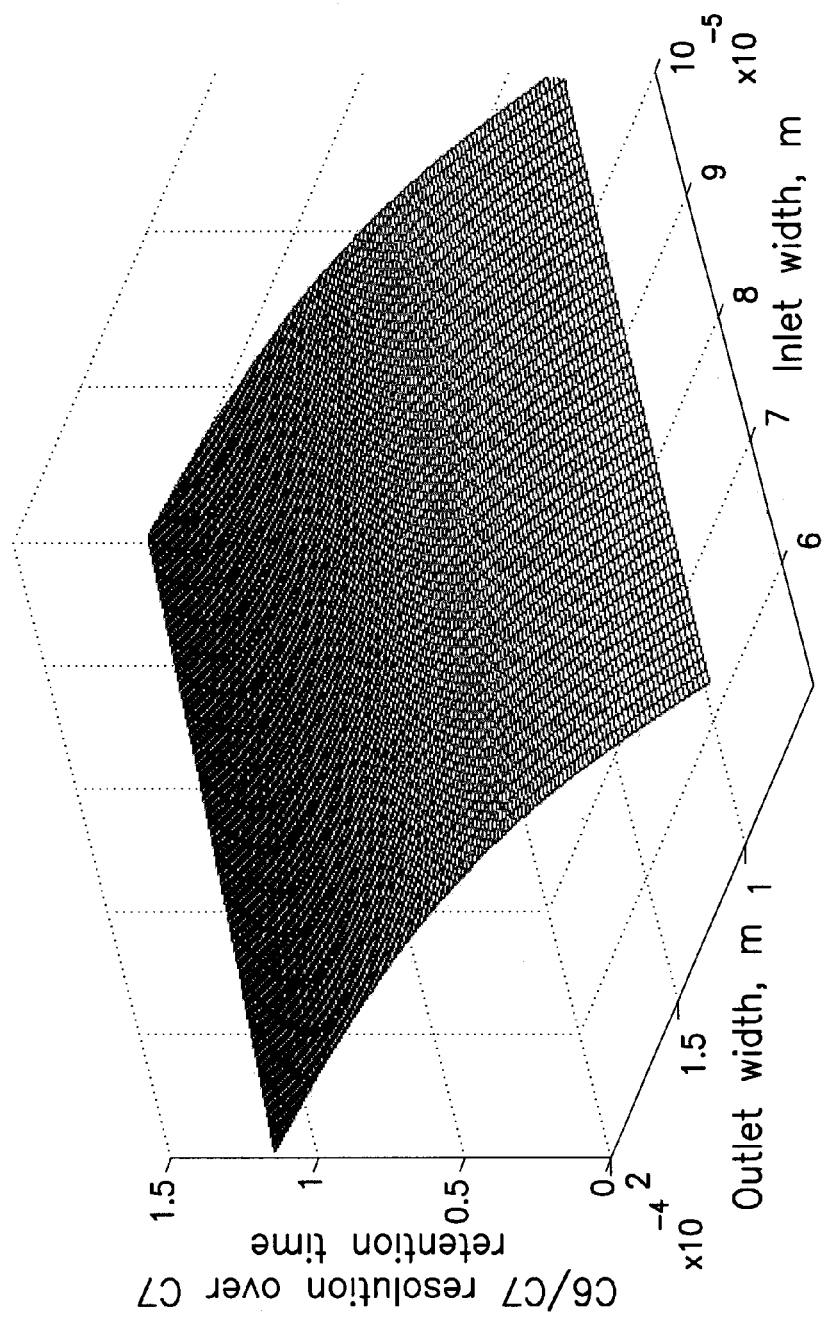
Figure 15G:
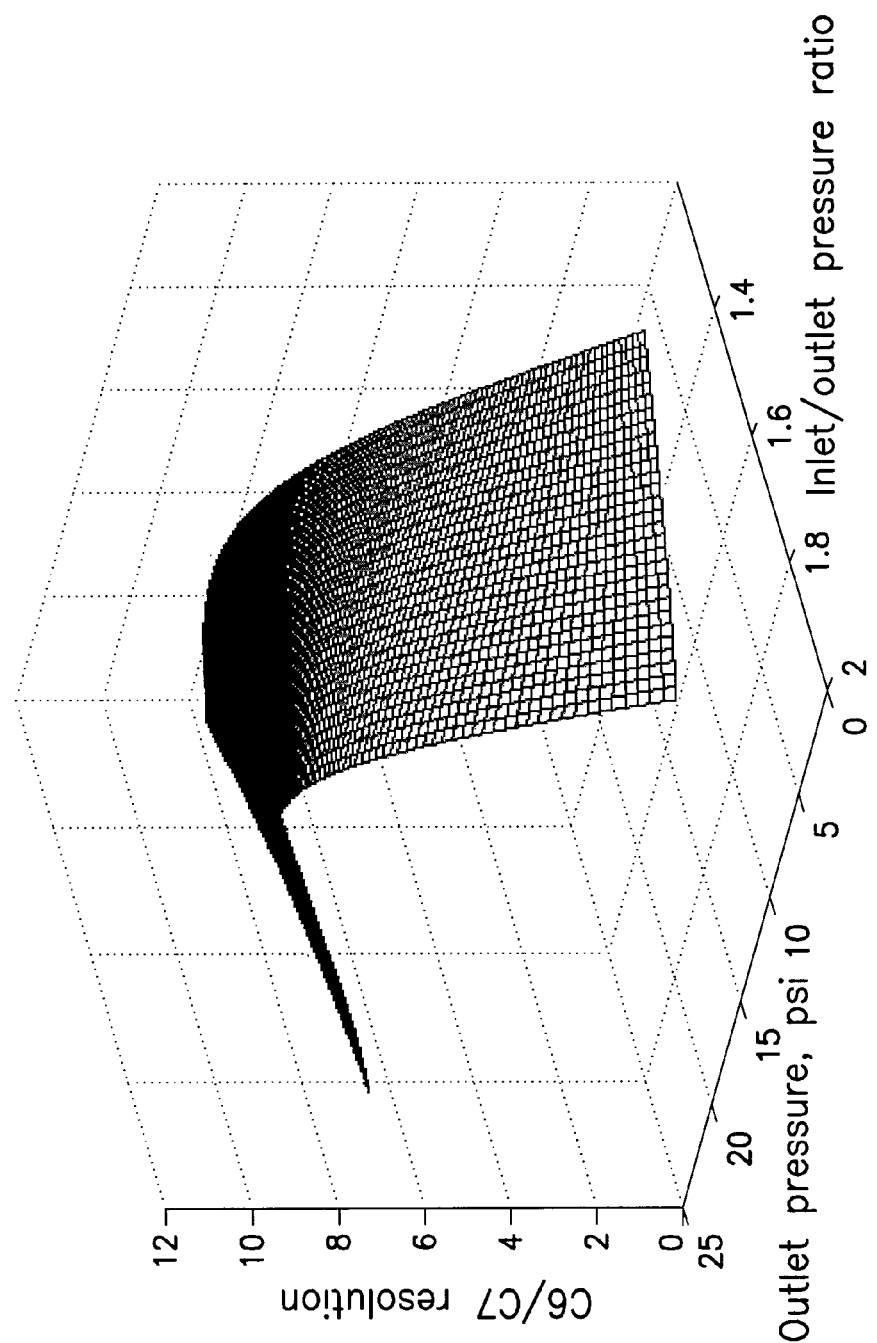
FIGS. 15g-15h illustrate the effect of outlet pressure and inlet/outlet pressure ratio on the $C_6/C_7$ peaks resolution in case of the column with width and stationary phase thickness modulations.
Figure 15H:
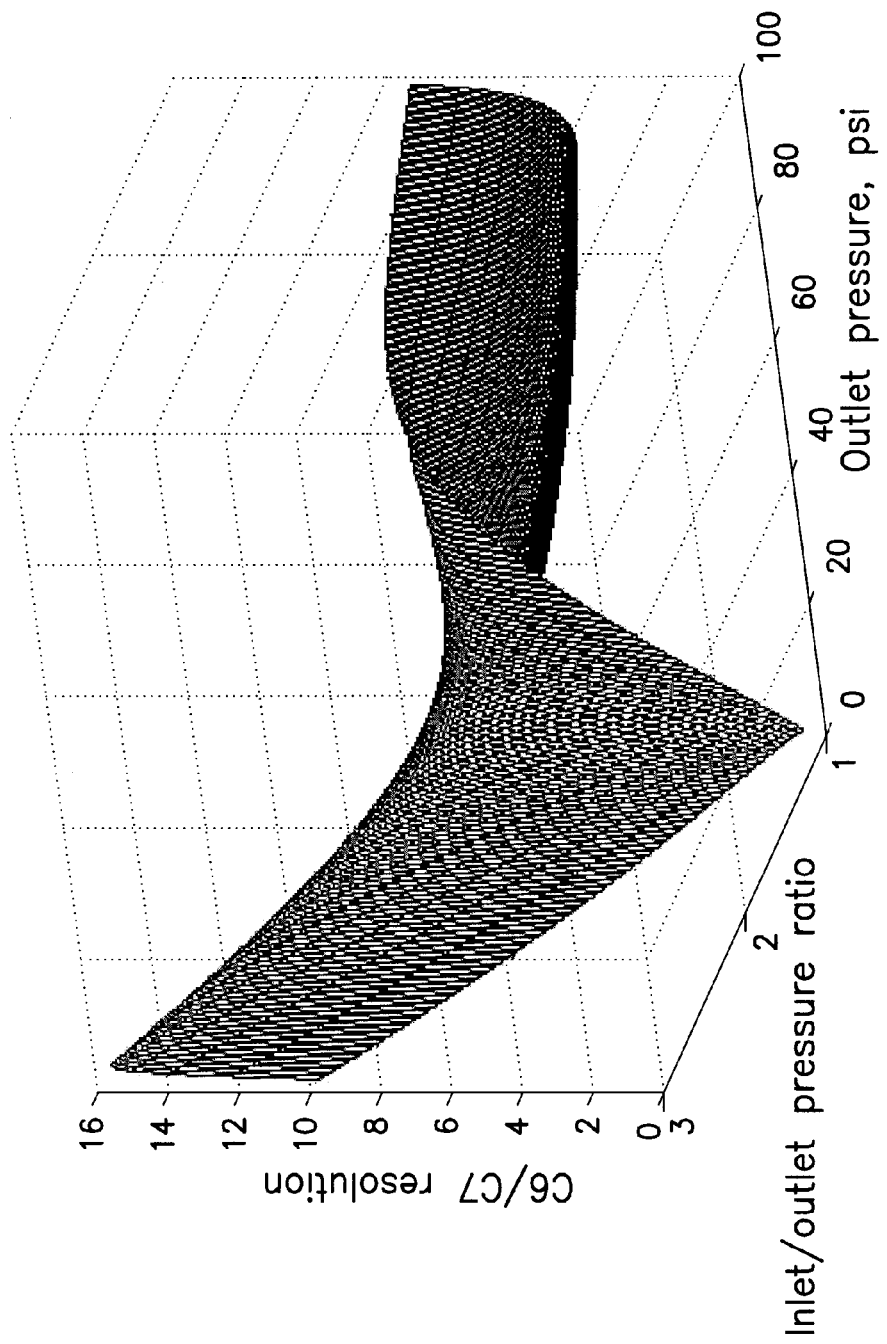
Figure 16:
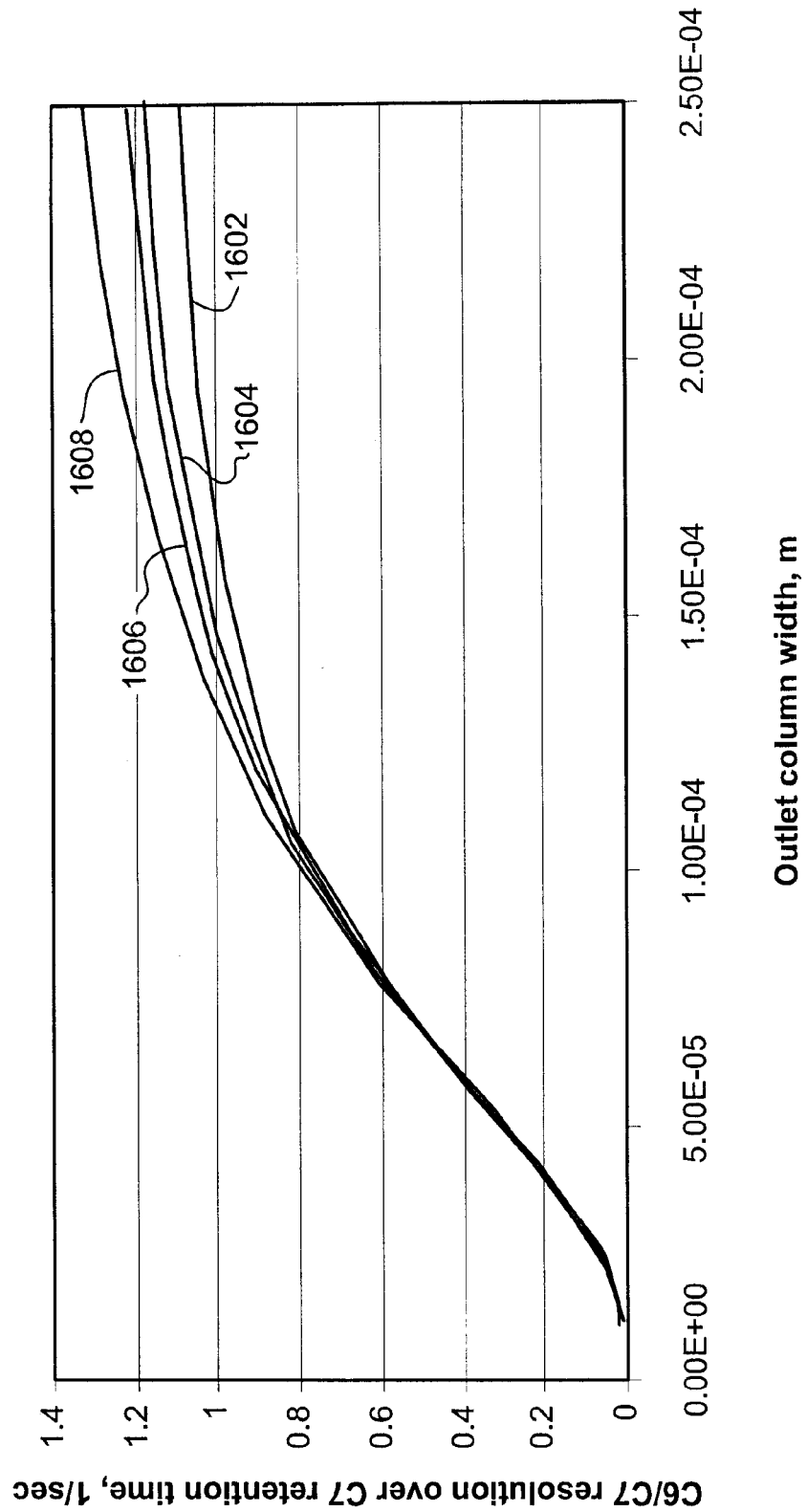
FIG. 16 illustrates the effect of different profile selection for column width modulation on C6/C7 peaks resolution over C7 retention time.
Figure 17:
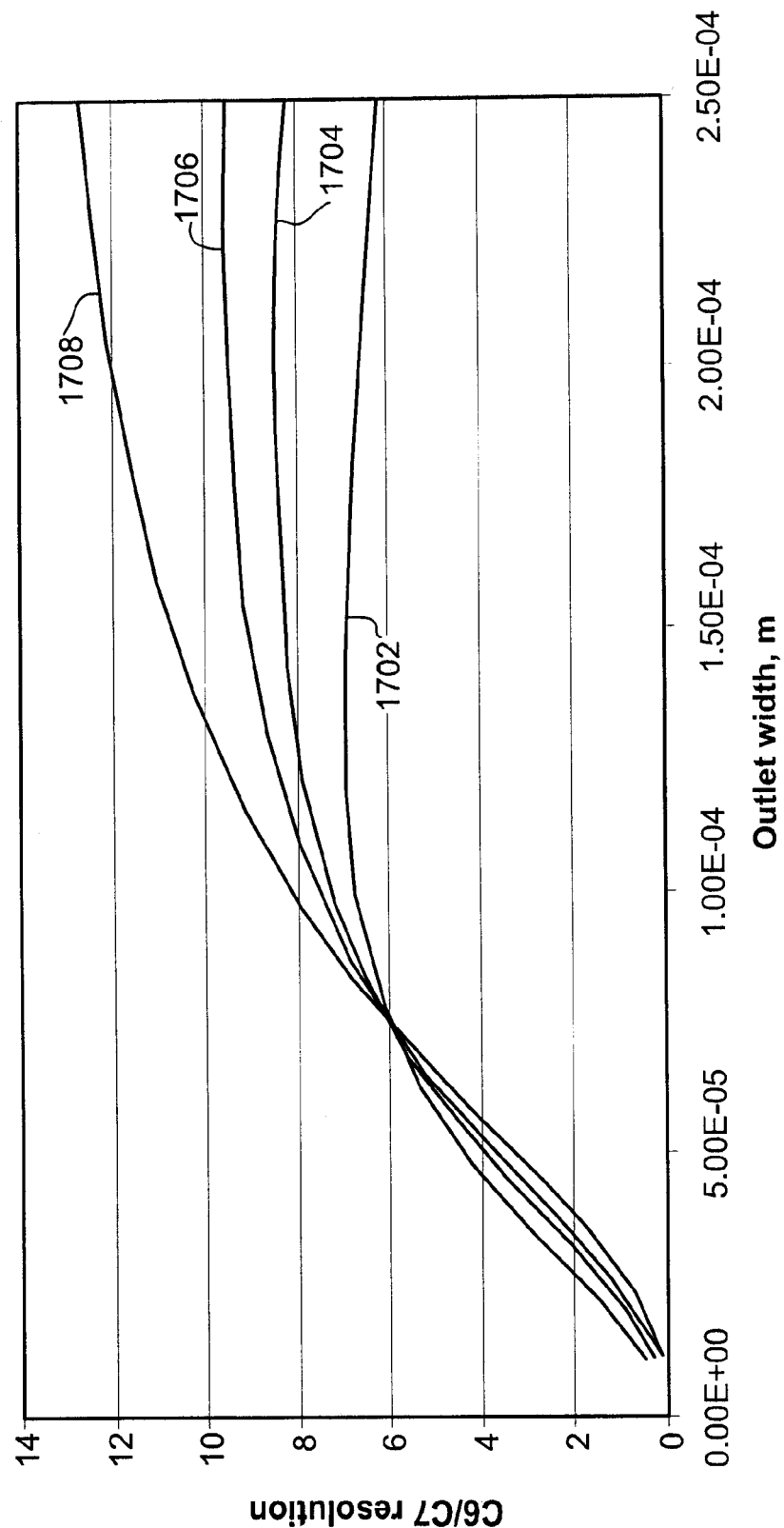
FIG. 17 illustrates the effect of different profile selection for column width modulation on C6/C7 peaks resolution.

FIGS. 15a-15b illustrate the effect of inlet-outlet stationary phase thickness modulation on the $C_6/C_7$ peaks resolution and $C_6/C_7$ peaks resolution over $C_7$ retention time. FIGS. 15c-15d illustrate the effect of inlet-outlet column height modulation on the $C_6/C_7$ peaks resolution and $C_6/C_7$ peaks resolution over $C_7$ retention time. FIGS. 15e-15f illustrate the effect of inlet-outlet column width modulation on the $C_6/C_7$ peaks resolution and $C_6/C_7$ peaks resolution over $C_7$ retention time. FIGS. 15g-15h illustrate the effect of outlet pressure and inlet/outlet pressure ratio on the $C_6/C_7$ peaks resolution in case of the column with width and stationary phase thickness modulations. FIG. 16 illustrates the effect of different profile selection for column width modulation on C6/C7 peaks resolution over C7 retention time. Curve 1602 is for a linear profile, curve 1604 is for a quadratic profile, curve 1606 is for a cubic profile, and curve 1608 is an ×10 profile. FIG. 17 illustrates the effect of different profile selection for column width modulation on C6/C7 peaks resolution. Curve 1702 is for a linear profile, curve 1704 is for a quadratic profile, curve 1706 is for a cubic profile, and curve 1708 is an ×10 profile.

The starting point for the modeling was as follows: column width 75 microns, column height 75 microns, stationary phase thickness 2 microns. In case of modulation: final column width is 150 microns, for the column height initial is 75 microns and the final is 150 microns. For the stationary phase thickness the following starting points were used: the initial thickness is 2 microns, and the final thickness is 1 micron. Temperature was kept isothermal at 100 degC, and the inlet pressure is 5 psig. The pressure at the column inlet was varied from 1 psig to 160 psig. Three column width modulation cases were evaluated: (1) column height=45 microns, (2) column height=75 microns; and (3) column height=105 microns. There are no significant differences between these three columns. All columns behave similarly and peaks resolution is improving going from linear to more nonlinear profiles (order of the columns according to resolution improvement: constant profile-linear width increment-exponential width increment-quadratic width increment-cubic width increment and so on). As expected the profile $x^{1/N}$, where N is increased towards infinity, is the optimum profile for the stationary phase modulation in case of minimization of the time of experiment. Based on the results, the columns with 75 micron or 105 micron column heights are preferred: since the retention time increased dramatically going from 105 micron to 45 micron (2.78 sec→4.56 sec→12.43 sec) but resolutions are very similar (6.18→6.89→7.39).

Variation of the column height is more efficient for the improvement of the resolution over time parameter (as was mentioned the column height should increase along the column) and this modulation is also more effective compare to column with width modulation to decrease the retention time.

The effect of stationary phase on the column performance is the same as for circular column—it also should decrease to the column end as was shown for the circular column and as for the circular geometry there is the optimum profile in case of optimization of the resolution over time parameter. The optimum column inlet pressure for this geometry is around several psig (2-3 psig).

It is known that different approximations of the transport equation solution can provide slightly different results. In the case of the Spangler approximation the peak width is smaller especially for heavy components compared to the Golay approximation. This can be easily explained by the fact that in the Golay equation for the rectangular geometry column there is ratio $(W+H)^2/H^2$ that in case of similar column width and height basically multiply the term that corresponds to peak dispersion due to nonequilibrium effects in the stationary phase by 4. For lighter components the contribution of the nonequilibrium effects in stationary phase is negligible compared to contribution from the mobile phase dispersion. However, for heavier components the opposite is true and in differences can be significant.

Although theoretically it is possible to achieve significant improvement of chromatography performance by applying described above techniques of variation of column width, height, and stationary phase thickness, due to current manufacturing limitations, column width and stationary phase thickness are preferably varied along the column.

Although much discussion has been made herein regarding the design of the chromatographic column, it is also important to carefully select the other components in the chromatography system that can have significant effects on the performance of the overall system. Among the most important parameters that can significantly degrade the performance of the chromatography system are time of injection and extra-column dispersion (the dead volume of all connectors, detector and injector). Modeling was used to evaluate the effect of these parameters and provide guidance during the selection of these parameters.

Figure 18A:
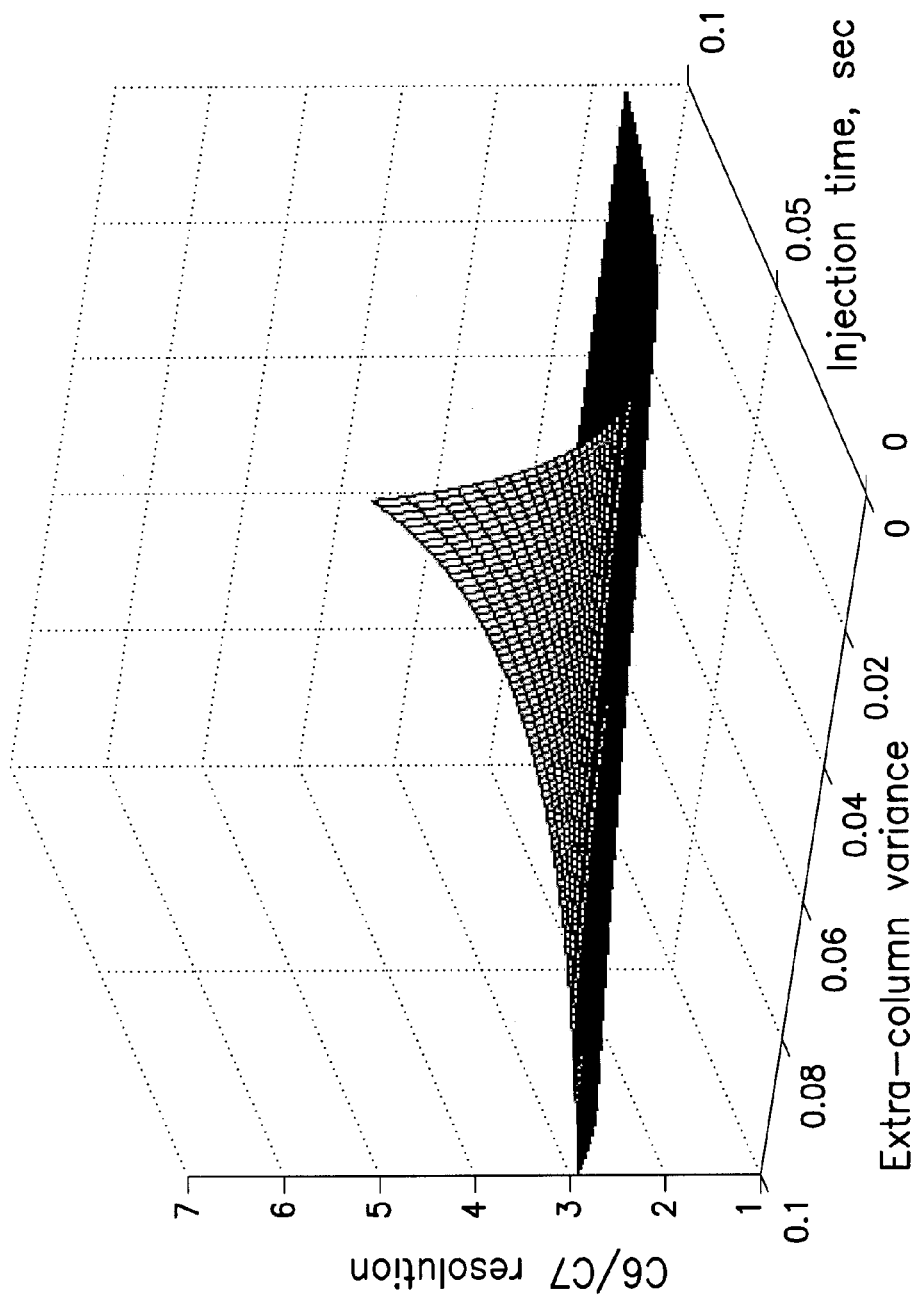
FIGS. 18a-18b illustrate the effect of the finite duration of the injection slug and extra-column variance on peaks resolution.
Figure 18B:
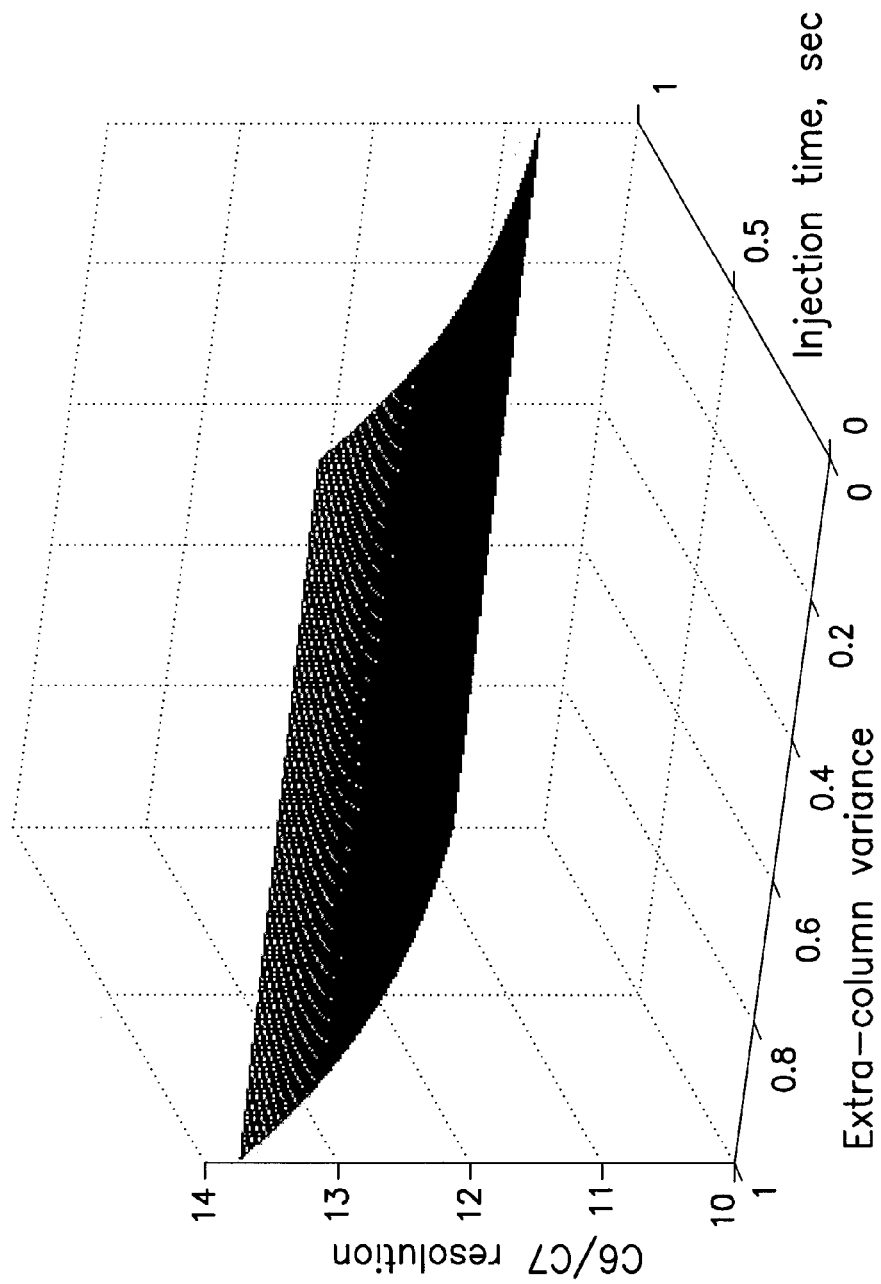

FIGS. 18a-18b illustrate the effect of the finite duration of the injection slug and extra-column variance on peaks resolution. FIG. 18a shows the extra-column variance [$sec^2$] effect on $C_6/C_7$ peaks resolution in case of a 1 meter column having linear column width profile: initial column radius=90 µm and final radius=180 µm. FIG. 18b shows the same effect and conditions for a column of 10 meter length. As can be seen from FIGS. 18a and 18b, in case of longer column the effect of injection time becomes much less significant compare to extra-column dispersion. Accordingly, a shorter column benefits from a sharper injection plug.

Based on the evaluations describe herein, and on general requirements for downhole applications like a minimization of gas consumption (or low inlet/outlet pressure ratio) it has been found that providing a linear modulation of the column having the radii and the stationary phase thicknesses as follows is suitable for downhole oilfield applications. The outlet column radius—should be bigger than inlet radius. The recommended range is about 300-350 µm. The optimum value, however, depends on the set of experimental conditions such as separated components, inlet/outlet pressure ratio, column length, column temperature, outlet pressure, and stationary phase thickness. For the inlet column radius, a value found to be suitable for RoT parameter is about 50-100 µm. Again, the option value for a given application depends on the set of experimental conditions such as separated components, inlet/outlet pressure ratio, column length, column temperature, outlet pressure, and stationary phase thickness. The stationary phase thickness at the column outlet should be minimized and should be thinner than thickness of stationary phase at the column inlet. The stationary phase thickness at the column inlet in the range of about 2-4 µm has been found suitable. For RoT there selected value depends on the set of experimental conditions such as separated components, inlet/outlet pressure ratio, column length, column temperature, outlet pressure and stationary phase thickness.

For a rectangular column geometry manufactured using MEMs technology having a constant column height, the following has been found to be suitable. The outlet column width should be bigger than inlet column width. The recommended range is about 120-300 µm, and depends on the set of experimental conditions such as separated components, inlet/outlet pressure ratio, column length, column temperature, outlet pressure and stationary phase thickness, etc. For the inlet column width, there is in general a trade off between resolution and time of experiment value. However, a valued of about 50-100 µm has been found suitable. The stationary phase thickness at the column outlet should be minimized. For the stationary phase thickness at the column inlet a value of about 2-4 µm has been found to be suitable. For RoT there the best value depends on the set of experimental conditions such as the separated components, inlet/outlet pressure ratio, column length, column temperature, outlet pressure and stationary phase thickness.

Figure 19:
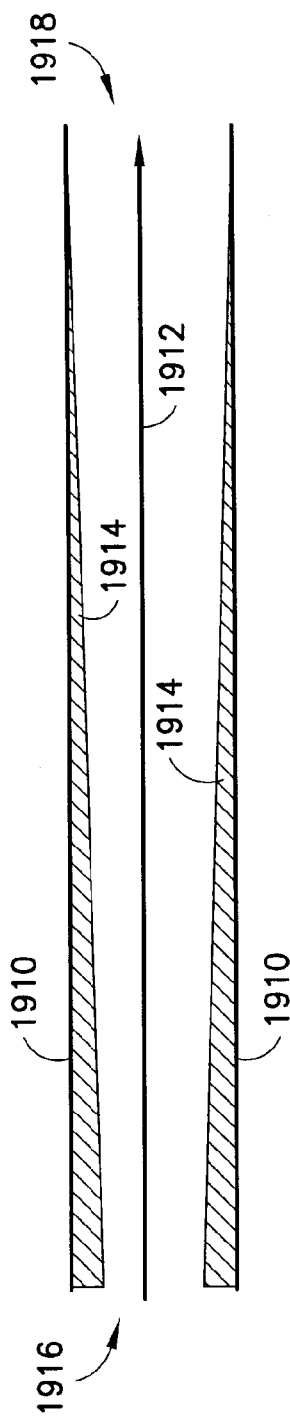
FIG. 19 is a side view of a column of a chromatographic system having variable stationary phase film thickness, according to embodiments.

Several embodiments will now be described in further detail. FIG. 19 is a side view of a column of a chromatographic system having variable stationary phase film thickness, according to embodiments. Open tubular column 1910 is shown with the mobile phase, arrow 1912, flowing from inlet 1916 towards outlet 1918. The stationary phase is deposited as a film 1914 on the inner surface of column 1910. In the arrangement shown in FIG. 19, differential acceleration is provided by varying the thickness of stationary phase film 1914 such that film 1914 is thicker at the inlet 1916 and thinner at the outlet 1918.

According to an embodiment, the arrangement shown in FIG. 19 is used for gas chromatography (GC). In this embodiment, the tubular, constant diameter column 1910 is easily available, robust, and compatible with existing gas chromatographs. For example, column 1910 can be a commercially-available polyimide-coated, fused silica column with an undeactivated inner glass surface. The stationary phase film 1914 is doped with cross-linking agents, and can then be deposited in the fused silica tube-column 1910 in such a way that the film thickness decreases down the length of the column, being as close to zero thickness as possible at outlet 1918. The stationary phase should then be cross-linked using standard literature procedures. For further detail relating to cross-linking agents, cross-linking and stationary phase deposition, see Anal. Chem. 2004, 76(9), 2629-2637; and Anal. Chem. 2006, 78(8), 2623-2630 which are both incorporated by reference herein. The preferred inner diameter and length of the column, as well as starting stationary phase thickness, and the rate/function of film tapering, should vary with each application.

Figure 20:
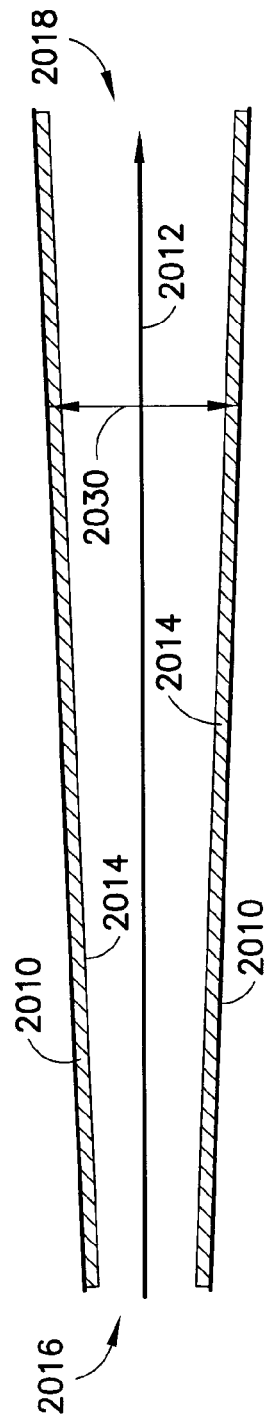
FIG. 20 is a side view of a column of a chromatographic system having variable column cross sectional area, according to embodiments.

FIG. 20 is a side view of a column of a chromatographic system having variable column cross sectional area, according to embodiments. Open tubular column 2010 is shown with the mobile phase, arrow 2012, flowing from inlet 2016 towards outlet 2018. The stationary phase is deposited as a film 2014 on the inner surface of column 2010. In the arrangement shown in FIG. 20, differential acceleration is provided by varying the cross sectional area of column 2010 such that the cross sectional area of column 2010 is smaller at the inlet 2016 and larger at the outlet 2018.

According to another embodiment, the arrangement shown in FIG. 20 is manufactured using MEMS technology and is used for GC. According to this embodiment, column 2010 is not tubular but rather of rectangular cross-section. The dimension shown vertically in FIG. 20 is the width of column 2010 as shown by arrow 2030. The width is varying, becoming larger in the direction of the outlet 2018. The height of column 2010, not shown, remains constant throughout the length of column 2010 for ease of fabrication. Column 2010 is preferably coated with a stationary phase 2014 of constant thickness. Alternatively, the stationary phase 2014 can be deposited in varying thickness within column 2010, as shown with film 1914 of FIG. 19. The advantages with this approach would be combined sources of differential acceleration through the an expanding cross section and decreasing film thickness, yielding a greater degree of differential acceleration than with only a single source of acceleration.

Figure 21A:
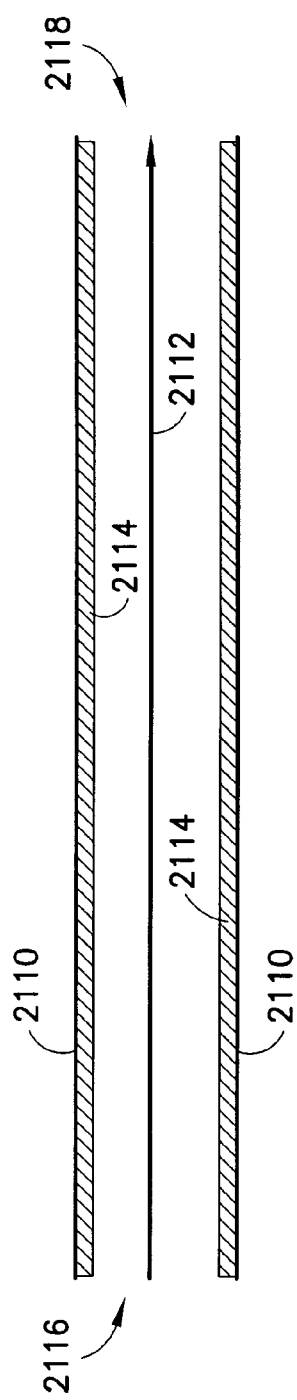
FIGS. 21a-21b show a column of a chromatographic system having a temperature gradient, according to embodiments.
Figure 21B:
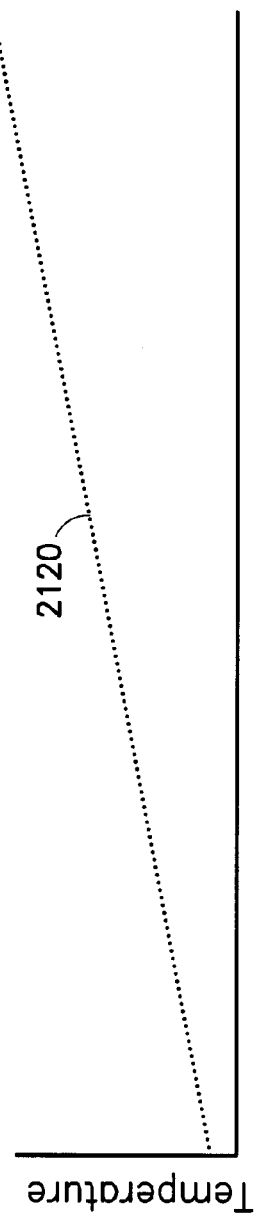

FIGS. 21a-21b show a column of a chromatographic system having a temperature gradient, according to embodiments. In FIG. 21a, open tubular column 2110 is shown with the mobile phase, arrow 2112, flowing from inlet 2116 towards outlet 2118. The stationary phase is deposited as a film 2114 on the inner surface of column 2110. In FIG. 21b, curve 2120 shows temperature of column 2110 as a function of longitudinal position of column 2110. As can be seen, the temperature increases in the direction towards outlet 2118 of column 2110. In the arrangement shown in FIGS. 21a and 21b, differential acceleration is provided by applying different temperatures at different locations along column 2110 such that the temperature of column 2110 is lower at the inlet 2116 and higher at the outlet 2118.

According to another embodiment, column 2110 is a microfabricated GC column such as column 2010 shown and described with respect to FIG. 20, and the stationary film having variable thickness as shown and described with respect to FIG. 19. By providing the additional capability for zone-temperature control, a temperature gradient can be created along the length of the column such that the end of the column is warmer than the beginning, yielding a third source of differential acceleration and therefore further improving chromatographic resolution. The effect is enhanced as the length of each temperature zone decreases such that the temperature gradient becomes smoother.

FIGS. 22a-22b show a column of a chromatographic system having a mobile phase velocity gradient, according to embodiments. In FIG. 22a, open tubular column 2210 is shown with the mobile phase, arrow 2212, flowing from inlet 2216 towards outlet 2218. The stationary phase is deposited as a film 2214 on the inner surface of column 2210. Pressure sources 2240, 2242, 2244 and 2246 are shown with insertion points along the length of column 2210. Although only four pressure sources are shown in FIG. 22a, in practice there can be more or fewer pressure sources depending on the application and the desired smoothness of the mobile phase velocity gradient curve. In FIG. 22b, curve 2220 shows mobile phase velocity within column 2210 as a function of longitudinal position of column 2210. As can be seen, the mobile phase velocity increases in the direction towards outlet 2218 of column 2210. In the arrangement shown in FIGS. 22a and 22b, differential acceleration is provided by applying different pressures at different locations along column 2210 such that the mobile phase velocity of column 2210 is lower at the inlet 2216 and higher at the outlet 2218.

Figure 23A:
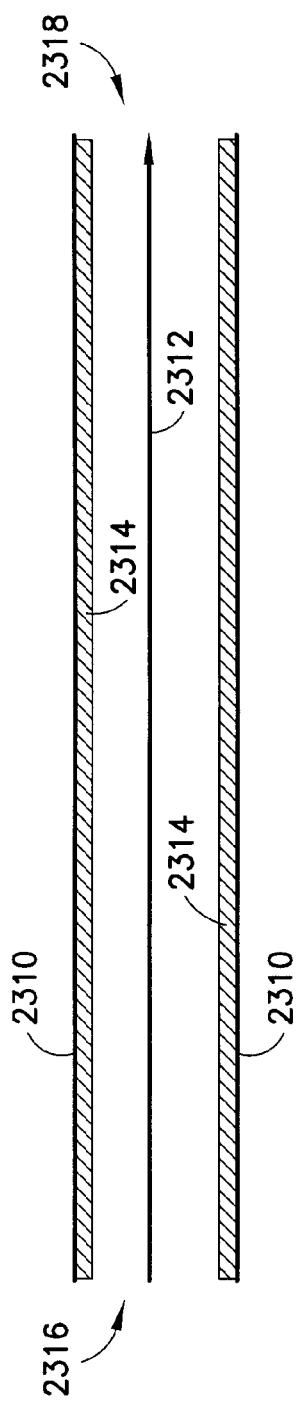
FIGS. 23a-23b show a column of a chromatographic system having a stationary phase with varying chemical composition, according to embodiments.
Figure 23B:
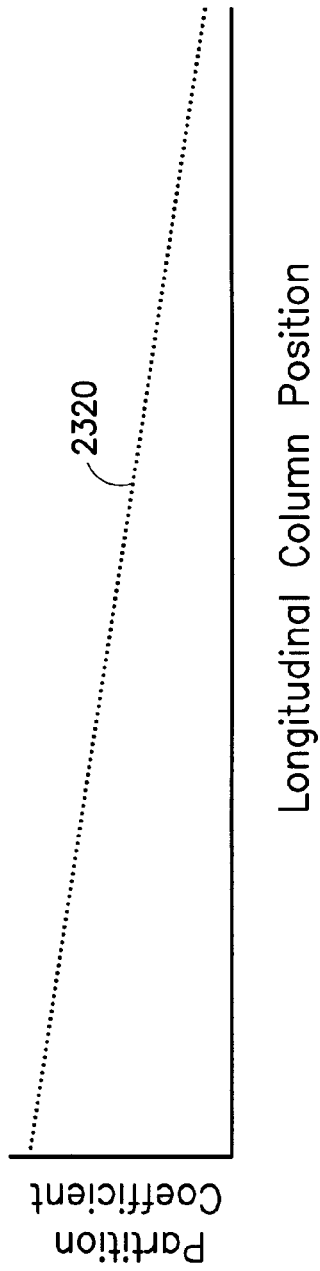

FIGS. 23a-23b show a column of a chromatographic system having a stationary phase with varying chemical composition, according to embodiments. In FIG. 23a, open tubular column 2310 is shown with the mobile phase, arrow 2312, flowing from inlet 2316 towards outlet 2318. The stationary phase is deposited as a film 2314 on the inner surface of column 2310 with a varying chemical composition. In FIG. 23b, curve 2320 shows the partition coefficient within column 2310 as a function of longitudinal position of column 2310. As can be seen, the partition coefficient decreases in the direction towards outlet 2318 of column 2310. In the arrangement shown in FIGS. 23a and 23b, differential acceleration is provided by providing different chemical compositions of the stationary phase at different locations along column 2310 such that the partition coefficient of the stationary phase 2314 is higher at the inlet 2316 and lower at the outlet 2318. One example of a way to achieve decreasing partition coefficient is to vary the degree of cross linking in a stationary phase polymer.

According to other embodiments, combinations of the arrangements shown in FIGS. 19, 20, 21a, 21b, 22a, 22b, 23a and 23b are provided. For example, all five techniques for differential acceleration (variable stationary phase, variable column cross section, temperature gradient, mobile phase velocity gradient, and variable stationary phase chemical composition) can be provided simultaneously for a given column. In general, the limitation in total achievable differential acceleration will result from the effective range over which some column parameters can be varied. For example, GC column inner diameters can conveniently vary from approximately 50 microns to about 500 microns, stationary phases can vary from zero to about 2 micron, and temperature can vary from sub-ambient to about 350° C. An alternative embodiment is to employ multiple sources of differential acceleration in series, rather than simultaneously. This embodiment of course provides less differential acceleration per unit length than for some of the above-mentioned combination schemes. However, by providing the sources in series, and thereby stacking the various parameter ranges in series, a much longer separation may be possible, and therefore more total separation than with the combination scenarios.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, while some of the embodiments described herein refer to gas chromatography, the present invention is also applicable to other types of chromatographic analysis such as liquid chromatography and supercritical fluid chromatography. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for gas chromatographic analysis of a sample containing at least a first component and a second component, the system comprising:
   a column comprising an inlet and an outlet;
   a source of a mobile phase in fluid communication with the column; and
   a stationary phase disposed on an inner surface of the column, wherein the stationary phase has a tapered thickness that decreases along a length of the column from the inlet to the outlet and the tapered thickness imparts a first acceleration on the first component and a second acceleration on the second component as the first component, the second component, and the mobile phase flow through the column.

2. A system according to claim 1, wherein the thickness of the stationary phase varies continuously along the length of the column.

3. A system according to claim 1, wherein the stationary phase is a layer on the inner surface of the column.

4. A system according to claim 3, wherein the thickness of the layer decreases when moving longitudinally along the length of the column from the inlet toward the outlet of the column.

5. A system according to claim 1, wherein a ratio of exposed stationary phase surface area along a segment of the column to a volume at the segment decreases when moving longitudinally along the length of the column towards the outlet of the column.

6. A system according to claim 1, wherein the column has a constant cross section along the length of the column.

7. A system according to claim 6, wherein the column is rectangular in cross section along the length of the column.

8. A system according to claim 6, wherein the column is circular in cross section along the length of the column.

9. A system according to claim 1, wherein both the first acceleration and the second acceleration are positive with respect to time over at least a portion of the length of the column.

10. An apparatus for gas chromatographic analysis of a sample containing at least a first component and a second component, the apparatus comprising:
 a column comprising an inlet and an outlet; and
 a stationary phase disposed on an inner surface of the column, wherein the stationary phase has a tapered thickness that decreases along a length of the column from the inlet to the outlet and the tapered thickness imparts a first acceleration on the first component and a second acceleration on the second component as the first component and the second component flow through the column.

11. An apparatus according to claim 10, wherein the thickness of the stationary phase varies continuously along the length of the column.

12. An apparatus according to claim 10, wherein the stationary phase is a layer on the inner surface of the column.

13. An apparatus according to claim 12, wherein the thickness of the layer decreases when moving longitudinally along the length of the column from the inlet toward the outlet of the column.

14. An apparatus according to claim 10, wherein a ratio of exposed stationary phase surface area along a segment of the column to a volume at the segment decreases when moving longitudinally along the length of the column towards the outlet of the column.

15. An apparatus according to claim 10, wherein the column has a constant cross section along the length of the column.

16. An apparatus according to claim 15, wherein the column is rectangular in cross section along the length of the column.

17. An apparatus according to claim 15, wherein the column is circular in cross section along the length of the column.

18. An apparatus according to claim 10, wherein both the first acceleration and the second acceleration are positive.

19. An apparatus according to claim 10, wherein the apparatus is compatible with existing gas chromatographs.

* * * * *